US011548840B2

(12) United States Patent
Gao et al.

(10) Patent No.: US 11,548,840 B2
(45) Date of Patent: Jan. 10, 2023

(54) CATALYSTS FOR THE OXIDATIVE DEHYDROGENATION OF ALKANES

(71) Applicant: NOVA Chemicals (International) S.A., Fribourg (CH)

(72) Inventors: Xiaoliang Gao, Calgary (CA); Marie Barnes, Calgary (CA); Vasily Simanzhenkov, Calgary (CA); Elena Sebastiao, Calgary (CA); David Sullivan, Calgary (CA); Yoonhee Kim, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 17/546,103

(22) Filed: Dec. 9, 2021

(65) Prior Publication Data

US 2022/0169584 A1    Jun. 2, 2022

Related U.S. Application Data

(62) Division of application No. 16/515,105, filed on Jul. 18, 2019, now Pat. No. 11,230,512.

(Continued)

(51) Int. Cl.
*C07C 5/48* (2006.01)
*B01J 23/28* (2006.01)
(Continued)

(52) U.S. Cl.
CPC ............... *C07C 5/48* (2013.01); *B01J 23/28* (2013.01); *B01J 37/04* (2013.01); *B01J 37/06* (2013.01);
(Continued)

(58) Field of Classification Search
CPC .......... C07C 5/48; C07C 11/04; C07C 11/06; C07C 2523/20; C07C 2523/22; C07C 2523/28; C07C 11/08; B01J 27/0576; B01J 23/002; B01J 23/28; B01J 37/04; B01J 35/002; B01J 35/023; B01J 37/0009;
(Continued)

(56) References Cited

U.S. PATENT DOCUMENTS 8,846,996 B2   9/2014  Kustov et al.
10,350,582 B2  7/2019  Simanzhenkov et al.
(Continued)

FOREIGN PATENT DOCUMENTS

CA    2 655 841 A1    8/2010
DE    198 36 359 A1   3/1999
(Continued)

OTHER PUBLICATIONS

Ishikawa, Satoshi; Goto, Yoshinori; Kawahara, Yoshito; Inukai, Shoma; Hiyoshi, Norihito; Dummer, Nicholas F.; Murayama, Toru; Yoshida, Akihiro; Sadakane, Masahiro and Ueda, Wataru; Synthesis of Crystaline Microporous Mo—V—Bi Oxide for Selective (Amm)Oxidation of Light Alkanes; Copyright 2017, Chem. Mater., vol. 29, pp. 2939-2950.

(Continued)

*Primary Examiner* — Sharon Pregler
(74) *Attorney, Agent, or Firm* — Thomas J. Styslinger

(57) ABSTRACT

This document relates to oxidative dehydrogenation catalysts that include molybdenum, vanadium, and oxygen.

25 Claims, 13 Drawing Sheets

Related U.S. Application Data

(60) Provisional application No. 62/700,468, filed on Jul. 19, 2018.

(51) Int. Cl.
  *B01J 37/04* (2006.01)
  *B01J 37/06* (2006.01)
  *B01J 37/08* (2006.01)
  *B01J 37/10* (2006.01)

(52) U.S. Cl.
  CPC ............ *B01J 37/088* (2013.01); *B01J 37/10* (2013.01); *C07C 2523/22* (2013.01); *C07C 2523/28* (2013.01)

(58) Field of Classification Search
  CPC ...... B01J 37/0036; B01J 37/031; B01J 37/06; B01J 37/088; B01J 37/10; B01J 37/14
  See application file for complete search history.

(56) References Cited

U.S. PATENT DOCUMENTS

| | | | |
|---|---|---|---|
| 10,406,517 | B2 | 9/2019 | Simanzhenkov et al. |
| 10,576,461 | B2 | 3/2020 | Simanzhenkov et al. |
| 10,589,258 | B2 | 3/2020 | Simanzhenkov et al. |
| 2006/0004228 | A1 | 1/2006 | Hazin |
| 2010/0256432 | A1* | 10/2010 | Arnold .................... C07C 5/48 585/655 |
| 2015/0119622 | A1 | 4/2015 | De Rooij et al. |
| 2018/0104675 | A1 | 4/2018 | Simanzhenkov et al. |
| 2019/0039050 | A1 | 2/2019 | Gao et al. |
| 2019/0039053 | A1 | 2/2019 | Kim et al. |
| 2019/0240647 | A1 | 4/2019 | Gao et al. |
| 2019/0291080 | A1 | 9/2019 | Simanzhenkov et al. |

FOREIGN PATENT DOCUMENTS

| | | |
|---|---|---|
| EP | 1 080 784 A1 | 3/2001 |
| EP | 1 574 253 A2 | 9/2005 |
| WO | 2008/068332 A1 | 6/2008 |

OTHER PUBLICATIONS

Vitry, D.; Morikawa, Y.; Dubois, J.L. and Ueda, W.; Mo—v—Te—(Nb)—O mixed metal oxides prepared by hydrothermal systhesis for catalytic selective oxidations of propane and propene to acrylic acid; Copyright 2003, Applied Catalysis A: General 25, pp. 411-424.

Ishchenko, E.V.; Andrushkevich, T.V.; Popova, G.Ya.; Kardash, T.Yu.; Ishchenko, A.V.; Dovlitova, L.S. and Chesalov, Yu.A.; The structure and catalytic properties of amorphous phase in MoVTeO catalysts for propane ammoxidation; Copyright 2014, Applied Catalysis A: General 476, pp. 91-102.

Chu, Bozhao; Truter, Lara; Nijhuis, T.A. and Cheng, Yi; Performance of phase-pure M1 MoVNbTeOx catalysts by hydrothermal synthesis with different post-treatments for the oxidative dehydrogenation of ethane; Applied Catalysis A, General 438 (2015), pp. 99-106.

* cited by examiner

CATALYSTS FOR THE OXIDATIVE DEHYDROGENATION OF ALKANES

CROSS REFERENCE TO RELATED APPLICATIONS

This application is a divisional application of U.S. patent application Ser. No. 16/515,105, filed Jul. 18, 2019, now U.S. Pat. No. 11,230,512, entitled "CATALYSTS FOR THE OXIDATIVE DEHYDROGENATION OF ALKANES," which claims the benefit of U.S. Provisional Application No. 62/700,468, filed on Jul. 19, 2018, entitled "CATALYSTS FOR THE OXIDATIVE DEHYDROGENATION OF ALKANES." The disclosures of these applications are incorporated by reference herein in their entirety.

TECHNICAL FIELD

The present disclosure relates to catalysts for the oxidative dehydrogenation of alkanes such as ethane.

BACKGROUND

Conversion of alkanes to olefins can be achieved in a number of ways. The most widely practiced method is thermal cracking technology, where alkanes are exposed to temperatures of at least 700° C. for very short time periods, in the order of milliseconds to a few seconds, promoting the loss of hydrogen and subsequent formation of one or more unsaturated bonds. However, current thermal cracking processes are not only cost intensive to build and operate but also energy intensive due to the substantial heat requirement for the endothermic cracking reactions.

Alternatively, conversion of alkanes to olefins can be accomplished using an oxidative dehydrogenation (ODH) process where a stream of one or more alkanes are passed over an oxidative dehydrogenation catalyst, in the presence of oxygen at temperatures from about 300° C. to 750° C.

SUMMARY

Provided in this disclosure is an oxidative dehydrogenation catalyst that includes molybdenum, vanadium, and oxygen, wherein the molar ratio of molybdenum to vanadium in the catalyst is from 1:0.15 to 1:0.75, and oxygen is present in the catalyst at least in an amount to satisfy the valency of any present metal oxides.

In some embodiments, the amorphous phase of the catalyst is greater than 55 wt. %.

In some embodiments, the molar ratio of molybdenum to vanadium in the catalyst is from 1:0.20 to 1:0.70.

In some embodiments, the molar ratio of molybdenum to vanadium in the catalyst is from 1:0.25 to 1:0.65.

In some embodiments, the molar ratio of molybdenum to vanadium in the catalyst is from 1:0.29 to 1:0.59.

In some embodiments, the molar ratio of molybdenum to vanadium in the catalyst is from 1:0.32 to 1:0.38.

In some embodiments, the molar ratio of molybdenum to vanadium in the catalyst is from 1:0.36 to 1:0.43.

In some embodiments, the molar ratio of molybdenum to vanadium in the catalyst is from 1:0.37 to 1:0.44.

In some embodiments, the molar ratio of molybdenum to vanadium in the catalyst is from 1:0.41 to 1:0.48.

In some embodiments, the molar ratio of molybdenum to vanadium in the catalyst is from 1:0.42 to 1:0.46.

In some embodiments, the molar ratio of molybdenum to vanadium in the catalyst is from 1:0.44 to 1:0.52.

In some embodiments, the molar ratio of molybdenum to vanadium in the catalyst is from 1:0.45 to 1:0.54.

In some embodiments, the molar ratio of molybdenum to vanadium in the catalyst is from 1:0.50 to 1:0.59.

In some embodiments, the catalyst has an amorphous phase of from 55 wt. % to 80 wt. %.

In some embodiments, the catalyst has an amorphous phase of from 55 wt. % to 75 wt. %.

In some embodiments, the catalyst has a 35% conversion temperature from about 300° C. to about 400° C.

In some embodiments, the catalyst has a 35% conversion temperature from about 310° C. to about 385° C.

In some embodiments, the catalyst has a 35% conversion temperature from about 310° C. to about 375° C.

In some embodiments, the catalyst has a 35% conversion temperature from about 360° C. to about 380° C.

In some embodiments, the catalyst has a 35% conversion temperature from about 310° C. to about 330° C.

In some embodiments, the catalyst has a selectivity to ethylene from about 65% to about 99%.

In some embodiments, the catalyst has a selectivity to ethylene from about 75% to about 80%.

In some embodiments, the catalyst has a selectivity to ethylene from about 80% to about 90%.

In some embodiments, the catalyst has a 35% conversion temperature from about 310° C. to about 385° C. and a selectivity to ethylene from about 75% to about 90%.

In some embodiments, the catalyst has a 35% conversion temperature from about 360° C. to about 380° C. and a selectivity to ethylene from about 75% to about 80%.

In some embodiments, the catalyst has a 35% conversion temperature from about 310° C. to about 330° C. and a selectivity to ethylene from 80% to 90%.

In some embodiments, the catalyst is prepared by a method that includes providing an aqueous mixture including molybdenum and vanadium, hydrothermally reacting the mixture to form a precalcined catalyst, and calcining the precalcined catalyst to form the catalyst.

In some embodiments, providing the aqueous mixture including molybdenum and vanadium includes combining an aqueous mixture including molybdenum and an aqueous mixture including vanadium.

In some embodiments, the aqueous mixture including molybdenum is prepared from at least $(NH_4)_6Mo_7O_{24} \cdot 4H_2O$ and a first water. In some embodiments, the aqueous mixture including vanadium is prepared from at least $VOSO_4 \cdot XH_2O$ and a second water. In some embodiments, the first and the second water are selected from distilled water, deionized water, demineralized water, mineral water, or a combination thereof. In some embodiments, the first and second water include distilled water.

In some embodiments, the aqueous mixture including molybdenum and vanadium further includes a surfactant. In some embodiments, the surfactant is selected from a nonionic surfactant, an anionic surfactant, a cationic surfactant, or a combination thereof. In some embodiments, the anionic surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof. In some embodiments, the anionic surfactant includes sodium dodecyl sulfate. In some embodiments, the anionic surfactant includes sodium octyl sulfate.

In some embodiments, hydrothermally reacting the mixture to form the precalcined catalyst includes heating the aqueous mixture of molybdenum and vanadium in the presence of a catalyst seed.

In some embodiments, the catalyst seed includes a composition including molybdenum and vanadium. In some embodiments, the composition including molybdenum and vanadium includes a catalyst including molybdenum, vanadium, and oxygen, wherein the molar ratio of molybdenum to vanadium in the catalyst is from 1:0.15 to 1:0.75.

In some embodiments, the catalyst seed includes a composition including molybdenum, vanadium, niobium, and tellurium. In some embodiments, the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40; and wherein oxygen is present at least in an amount to satisfy the valency of any present metal oxides.

In some embodiments, hydrothermally reacting the mixture to form a precalcined catalyst includes heating the aqueous mixture of molybdenum and vanadium at a temperature from about 150° C. to about 300° C.

In some embodiments, hydrothermally reacting the mixture to form a precalcined catalyst includes heating the aqueous mixture of molybdenum and vanadium at a temperature from about 200° C. to about 250° C.

In some embodiments, hydrothermally reacting the mixture to form a precalcined catalyst includes heating the aqueous mixture of molybdenum and vanadium at a temperature from about 230° C.

In some embodiments, hydrothermally reacting the mixture to form a precalcined catalyst includes heating the aqueous mixture of molybdenum and vanadium under a pressure from about 1 psi to about 1,500 psi.

In some embodiments, hydrothermally reacting the mixture to form a precalcined catalyst includes heating the aqueous mixture of molybdenum and vanadium under a pressure from about 400 psi to about 440 psi.

In some embodiments, hydrothermally reacting the mixture to form a precalcined catalyst includes heating the aqueous mixture of molybdenum and vanadium at a temperature from about 200° C. to about 250° C. under a pressure from about 200 psi to about 900 psi.

In some embodiments, hydrothermally reacting the mixture to form a precalcined catalyst includes heating the aqueous mixture of molybdenum and vanadium at a temperature from about 230° C. under a pressure from about 400 psi to about 440 psi.

In some embodiments, hydrothermally reacting the mixture to form a precalcined catalyst includes contacting the mixture with a glass liner, stainless steel, or Teflon liner. In some embodiments, hydrothermally reacting the mixture to form a precalcined catalyst includes contacting the mixture with a glass liner. In some embodiments, hydrothermally reacting the mixture to form a precalcined catalyst includes contacting the mixture with a Teflon liner.

In some embodiments, the precalcined catalyst is calcined at about 300° C. to about 500° C.

In some embodiments, the precalcined catalyst is calcined at about 375° C. to about 425° C.

In some embodiments, the precalcined catalyst is calcined at about 400° C.

In some embodiments, the precalcined catalyst is calcined at about 300° C. to about 500° C. for about 1 hour to about 24 hours.

In some embodiments, the precalcined catalyst is calcined at about 375° C. to about 425° C. for about 1 hour to about 4 hours.

In some embodiments, the precalcined catalyst is calcined at about 400° C. for about 2 hours.

Also provided in this disclosure is an oxidative dehydrogenation catalyst including molybdenum, vanadium, and oxygen, wherein the molar ratio of molybdenum to vanadium in the catalyst is from 1:0.20 to 1:0.60, oxygen is present in the catalyst at least in amount to satisfy the valency of any present metal oxides.

In some embodiments, the amorphous phase of the catalyst is greater than 55 wt. %.

In some embodiments, the molar ratio of molybdenum to vanadium in the catalyst is from 1:0.24 to 1:0.58.

In some embodiments, the molar ratio of molybdenum to vanadium in the catalyst is from 1:0.29 to 1:0.53.

In some embodiments, the amorphous phase of the catalyst is from 55 wt. % to 75 wt. %.

In some embodiments, the amorphous phase of the catalyst is from 60 wt. % to 65 wt. %.

In some embodiments, the catalyst characterized by having XRD diffraction peaks (2θ degrees) at least at 23.5±0.5, 25.6±0.5, and 27.1±0.7, wherein the XRD is obtained using CuKα radiation.

In some embodiments, the catalyst is characterized by having XRD diffraction peaks (2θ degrees) at least at 21.7±0.2, 23.5±0.5, 25.0±0.3, 25.6±0.3, and 27.1±0.7, wherein the XRD is obtained using CuKα radiation.

In some embodiments, the catalyst has a 35% conversion temperature from about 300° C. to about 425° C.

In some embodiments, the catalyst has a selectivity to ethylene from 65% to 95%.

In some embodiments, the catalyst is prepared by a method that includes providing an aqueous mixture including molybdenum and vanadium, hydrothermally reacting the mixture to form a precalcined catalyst, and calcining the precalcined catalyst in the presence of air to form the catalyst.

In some embodiments, providing the aqueous mixture including molybdenum and vanadium includes combining an aqueous mixture including molybdenum and an aqueous mixture including vanadium.

In some embodiments, the aqueous mixture including molybdenum is prepared from at least $(NH_4)_6Mo_7O_{24} \cdot 4H_2O$ and a first water. In some embodiments, the aqueous mixture including vanadium is prepared from at least $VOSO_4 \cdot XH_2O$ and a second water. In some embodiments, the first and the second water are selected from distilled water, deionized water, demineralized water, mineral water, or a combination thereof. In some embodiments, the first and second water include distilled water.

In some embodiments, the aqueous mixture including molybdenum and vanadium further includes a surfactant. In some embodiments, the surfactant is selected from a nonionic surfactant, an anionic surfactant, a cationic surfactant, or a combination thereof. In some embodiments, the anionic surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof. In some embodiments, the anionic surfactant includes sodium dodecyl sulfate. In some embodiments, the anionic surfactant includes sodium octyl sulfate.

In some embodiments, hydrothermally reacting the mixture to form the precalcined catalyst includes heating the aqueous mixture of molybdenum and vanadium in the presence of a catalyst seed.

In some embodiments, the catalyst seed includes a composition including molybdenum and vanadium. In some embodiments, the composition including molybdenum and vanadium includes a catalyst including molybdenum, vanadium, and oxygen, wherein the molar ratio of molybdenum to vanadium in the catalyst is from 1:0.15 to 1:0.75.

In some embodiments, the catalyst seed includes a composition including molybdenum, vanadium, niobium, and tellurium. In some embodiments, the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40, and wherein oxygen is present at least in an amount to satisfy the valency of any present metal oxides.

In some embodiments, hydrothermally reacting the mixture to form a precalcined catalyst includes heating the aqueous mixture of molybdenum and vanadium at a temperature from about 150° C. to about 300° C.

In some embodiments, hydrothermally reacting the mixture to form a precalcined catalyst includes heating the aqueous mixture of molybdenum and vanadium at a temperature from about 200° C. to about 250° C.

In some embodiments, hydrothermally reacting the mixture to form a precalcined catalyst includes heating the aqueous mixture of molybdenum and vanadium at a temperature from about 230° C.

In some embodiments, hydrothermally reacting the mixture to form a precalcined catalyst includes heating the aqueous mixture of molybdenum and vanadium under a pressure from about 1 psi to about 1,500 psi.

In some embodiments, hydrothermally reacting the mixture to form a precalcined catalyst includes heating the aqueous mixture of molybdenum and vanadium under a pressure from about 400 psi to about 440 psi.

In some embodiments, hydrothermally reacting the mixture to form a precalcined catalyst includes heating the aqueous mixture of molybdenum and vanadium at a temperature from about 200° C. to about 250° C. under a pressure from about 200 psi to about 900 psi.

In some embodiments, hydrothermally reacting the mixture to form a precalcined catalyst includes heating the aqueous mixture of molybdenum and vanadium at a temperature of about 230° C. under a pressure from about 400 psi to about 440 psi.

In some embodiments, hydrothermally reacting the mixture to form a precalcined catalyst includes contacting the mixture with a glass liner, stainless steel, or Teflon liner. In some embodiments, hydrothermally reacting the mixture to form a precalcined catalyst includes contacting the mixture with a glass liner. In some embodiments, hydrothermally reacting the mixture to form a precalcined catalyst includes contacting the mixture with a Teflon liner.

In some embodiments, the precalcined catalyst is calcined at about 300° C. to about 500° C.

In some embodiments, the precalcined catalyst is calcined at about 375° C. to about 425° C.

In some embodiments, the precalcined catalyst is calcined at about 400° C.

In some embodiments, the precalcined catalyst is calcined at about 300° C. to about 500° C. for about 1 hour to about 24 hours.

In some embodiments, the precalcined catalyst is calcined at about 375° C. to about 425° C. for about 1 hour to about 4 hours.

In some embodiments, the precalcined catalyst is calcined at about 400° C. for about 2 hours.

Also provided in this disclosure is an oxidative dehydrogenation catalyst that includes molybdenum, vanadium, and oxygen, wherein the molar ratio of molybdenum to vanadium in the catalyst is from 1:0.20 to 1:0.50, and oxygen is present in the catalyst at least in amount to satisfy the valency of any present metal oxides.

In some embodiments, the amorphous phase of the catalyst is greater than 55 wt. %.

In some embodiments, the molar ratio of molybdenum to vanadium in the catalyst is from 1:0.25 to 1:0.45.

In some embodiments, the molar ratio of molybdenum to vanadium in the catalyst is from 1:0.29 to 1:0.39.

In some embodiments, the amorphous phase of the catalyst is from 55 wt. % to 85 wt. %.

In some embodiments, the amorphous phase of the catalyst is from 65 wt. % to 75 wt. %.

In some embodiments, the catalyst is characterized by having XRD diffraction peaks (2θ degrees) at least at 23.5±0.5, 25.6±0.5, and 27.1±0.7, wherein the XRD is obtained using CuKα radiation.

In some embodiments, the catalyst is characterized by having XRD diffraction peaks (2θ degrees) at least at 12.7±0.3, 23.5±0.5, 25.7±0.3, and 27.1±0.7, wherein the XRD is obtained using CuKα radiation.

In some embodiments, the catalyst has a 35% conversion temperature from about 320° C. to about 400° C.

In some embodiments, the catalyst has a selectivity to ethylene from 70% to 95%.

In some embodiments, the catalyst has a selectivity to ethylene from 80% to 85%.

In some embodiments, the catalyst is prepared by a method that includes providing an aqueous mixture including molybdenum and vanadium, hydrothermally reacting the mixture to form a precalcined catalyst, air calcining the precalcined catalyst to form the catalyst, and washing the catalyst with an acid solution.

In some embodiments, providing the aqueous mixture including molybdenum and vanadium includes combining an aqueous mixture including molybdenum and an aqueous mixture including vanadium. In some embodiments, the aqueous mixture including molybdenum is prepared from at least $(NH_4)_6Mo_7O_{24} \cdot 4H_2O$ and a first water. In some embodiments, the aqueous mixture including vanadium is prepared from at least $VOSO_4 \cdot XH_2O$ and a second water. In some embodiments, the first and the second water are selected from distilled water, deionized water, demineralized water, mineral water, or a combination thereof. In some embodiments, the first and second water include distilled water.

In some embodiments, the aqueous mixture including molybdenum and vanadium further includes a surfactant. In some embodiments, the surfactant is selected from a nonionic surfactant, an anionic surfactant, a cationic surfactant, or a combination thereof. In some embodiments, the anionic surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof. In some embodiments, the anionic surfactant includes sodium dodecyl sulfate. In some embodiments, the anionic surfactant includes sodium octyl sulfate.

In some embodiments, hydrothermally reacting the mixture to form the precalcined catalyst includes heating the aqueous mixture of molybdenum and vanadium in the presence of a catalyst seed.

In some embodiments, the catalyst seed includes a composition including molybdenum and vanadium. In some embodiments, the composition including molybdenum and vanadium includes a catalyst including molybdenum, vanadium, and oxygen, wherein the molar ratio of molybdenum to vanadium in the catalyst is from 1:0.15 to 1:0.75.

In some embodiments, the catalyst seed includes a composition including molybdenum, vanadium, niobium, and tellurium. In some embodiments, the composition including molybdenum, vanadium, niobium, and tellurium includes a catalyst including molybdenum, vanadium, tellurium, niobium, and oxygen, wherein In some embodiments, the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40 and wherein oxygen is present at least in an amount to satisfy the valency of any present metal oxides.

In some embodiments, hydrothermally reacting the mixture to form a precalcined catalyst includes heating the aqueous mixture of molybdenum and vanadium at a temperature from about 150° C. to about 300° C.

In some embodiments, hydrothermally reacting the mixture to form a precalcined catalyst includes heating the aqueous mixture of molybdenum and vanadium at a temperature from about 200° C. to about 250° C.

In some embodiments, hydrothermally reacting the mixture to form a precalcined catalyst includes heating the aqueous mixture of molybdenum and vanadium at a temperature from about 230° C.

In some embodiments, hydrothermally reacting the mixture to form a precalcined catalyst includes heating the aqueous mixture of molybdenum and vanadium under a pressure from about 1 psi to about 1,500 psi.

In some embodiments, hydrothermally reacting the mixture to form a precalcined catalyst includes heating the aqueous mixture of molybdenum and vanadium under a pressure from about 400 psi to about 440 psi.

In some embodiments, hydrothermally reacting the mixture to form a precalcined catalyst includes heating the aqueous mixture of molybdenum and vanadium at a temperature from about 200° C. to about 250° C. under a pressure from about 200 psi to about 900 psi.

In some embodiments, hydrothermally reacting the mixture to form a precalcined catalyst includes heating the aqueous mixture of molybdenum and vanadium at a temperature of about 230° C. under a pressure from about 400 psi to about 440 psi.

In some embodiments, hydrothermally reacting the mixture to form a precalcined catalyst includes contacting the mixture with a glass liner, stainless steel, or Teflon liner. In some embodiments, hydrothermally reacting the mixture to form a precalcined catalyst includes contacting the mixture with a glass liner. In some embodiments, hydrothermally reacting the mixture to form a precalcined catalyst includes contacting the mixture with a Teflon liner.

In some embodiments, the precalcined catalyst is calcined at about 300° C. to about 500° C.

In some embodiments, the precalcined catalyst is calcined at about 375° C. to about 425° C.

In some embodiments, the precalcined catalyst is calcined at about 400° C.

In some embodiments, the precalcined catalyst is calcined at about 300° C. to about 500° C. for about 1 hour to about 24 hours.

In some embodiments, the precalcined catalyst is calcined at about 375° C. to about 425° C. for about 1 hour to about 4 hours.

In some embodiments, the precalcined catalyst is calcined at about 400° C. for about 2 hours.

In some embodiments, the acid solution includes oxalic acid. In some embodiments, the concentration of oxalic acid is from about 0.05 M to about 0.5 M.

Also provided in this disclosure is an oxidative dehydrogenation catalyst including molybdenum, vanadium, and oxygen, wherein the molar ratio of molybdenum to vanadium in the catalyst is from 1:0.30 to 1:0.70, and oxygen is present in the catalyst at least in amount to satisfy the valency of any present metal oxides In some embodiments, the amorphous phase of the catalyst is greater than 55 wt. %.

In some embodiments, the molar ratio of molybdenum to vanadium in the catalyst is from 1:0.35 to 1:0.65.

In some embodiments, the molar ratio of molybdenum to vanadium in the catalyst is from 1:0.40 to 1:0.60.

In some embodiments, the amorphous phase of the catalyst is from 55 wt. % to 75 wt. %.

In some embodiments, the amorphous phase of the catalyst is from 56 wt. % to 66 wt. %.

In some embodiments, the catalyst is characterized by having XRD diffraction peaks (2θ degrees) at least at 26.3±0.3 and 29.4±0.3, wherein the XRD is obtained using CuKα radiation.

In some embodiments, the catalyst is characterized by having XRD diffraction peaks (2θ degrees) at least at 22.3±0.4, 25.0±0.2, 26.2±0.2, 29.4±0.3, 32.6±0.2, and 33.4±0.2, wherein the XRD is obtained using CuKα radiation.

In some embodiments, the catalyst has a 35% conversion temperature from about 300° C. to about 425° C.

In some embodiments, the catalyst has a selectivity to ethylene from 65% to 95%.

In some embodiments, the catalyst is prepared by a method that includes providing an aqueous mixture including molybdenum and vanadium, hydrothermally reacting the mixture to form a precalcined catalyst, and calcining the precalcined catalyst under a nitrogen atmosphere to form the catalyst.

In some embodiments, providing the aqueous mixture including molybdenum and vanadium includes combining an aqueous mixture including molybdenum and an aqueous mixture including vanadium. In some embodiments, the aqueous mixture including molybdenum is prepared from at least $(NH_4)_6Mo_7O_{24} \cdot 4H_2O$ and a first water. In some embodiments, the aqueous mixture including vanadium is prepared from at least $VOSO_4 \cdot XH_2O$ and a second water. In some embodiments, the first and the second water are selected from distilled water, deionized water, demineralized water, mineral water, or a combination thereof. In some embodiments, the first and second water include distilled water.

In some embodiments, the aqueous mixture including molybdenum and vanadium further includes a surfactant. In some embodiments, the surfactant is selected from a nonionic surfactant, an anionic surfactant, a cationic surfactant, or a combination thereof. In some embodiments, the anionic surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof. In some embodiments, the anionic surfactant includes sodium dodecyl sulfate. In some embodiments, the anionic surfactant includes sodium octyl sulfate.

In some embodiments, hydrothermally reacting the mixture to form the precalcined catalyst includes heating the aqueous mixture of molybdenum and vanadium in the presence of a catalyst seed.

In some embodiments, the catalyst seed includes a composition including molybdenum and vanadium. In some embodiments, the composition including molybdenum and vanadium includes a catalyst including molybdenum, vanadium, and oxygen, wherein the molar ratio of molybdenum to vanadium in the catalyst is from 1:0.15 to 1:0.75.

In some embodiments, the catalyst seed includes a composition including molybdenum, vanadium, niobium, and tellurium. In some embodiments, the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40, and wherein oxygen is present at least in an amount to satisfy the valency of any present metal oxides.

In some embodiments, hydrothermally reacting the mixture to form a precalcined catalyst includes heating the aqueous mixture of molybdenum and vanadium at a temperature from about 150° C. to about 300° C.

In some embodiments, hydrothermally reacting the mixture to form a precalcined catalyst includes heating the aqueous mixture of molybdenum and vanadium at a temperature from about 200° C. to about 250° C.

In some embodiments, hydrothermally reacting the mixture to form a precalcined catalyst includes heating the aqueous mixture of molybdenum and vanadium at a temperature of about 230° C.

In some embodiments, hydrothermally reacting the mixture to form a precalcined catalyst includes heating the aqueous mixture of molybdenum and vanadium under a pressure from about 1 psi to about 1,500 psi.

In some embodiments, hydrothermally reacting the mixture to form a precalcined catalyst includes heating the aqueous mixture of molybdenum and vanadium under a pressure from about 400 psi to about 440 psi.

In some embodiments, hydrothermally reacting the mixture to form a precalcined catalyst includes heating the aqueous mixture of molybdenum and vanadium at a temperature from about 200° C. to about 250° C. under a pressure from about 200 psi to about 900 psi.

In some embodiments, wherein hydrothermally reacting the mixture to form a precalcined catalyst includes heating the aqueous mixture of molybdenum and vanadium at a temperature of about 230° C. under a pressure from about 400 psi to about 440 psi.

In some embodiments, hydrothermally reacting the mixture to form a precalcined catalyst includes contacting the mixture with a glass liner, stainless steel, or Teflon liner. In some embodiments, hydrothermally reacting the mixture to form a precalcined catalyst includes contacting the mixture with a glass liner. In some embodiments, hydrothermally reacting the mixture to form a precalcined catalyst includes contacting the mixture with a Teflon liner.

In some embodiments, the precalcined catalyst is calcined at about 300° C. to about 500° C.

In some embodiments, the precalcined catalyst is calcined at about 375° C. to about 425° C.

In some embodiments, the precalcined catalyst is calcined at about 400° C.

In some embodiments, the precalcined catalyst is calcined at about 300° C. to about 500° C. for about 1 hour to about 24 hours.

In some embodiments, the precalcined catalyst is calcined at about 375° C. to about 425° C. for about 1 hour to about 4 hours.

In some embodiments, the precalcined catalyst is calcined at about 400° C. for about 2 hours.

Also provided in this disclosure is an oxidative dehydrogenation catalyst that includes molybdenum, vanadium, and oxygen, wherein the molar ratio of molybdenum to vanadium in the catalyst is from 1:0.30 to 1:0.50, oxygen is present in the catalyst at least in amount to satisfy the valency of any present metal oxides, and the amorphous phase of the catalyst is greater than 45 wt. %. The catalyst is prepared by a method that includes providing an aqueous mixture including molybdenum and vanadium, hydrothermally reacting the mixture to form a precalcined catalyst, calcining the precalcined catalyst under a nitrogen atmosphere to form the catalyst, and washing the catalyst with an acid solution.

In some embodiments, the molar ratio of molybdenum to vanadium in the catalyst is from 1:0.35 to 1:0.45.

In some embodiments, the molar ratio of molybdenum to vanadium in the catalyst is about 1:0.41.

In some embodiments, the amorphous phase of the catalyst is from 45 wt. % to 75 wt. %.

In some embodiments, the amorphous phase of the catalyst is from 45 wt. % to 55 wt. %.

In some embodiments, the catalyst is characterized by having XRD diffraction peaks (2θ degrees) at least at 26.3±0.3 and 29.4±0.3, wherein the XRD is obtained using CuKα radiation.

In some embodiments, the catalyst is characterized by having XRD diffraction peaks (2θ degrees) at least at 25.4±0.2, 26.3±0.3, 25.6±0.2, 28.3±0.3, 29.3±0.2, 30.6±0.3, and 31.9±0.2, wherein the XRD is obtained using CuKα radiation.

In some embodiments, the catalyst is characterized by having XRD diffraction peaks (2θ degrees) at least at 6.5±0.3, 7.8±0.2, 9.0±0.2, 10.8±0.2, 12.9±0.3, 13.4±0.2, 25.4±0.2, 26.3±0.3, 25.6±0.2, 28.3±0.3, 29.3±0.2, 29.8±0.2, 30.6±0.3, 31.5±0.3, 31.9±0.2, 34.2±0.3, and 35.4±0.3, wherein the XRD is obtained using CuKα radiation.

In some embodiments, the catalyst has a 35% conversion temperature from about 350° C. to about 425° C.

In some embodiments, providing the aqueous mixture including molybdenum and vanadium includes combining an aqueous mixture including molybdenum and an aqueous mixture including vanadium. In some embodiments, the aqueous mixture including molybdenum is prepared from at least $(NH_4)_6Mo_7O_{24} \cdot 4H_2O$ and a first water. In some embodiments, the aqueous mixture including vanadium is prepared from at least $VOSO_4 \cdot XH_2O$ and a second water. In some embodiments, the first and the second water are selected from distilled water, deionized water, demineralized water, mineral water, or a combination thereof. In some embodiments, the first and second water include distilled water.

In some embodiments, the aqueous mixture including molybdenum and vanadium further includes a surfactant. In some embodiments, the surfactant is selected from a non-ionic surfactant, an anionic surfactant, a cationic surfactant, or a combination thereof. In some embodiments, the anionic surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof. In some embodiments, the anionic surfactant includes sodium dodecyl sulfate. In some embodiments, the anionic surfactant includes sodium octyl sulfate.

In some embodiments, hydrothermally reacting the mixture to form the precalcined catalyst includes heating the aqueous mixture of molybdenum and vanadium in the presence of a catalyst seed.

In some embodiments, the catalyst seed includes a composition including molybdenum and vanadium. In some embodiments, the composition including molybdenum and vanadium includes a catalyst including molybdenum, vanadium, and oxygen, wherein the molar ratio of molybdenum to vanadium in the catalyst is from 1:0.15 to 1:0.75.

In some embodiments, the catalyst seed includes a composition including molybdenum, vanadium, niobium, and tellurium. In some embodiments, the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40, and wherein oxygen is present at least in an amount to satisfy the valency of any present metal oxides.

In some embodiments, hydrothermally reacting the mixture to form a precalcined catalyst includes heating the aqueous mixture of molybdenum and vanadium at a temperature from about 150° C. to about 300° C.

In some embodiments, hydrothermally reacting the mixture to form a precalcined catalyst includes heating the aqueous mixture of molybdenum and vanadium at a temperature from about 200° C. to about 250° C.

In some embodiments, hydrothermally reacting the mixture to form a precalcined catalyst includes heating the aqueous mixture of molybdenum and vanadium at a temperature of about 230° C.

In some embodiments, hydrothermally reacting the mixture to form a precalcined catalyst includes heating the aqueous mixture of molybdenum and vanadium under a pressure from about 1 psi to about 1,500 psi.

In some embodiments, hydrothermally reacting the mixture to form a precalcined catalyst includes heating the aqueous mixture of molybdenum and vanadium under a pressure from about 400 psi to about 440 psi.

In some embodiments, hydrothermally reacting the mixture to form a precalcined catalyst includes heating the aqueous mixture of molybdenum and vanadium at a temperature from about 200° C. to about 250° C. under a pressure from about 200 psi to about 900 psi.

In some embodiments, hydrothermally reacting the mixture to form a precalcined catalyst includes heating the aqueous mixture of molybdenum and vanadium at a temperature of about 230° C. under a pressure from about 400 psi to about 440 psi.

In some embodiments, hydrothermally reacting the mixture to form a precalcined catalyst includes contacting the mixture with a glass liner, stainless steel, or Teflon liner. In some embodiments, hydrothermally reacting the mixture to form a precalcined catalyst includes contacting the mixture with a glass liner. In some embodiments, hydrothermally reacting the mixture to form a precalcined catalyst includes contacting the mixture with a Teflon liner.

In some embodiments, the precalcined catalyst is calcined at about 300° C. to about 500° C.

In some embodiments, the precalcined catalyst is calcined at about 375° C. to about 425° C.

In some embodiments, the precalcined catalyst is calcined at about 400° C.

In some embodiments, the precalcined catalyst is calcined at about 300° C. to about 500° C. for about 1 hour to about 24 hours.

In some embodiments, the precalcined catalyst is calcined at about 375° C. to about 425° C. for about 1 hour to about 4 hours.

In some embodiments, the precalcined catalyst is calcined at about 400° C. for about 2 hours.

In some embodiments, the acid solution includes oxalic acid. In some embodiments, the concentration of oxalic acid is from about 0.05 M to about 0.5 M.

Also provided in this disclosure is a method for the oxidative dehydrogenation of ethane to ethylene. The method includes contacting, in an oxidative dehydrogenation reactor, ethane and oxygen with any oxidative dehydrogenation catalyst disclosed herein.

In some embodiments, ethane and oxygen are combined with inert diluent.

DETAILED DESCRIPTION

Figure 1:
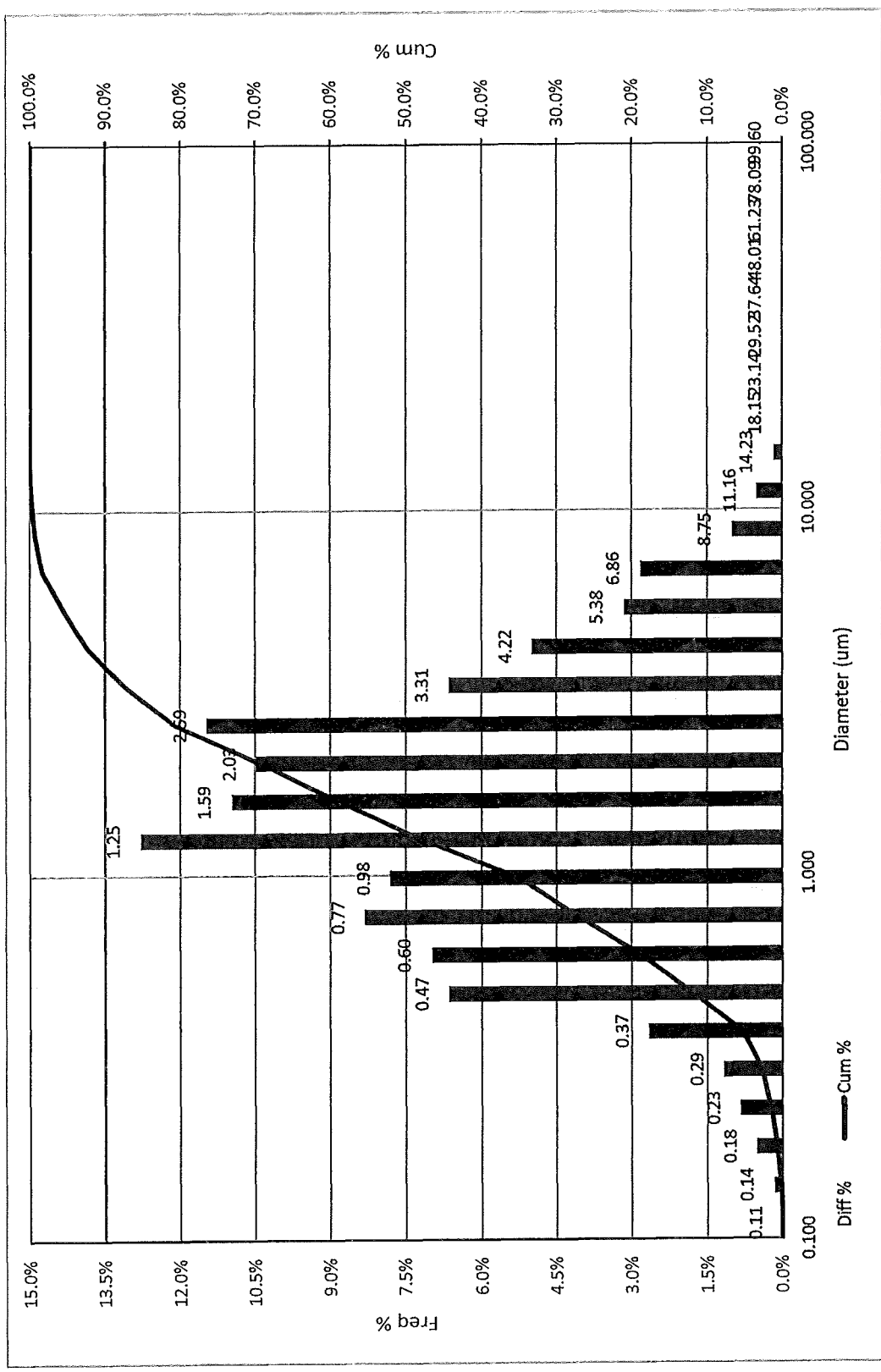
FIG. 1 shows the particle size graph for Catalyst 1.2.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used in this disclosure can allow for a degree of variability in a value or range, for example, within 10%, within 5%, or within 1% of a stated value or of a stated limit of a range.

The term "substantially" as used in this disclosure refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "room temperature" as used in this disclosure refers to a temperature from about 15° C. to about 28° C.

Provided in this disclosure is an oxidative dehydrogenation catalyst that includes molybdenum, vanadium, and oxygen. The molar ratio of molybdenum to vanadium in the catalyst is from 1:0.15 to 1:0.75. Oxygen is present in the catalyst at least in an amount to satisfy the valency of any present metal oxides.

In some embodiments, the amorphous phase of the catalyst is greater than 55 wt. %.

Unless stated otherwise, the molar ratio of molybdenum to vanadium for the catalysts provided in this disclosure is determined by inductively coupled plasma mass spectrometry (ICP-MS). For example, the molar ratio of molybdenum to vanadium for the catalysts can be determined as described in the Examples Section. One of ordinary skill in the art will recognize that additional methods can be used to determine the molar ratio of molybdenum to vanadium for the oxidative dehydrogenation catalysts disclosed herein and that when other methods are employed the observed ratio of molybdenum to vanadium may vary compared to when ICP-MS is employed. These additional methods include, but are not limited to, particle-induced X-ray emission (PIXE), X-ray fluorescence (XRF), and neutron activation analysis (NAA).

Unless stated otherwise, the weight percentage of amorphous phase in the oxidative dehydrogenation catalysts described herein is determined by X-ray diffraction (XRD) using Method A described in the Examples Section. Method A is used to fit the MoVOx orthorhombic phase (also referred to in literature as the M1 phase) using the literature crystal structure reference 04-022-1665 or the literature crystal structure references 04-022-1665 and 04-022-1664 in HighScore Plus XRD analysis software. Both 04-022-1665 and 04-022-1664 can be used to quantify the weight percentage of crystalline MoVOx orthorhombic phase when the sample has a combination of reflections that match best with both structure references used for fitting. The K-factor approach, as described by O'Connor and Raven (1988, Powder Diffraction, 3 (1), 2-6) is then used to measure the weight percentage of the crystalline phases, such that the weight percentage of the amorphous content can be assigned. The Degree of Crystallinity (DOC) method is then applied to determine the amount of amorphous phase. The DOC method assigns the total intensity of area contributed to the overall diffraction pattern by each component in the analysis as total crystalline content, and the difference in expected signal (as determined by external standard via K-factor approach) is the amount (i.e. wt. %) of amorphous phase.

In some embodiments, the molar ratio of molybdenum to vanadium in the catalyst is from 1:0.20 to 1:0.70. For example, the molar ratio of molybdenum to vanadium in the catalyst can be from 1:0.25 to 1:0.65, from 1:0.29 to 1:0.59, or from 1:0.32 to 1:0.38.

In some embodiments, the molar ratio of molybdenum to vanadium in the catalyst is from 1:0.36 to 1:0.43.

In some embodiments, the molar ratio of molybdenum to vanadium in the catalyst is from 1:0.37 to 1:0.44.

In some embodiments, the molar ratio of molybdenum to vanadium in the catalyst is from 1:0.41 to 1:0.48. For example, the molar ratio of molybdenum to vanadium in the catalyst can be from 1:0.42 to 1:0.46.

In some embodiments, the molar ratio of molybdenum to vanadium in the catalyst is from 1:0.44 to 1:0.52.

In some embodiments, the molar ratio of molybdenum to vanadium in the catalyst is from 1:0.45 to 1:0.54.

In some embodiments, the molar ratio of molybdenum to vanadium in the catalyst is from 1:0.50 to 1:0.59.

In some embodiments, the amorphous phase of the catalyst is from 55 wt. % to 80 wt. %. For example, the amorphous phase of catalyst can be from 55 wt. % to 75 wt. %.

The oxidative dehydrogenation catalyst can have a 35% conversion temperature from about 300° C. to about 400° C. The 35% conversion temperature of an oxidative dehydrogenation catalyst can be determined as described in the Examples Section. In some embodiments, the oxidative dehydrogenation catalyst has a 35% conversion temperature from about 310° C. to about 385° C. For example, the catalyst can have a 35% conversion temperature from about 310° C. to about 375° C. In some embodiments, the catalyst has a 35% conversion temperature from about 360° C. to about 380° C. For example, the oxidative dehydrogenation catalyst can have a 35% conversion temperature of about 360° C., 365° C., 370° C., 375° C., or about, 380° C. In some embodiments, the catalyst has a 35% conversion temperature from about 310° C. to about 330° C. In some embodiments, the oxidative dehydrogenation catalyst has a 35% conversion temperature from about 300° C. to about 340° C., about 310° C. to about 330° C., or from about 315° C. to about 325° C. For example, the oxidative dehydrogenation catalyst can have a 35% conversion temperature of about 300° C., 310° C., 320° C., 330° C., or about 340° C.

The oxidative dehydrogenation catalyst can have a selectivity to ethylene from 65% to 99%. As used in this disclosure, the phrase "selectivity to ethylene" refers to the percentage on a molar basis of converted or reacted ethane that forms ethylene. The selectivity to ethylene can be determined as described in the Examples Section. In some embodiments, the oxidative dehydrogenation catalyst can have a selectivity to ethylene of about 70%, 75%, 80%, or about 85%. In some embodiments, the oxidative dehydrogenation catalyst has a selectivity to ethylene from 75% to about 99%, about 75% to about 95%, or about 80% to 90%. For example, the oxidative dehydrogenation catalyst can have a selectivity to ethylene of about 75%, 80%, 85%, 90%, or about 95%.

In some embodiments, the catalyst has a 35% conversion temperature from about 310° C. to about 385° C. and a selectivity to ethylene from about 75% to about 90%. For example, the catalyst can have a 35% conversion temperature from about 360° C. to about 380° C. and a selectivity to ethylene from 75% to 80%.

In some embodiments, the oxidative dehydrogenation catalyst has a 35% conversion temperature from about 350° C. to about 390° C. and a selectivity to ethylene from 75% to 85%. For example, the oxidative dehydrogenation catalyst can have a 35% conversion temperature from about 360° C. to about 380° C. and a selectivity to ethylene from 75% to 80%. In some embodiments, the oxidative dehydrogenation catalyst has a 35% conversion temperature from about 300° C. to about 340° C. and a selectivity to ethylene from 75% to 99%. For example, the oxidative dehydrogenation catalyst can have a 35% conversion temperature from about 310° C. to about 330° C. and a selectivity to ethylene from 80% to 90%.

The oxidative dehydrogenation catalyst can be characterized by having at least one or more XRD diffraction peaks (2θ degrees) chosen from 6.7±0.2, 8.0±0.3, 9.0±0.2, 22.2±0.2, 23.5±0.2, 25.5±0.3, 27.3±0.2, 30.6±0.2, 35.3±0.2, 38.9±0.2, 45.3±0.2, 46.2±0.2, 46.2±0.2, 48.7±0.2, 51.9±0.2, and 55.2±0.2, wherein the XRD is obtained using CuKα radiation.

The oxidative dehydrogenation catalyst can an average particle size of from about 0.5 μm to about 10 μm. For example, the oxidative dehydrogenation catalyst can have an average particle size of about 1 μm, about 2 μm, about 3 μm, about 4 μm, about 5 μm, about 6 μm, about 7 μm, about 8 μm, about 9 μm, or about 10 μm. In some embodiments, the oxidative dehydrogenation catalyst has an average particle size of from about 1 μm to about 6 μm.

The oxidative dehydrogenation catalyst can have a Brunauer-Emmett-Teller (BET) surface area of about 1 $m^2/g$ to about 50 $m^2/g$. For example, the catalyst can have a BET surface area of about 1 $m^2/g$ to about 20 $m^2/g$ or about 20 $m^2/g$ to about 40 $m^2/g$. In some embodiments, the catalyst has a BET surface area of about 1 $m^2/g$ to about 5 $m^2/g$, about 5 $m^2/g$ to about 10 $m^2/g$, about 10 $m^2/g$ to about 15 $m^2/g$, about 15 $m^2/g$ to about 20 $m^2/g$, about 20 $m^2/g$ to about 25 $m^2/g$, about 25 $m^2/g$ to about 30 $m^2/g$, about 30 $m^2/g$ to about 35 $m^2/g$, or about 35 $m^2/g$ to about 40 $m^2/g$.

The oxidative dehydrogenation catalyst can be prepared by a method that includes providing an aqueous mixture (e.g., a homogeneous or heterogeneous mixture) including molybdenum and vanadium, hydrothermally reacting the mixture to form a precalcined catalyst, and calcining the precalcined catalyst to form the catalyst.

Providing the aqueous mixture including molybdenum and vanadium can include combining an aqueous mixture including molybdenum and an aqueous mixture including vanadium. The aqueous mixture including molybdenum can be prepared from at least $(NH_4)_6Mo_7O_{24}.4H_2O$ and a first water. The aqueous mixture including vanadium can be prepared from at least $VOSO_4.XH_2O$ and a second water. The first and the second water can be chosen from distilled water, deionized water, demineralized water, mineral water, or a combination thereof. In some embodiments, the first and second water include distilled water.

In some embodiments, the molar ratio of molybdenum to vanadium in the aqueous mixture is from about 7:1 to about 7:5. For example, the molar ratio of $(NH_4)_6Mo_7O_{24}.4H_2O$ to $VOSO_4.XH_2O$ used to prepare the aqueous mixture can be from about 1:1 to about 1:5. In some embodiments, the molar ratio of molybdenum to vanadium in the aqueous mixture is from about 7:3. For example, the molar ratio of $(NH_4)_6Mo_7O_{24}.4H_2O$ to $VOSO_4.XH_2O$ used to prepare the aqueous mixture can be can be about 1:3.

In some embodiments, the aqueous mixture including molybdenum and vanadium further includes a surfactant. The surfactant can be added after the aqueous mixture including molybdenum and the aqueous mixture including vanadium are combined. The surfactant can be a non-ionic surfactant, an anionic surfactant, a cationic surfactant, or a combination thereof. In some embodiments, the surfactant is a non-ionic surfactant. For example, the surfactant can be methyl cellulose. In some embodiments, the surfactant is an anionic surfactant. The anionic surfactant can be selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof. In some embodiments, the aqueous mixture including molybdenum and vanadium further includes sodium octyl sulfate. In some embodiments, the aqueous mixture including molybdenum and vanadium further includes sodium dodecyl sulfate.

In some embodiments, hydrothermally reacting the mixture to form the precalcined catalyst includes heating the aqueous mixture of molybdenum and vanadium via a microwave.

In some embodiments, hydrothermally reacting the mixture to form the precalcined catalyst includes heating the aqueous mixture of molybdenum and vanadium in the presence of a catalyst seed.

In some embodiments, the catalyst seed is a composition that includes molybdenum and vanadium. For example, the catalyst seed can be an oxidative dehydrogenation catalyst described in this disclosure. In some embodiments, the catalyst seed is an oxidative dehydrogenation catalyst that includes molybdenum, vanadium, and oxygen, wherein the molar ratio of molybdenum to vanadium in the catalyst is from 1:0.15 to 1:0.75, oxygen is present in the catalyst at least in an amount to satisfy the valency of any present metal oxides, and the amorphous phase of the catalyst is greater than 55 wt. %.

In some embodiments, the catalyst seed is composition that includes molybdenum, vanadium, niobium, and tellurium. For example, the catalyst seed can be an oxidative dehydrogenation catalyst that includes molybdenum, vanadium, niobium, and tellurium. In some embodiments, the catalyst seed is an oxidative dehydrogenation catalyst that includes molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.12 to 1:0.49, the molar ratio of molybdenum to tellurium is from 1:0.01 to 1:0.30, and the molar ratio of molybdenum to niobium is from 1:0.01 to 1:0.30; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.20 to 1:0.45, the molar ratio of molybdenum to tellurium is from 1:0.05 to 1:0.25, and the molar ratio of molybdenum to tellurium is from 1:0.05 to 1:0.25; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.25 to 1:0.40, the molar ratio of molybdenum to tellurium is from 1:0.10 to 1:0.20, and the molar ratio of molybdenum to tellurium is from 1:0.10 to 1:0.20; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.30 to 1:0.35, the molar ratio of molybdenum to tellurium is from 1:0.13 to 1:0.17, and the molar ratio of molybdenum to tellurium is from 1:0.12 to 1:0.14; and wherein oxygen is present at least in an amount to satisfy the valency of any present metal oxides.

Hydrothermally reacting the aqueous mixture including molybdenum and vanadium to form a precalcined catalyst can include heating the aqueous mixture of molybdenum and vanadium to a temperature from about 150° C. to about 300° C., about 175° C. to about 275° C., or about 200° C. to about 250° C. For example, hydrothermally reacting the mixture to form the precalcined catalyst can include heating the aqueous mixture of molybdenum and vanadium at a temperature of about 230° C. Further, hydrothermally reacting the mixture to form the precalcined catalyst can include heating the aqueous mixture of molybdenum and vanadium under a pressure that is greater than the corresponding saturated water vapor pressure during the hydrothermal reaction. In some embodiments, hydrothermally reacting the mixture to form the precalcined catalyst includes heating the aqueous mixture of molybdenum and vanadium under a pressure from about 1 pounds per square inch (psi) to about 1,500 psi, about 700 psi to about 1,100 psi, or about 800 psi to about 1,000 psi. For example, hydrothermally reacting the mixture to form the precalcined catalyst can include heating the aqueous mixture of molybdenum and vanadium under a pressure of about 900 psi. In some embodiments, hydrothermally reacting the mixture to form the precalcined catalyst includes heating the aqueous mixture of molybdenum and vanadium under a pressure from about 400 psi to about 440 psi.

In some embodiments, hydrothermally reacting the mixture to form the precalcined catalyst includes heating the aqueous mixture of molybdenum and vanadium at a temperature from about 200° C. to about 250° C. under a pressure 100 psi to about 1,100 psi. For example, hydrothermally reacting the mixture to form the precalcined catalyst can include heating the aqueous mixture of molybdenum and vanadium at a temperature of about 230° C. under a pressure of about 200 psi to about 900 psi, such as about 400 psi to about 440 psi.

The method of preparing the oxidative dehydrogenation catalyst can also include contacting the aqueous mixture of molybdenum and vanadium with a surface selected from glass, stainless steel, or TEFLON® during the hydrothermal reaction. The glass, stainless steel, or TEFLON® surface can promote the formation of the oxidative dehydrogenation catalyst. For example, during the hydrothermal reaction, the aqueous mixture of molybdenum and vanadium can be contained with a glass liner, a stainless-steel liner, or a TEFLON® liner. In some embodiments, the method of forming the oxidative dehydrogenation catalyst includes contacting the aqueous mixture of molybdenum and vanadium with glass. For example, the aqueous mixture of molybdenum and vanadium can be contained by a glass liner during the hydrothermal reaction.

The process of calcining the precalcined catalyst can be carried out at a temperature from about 300° C. to about 500° C., about 350° C. to about 450° C., or about 375° C. to about 425° C. For example, the precalcined catalyst can be calcined at about 375° C., 385° C., 395° C., 405° C., 415° C., or about 425° C. In some embodiments, the precalcined catalyst is calcined at about 400° C.

In some embodiments, the precalcined catalyst is calcined at about 300° C. to about 500° C. for about 1 hour to about 24 hours. For example, the precalcined catalyst can be calcined at about 375° C. to about 425° C. for about 1 hour to about 4 hours. In some embodiments, the precalcined catalyst is calcined at about 400° C. for about 2 hours.

Also provided in this disclosure is an oxidative dehydrogenation catalyst that includes molybdenum, vanadium, and oxygen, wherein the molar ratio of molybdenum to vanadium in the catalyst is from 1:0.20 to 1:0.60, oxygen is present in the catalyst at least in amount to satisfy the valency of any present metal oxides, and the amorphous phase of the catalyst is greater than 55 wt. %.

In some embodiments, the molar ratio of molybdenum to vanadium in the catalyst is from 1:0.24 to 1:0.58. In some embodiments, the molar ratio of molybdenum to vanadium in the catalyst is from 1:0.29 to 1:0.53. For example, the molar ratio of molybdenum to vanadium can be about 1:0.29, about 1:0.32, about 1:0.35, about 1:0.38, about 1:0.41, about 1:0.44, about 1:0.47 about 1:0.50, or about 1:0.53.

In some embodiments, the amorphous phase of the catalyst is from 55 wt. % to 75 wt. %. For example, the amorphous phase of the catalyst can be from 60 wt. % to 75 wt. %. In some embodiments, the amorphous phase of the catalyst is from 60 wt. % to 65 wt. %, 65 wt. % to 70 wt. %, or from 70 to 75 wt. %.

The catalyst can have a 35% conversion temperature from about 300° C. to about 425° C. For example, the catalyst can have a 35% conversion temperature from about 325° C. to about 375° C., or from about 375° C. to about 425° C. In some embodiments, the catalyst has a 35% conversion temperature from about 300° C. to about 325° C., from about 325° C. to about 350° C., from about 350° C. to about 375° C., about 375° C. to about 400° C., or from about 400° C. to about 425° C.

The catalyst can have a selectivity to ethylene from about 65% to about 95%. For example, the catalyst can have a selectivity to ethylene from about 65% to about 70%, about 70% to about 75%, about 75% to about 80%, about 80% to about 85%, about 85% to about 90%, or about 90% to about 95%.

The oxidative dehydrogenation catalyst can be characterized by having XRD diffraction peaks (2θ degrees) at least at 23.5±0.5, 25.6±0.5, and 27.1±0.7, wherein the XRD is obtained using CuKα radiation. In some embodiments, the catalyst is characterized by having XRD diffraction peaks (2θ degrees) at least at 21.7±0.2, 23.5±0.5, 25.0±0.3, 25.6±0.3, and 27.1±0.7, wherein the XRD is obtained using CuKα radiation.

In some embodiments, the oxidative dehydrogenation catalyst is characterized by having at least one or more XRD diffraction peaks (2θ degrees) chosen from 6.7±0.2, 8.0±0.3, 9.0±0.2, 22.2±0.2, 23.5±0.2, 25.5±0.3, 27.3±0.2, 30.6±0.2, 35.3±0.2, 38.9±0.2, 45.3±0.2, 46.2±0.2, 46.2±0.2, 48.7±0.2, 51.9±0.2, and 55.2±0.2, wherein the XRD is obtained using CuKα radiation.

The oxidative dehydrogenation catalyst can an average particle size of from about 0.5 μm to about 10 μm. For example, the oxidative dehydrogenation catalyst can have an average particle size of about 1 μm, about 2 μm, about 3 μm, about 4 μm, about 5 μm, about 6 μm, about 7 μm, about 8 μm, about 9 μm, or about 10 μm. In some embodiments, the oxidative dehydrogenation catalyst has an average particle size of from about 1 μm to about 6 μm.

The oxidative dehydrogenation catalyst can have a Brunauer-Emmett-Teller (BET) surface area of about 1 $m^2/g$ to about 50 $m^2/g$. For example, the catalyst can have a BET surface area of about 1 $m^2/g$ to about 20 $m^2/g$ or about 20 $m^2/g$ to about 40 $m^2/g$. In some embodiments, the catalyst has a BET surface area of about 1 $m^2/g$ to about 5 $m^2/g$, about 5 $m^2/g$ to about 10 $m^2/g$, about 10 $m^2/g$ to about 15 $m^2/g$, about 15 $m^2/g$ to about 20 $m^2/g$, about 20 $m^2/g$ to about 25 $m^2/g$, about 25 $m^2/g$ to about 30 $m^2/g$, about 30 $m^2/g$ to about 35 $m^2/g$, or about 35 $m^2/g$ to about 40 $m^2/g$.

The oxidative dehydrogenation catalyst can be prepared by a method that includes providing an aqueous mixture including molybdenum and vanadium, hydrothermally reacting the mixture to form a precalcined catalyst, and calcining the precalcined catalyst in the presence of air to form the catalyst.

Calcining the precalcined catalyst in the presence of air to form the catalyst can include, for example, calcining the precalcined catalyst in a muffle furnace, a calciner or a rotary kiln.

Providing the aqueous mixture including molybdenum and vanadium can include combining an aqueous mixture including molybdenum and an aqueous mixture including vanadium. The aqueous mixture including molybdenum can be prepared from at least $(NH_4)_6Mo_7O_{24} \cdot 4H_2O$ and a first water. The aqueous mixture including vanadium can be prepared from at least $VOSO_4 \cdot XH_2O$ and a second water. The first and the second water can be chosen from distilled water, deionized water, demineralized water, mineral water, or a combination thereof. In some embodiments, the first and second water include distilled water.

In some embodiments, the molar ratio of molybdenum to vanadium in the aqueous mixture is from about 7:1 to about 7:5. For example, the molar ratio of $(NH_4)_6Mo_7O_{24} \cdot 4H_2O$ to $VOSO_4 \cdot XH_2O$ used to prepare the aqueous mixture can be from about 1:1 to about 1:5. In some embodiments, the molar ratio of molybdenum to vanadium in the aqueous mixture is from about 7:3. For example, the molar ratio of $(NH_4)_6Mo_7O_{24} \cdot 4H_2O$ to $VOSO_4 \cdot XH_2O$ used to prepare the aqueous mixture can be can be about 1:3.

In some embodiments, the aqueous mixture including molybdenum and vanadium further includes a surfactant. The surfactant can be added after the aqueous mixture including molybdenum and the aqueous mixture including vanadium are combined. The surfactant can be a non-ionic surfactant, an anionic surfactant, a cationic surfactant, or a combination thereof. In some embodiments, the aqueous mixture including molybdenum and vanadium further includes sodium octyl sulfate. In some embodiments, the aqueous mixture including molybdenum and vanadium further includes sodium dodecyl sulfate.

In some embodiments, hydrothermally reacting the mixture to form the precalcined catalyst includes heating the aqueous mixture of molybdenum and vanadium via a microwave.

In some embodiments, hydrothermally reacting the mixture to form the precalcined catalyst includes heating the aqueous mixture of molybdenum and vanadium in the presence of a catalyst seed.

In some embodiments, the catalyst seed is a composition that includes molybdenum and vanadium. For example, the catalyst seed can be an oxidative dehydrogenation catalyst described in this disclosure. In some embodiments, the catalyst seed is an oxidative dehydrogenation catalyst that includes molybdenum, vanadium, and oxygen, wherein the molar ratio of molybdenum to vanadium in the catalyst is from 1:0.15 to 1:0.75, oxygen is present in the catalyst at least in an amount to satisfy the valency of any present metal oxides, and the amorphous phase of the catalyst is greater than 55 wt. %.

In some embodiments, the catalyst seed is composition that includes molybdenum, vanadium, niobium, and tellurium. For example, the catalyst seed can be an oxidative dehydrogenation catalyst that includes molybdenum, vanadium, niobium, and tellurium. In some embodiments, the catalyst seed is an oxidative dehydrogenation catalyst that includes molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.12 to 1:0.49, the molar ratio of molybdenum to tellurium is from 1:0.01 to 1:0.30, and the molar ratio of molybdenum to niobium is from 1:0.01 to 1:0.30; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.20 to 1:0.45, the molar ratio of molybdenum to tellurium is from 1:0.05 to 1:0.25, and the molar ratio of molybdenum to tellurium is from 1:0.05 to 1:0.25; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.25 to 1:0.40, the molar ratio of molybdenum to tellurium is from 1:0.10 to 1:0.20, and the molar ratio of molybdenum to tellurium is from 1:0.10 to 1:0.20; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.30 to 1:0.35, the molar ratio of molybdenum to tellurium is from 1:0.13 to 1:0.17, and the molar ratio of molybdenum to tellurium is from 1:0.12 to 1:0.14; and wherein oxygen is present at least in an amount to satisfy the valency of any present metal oxides.

Hydrothermally reacting the aqueous mixture including molybdenum and vanadium to form a precalcined catalyst can include heating the aqueous mixture of molybdenum and vanadium to a temperature from about 150° C. to about 300° C., about 175° C. to about 275° C., or about 200° C. to about 250° C. For example, hydrothermally reacting the mixture to form the precalcined catalyst can include heating the aqueous mixture of molybdenum and vanadium at a temperature of about 230° C. Further, hydrothermally reacting the mixture to form the precalcined catalyst can include heating the aqueous mixture of molybdenum and vanadium under a pressure that is greater than the corresponding saturated water vapor pressure during the hydrothermal reaction. In some embodiments, hydrothermally reacting the mixture to form the precalcined catalyst includes heating the aqueous mixture of molybdenum and vanadium under a pressure from about 1 pounds per square inch (psi) to about 1,500 psi, about 700 psi to about 1,100 psi, or about 800 psi to about 1,000 psi. For example, hydrothermally reacting the mixture to form the precalcined catalyst can include heating the aqueous mixture of molybdenum and vanadium under a pressure of about 900 psi. In some embodiments, hydrothermally reacting the mixture to form the precalcined catalyst includes heating the aqueous mixture of molybdenum and vanadium under a pressure from about 400 psi to about 440 psi.

In some embodiments, hydrothermally reacting the mixture to form the precalcined catalyst includes heating the aqueous mixture of molybdenum and vanadium at a temperature from about 200° C. to about 250° C. under a pressure 100 psi to about 1,100 psi. For example, hydrothermally reacting the mixture to form the precalcined catalyst can include heating the aqueous mixture of molybdenum and vanadium at a temperature of about 230° C. under a pressure of about 200 psi to about 900 psi, such as about 400 psi to about 440 psi.

The method of preparing the oxidative dehydrogenation catalyst can also include contacting the aqueous mixture of molybdenum and vanadium with a surface selected from glass, stainless steel, or TEFLON® during the hydrothermal reaction. The glass, stainless steel, or TEFLON® surface can promote the formation of the oxidative dehydrogenation catalyst. For example, during the hydrothermal reaction, the aqueous mixture of molybdenum and vanadium can be contained with a glass liner, a stainless-steel liner, or a TEFLON® liner. In some embodiments, the method of forming the oxidative dehydrogenation catalyst includes contacting the aqueous mixture of molybdenum and vanadium with glass. For example, the aqueous mixture of molybdenum and vanadium can be contained by a glass liner during the hydrothermal reaction.

The process of calcining the precalcined catalyst can be carried out at a temperature from about 300° C. to about 500° C., about 350° C. to about 450° C., or about 375° C. to about 425° C. For example, the precalcined catalyst can be calcined at about 375° C., 385° C., 395° C., 405° C., 415° C., or about 425° C. In some embodiments, the precalcined catalyst is calcined at about 400° C.

In some embodiments, the precalcined catalyst is calcined at about 300° C. to about 500° C. for about 1 hour to about 24 hours. For example, the precalcined catalyst can be calcined at about 375° C. to about 425° C. for about 1 hour to about 4 hours. In some embodiments, the precalcined catalyst is calcined at about 400° C. for about 2 hours.

Also provided in this disclosure is an oxidative dehydrogenation catalyst that includes molybdenum, vanadium, and oxygen. The molar ratio of molybdenum to vanadium in the catalyst is from 1:0.35 to 1:0.55. Oxygen is present in the catalyst at least in an amount to satisfy the valency of any present metal oxides. The amorphous phase of the catalyst is from about 60 wt. % to about 65 wt. %.

In some embodiments, the molar ratio of molybdenum to vanadium in the catalyst is from 1:0.35 to 1:0.45. In some embodiments, the molar ratio of molybdenum to vanadium in the catalyst is from 1:0.35 to 1:0.45.

The oxidative dehydrogenation catalyst can be prepared by a method that includes providing an aqueous mixture including molybdenum and vanadium, hydrothermally reacting the mixture to form a precalcined catalyst, and calcining the precalcined catalyst in the presence of air to form the catalyst.

In some embodiments, the catalyst is characterized by having XRD diffraction peaks (2θ degrees) at least at 21.7±0.2, 23.5±0.5, 25.0±0.3, 25.6±0.3, and 27.1±0.7, wherein the XRD is obtained using CuKα radiation.

In some embodiments, the catalyst has a 35% conversion temperature from about 350° C. to about 425° C. and a selectivity to ethylene from about 70% to about 90%.

Also provided in this disclosure is an oxidative dehydrogenation catalyst including molybdenum, vanadium, and oxygen, wherein the molar ratio of molybdenum to vanadium in the catalyst is from 1:0.20 to 1:0.50, oxygen is present in the catalyst at least in amount to satisfy the valency of any present metal oxides, and the amorphous phase of the catalyst is greater than 55%.

In some embodiments, the molar ratio of molybdenum to vanadium in the catalyst is from 1:0.25 to 1:0.45. For example, the molar ratio of molybdenum to vanadium can be from 1:0.25 to 1:0.30, from 1:0.30 to 1:0.35, from 1:35 to 1:0.40, or from 1:0.40 to 1:0.45. In some embodiments, the molar ratio of molybdenum to vanadium in the catalyst is from 1:0.29 to 1:0.39.

In some embodiments, the amorphous phase of the catalyst is from 55 wt. % to 85 wt. %. For example, the amorphous phase of the catalyst can be from 55 wt. % to 60 wt. %, 60 wt. % to 65 wt. %, 65 wt. % to 70 wt. %, 70 wt. % to 75 wt. %, 75 wt. % to 80 wt. %, or from 80 wt. % to 85 wt. %. In some embodiments, the amorphous phase of the catalyst is from 65 wt. % to 75 wt. %.

The catalyst can have a 35% conversion temperature from about 320° C. to about 400° C. For example, the catalyst can have a 35% conversion temperature from about 320° C. to about 340° C., about 340° C. to about 360° C., about 360° C. to about 380° C., or from about 380° C. to about 400° C.

The catalyst can have a selectivity to ethylene from about 70% to 95%. For example, the catalyst can have a selectivity to ethylene from 80% to 85%.

The oxidative dehydrogenation catalyst can be characterized by having XRD diffraction peaks (2θ degrees) at least at 23.5±0.5, 25.6±0.5, and 27.1±0.7, wherein the XRD is obtained using CuKα radiation. In some embodiments, the catalyst is characterized by having XRD diffraction peaks (2θ degrees) at least at 12.7±0.3, 23.5±0.5, 25.7±0.3, and 27.1±0.7, wherein the XRD is obtained using CuKα radiation.

In some embodiments, the oxidative dehydrogenation catalyst is characterized by having at least one or more XRD diffraction peaks (2θ degrees) chosen from 6.7±0.2, 8.0±0.3, 9.0±0.2, 22.2±0.2, 23.5±0.2, 25.5±0.3, 27.3±0.2, 30.6±0.2, 35.3±0.2, 38.9±0.2, 45.3±0.2, 46.2±0.2, 46.2±0.2, 48.7±0.2, 51.9±0.2, and 55.2±0.2, wherein the XRD is obtained using CuKα radiation.

The oxidative dehydrogenation catalyst can an average particle size of from about 0.5 μm to about 10 μm. For example, the oxidative dehydrogenation catalyst can have an average particle size of about 1 μm, about 2 μm, about 3 μm, about 4 μm, about 5 μm, about 6 μm, about 7 μm, about 8 μm, about 9 μm, or about 10 μm. In some embodiments, the oxidative dehydrogenation catalyst has an average particle size of from about 0.5 μm to about 5 μm or about 1 μm to about 3 μm.

The oxidative dehydrogenation catalyst can have a Brunauer-Emmett-Teller (BET) surface area of about 1 m$^2$/g to about 50 m$^2$/g. For example, the catalyst can have a BET surface area of about 1 m$^2$/g to about 20 m$^2$/g or about 20 m$^2$/g to about 40 m$^2$/g. In some embodiments, the catalyst has a BET surface area of about 1 m$^2$/g to about 5 m$^2$/g, about 5 m$^2$/g to about 10 m$^2$/g, about 10 m$^2$/g to about 15 m$^2$/g, about 15 m$^2$/g to about 20 m$^2$/g, about 20 m$^2$/g to about 25 m$^2$/g, about 25 m$^2$/g to about 30 m$^2$/g, about 30 m$^2$/g to about 35 m$^2$/g, or about 35 m$^2$/g to about 40 m$^2$/g.

The oxidative dehydrogenation catalyst can be prepared by a method that includes providing an aqueous mixture including molybdenum and vanadium, hydrothermally reacting the mixture to form a precalcined catalyst, calcining the precalcined catalyst in the presence of air to form the catalyst, and washing the catalyst with an acid solution.

Providing the aqueous mixture including molybdenum and vanadium can include combining an aqueous mixture including molybdenum and an aqueous mixture including vanadium. The aqueous mixture including molybdenum can be prepared from at least $(NH_4)_6Mo_7O_{24}\cdot 4H_2O$ and a first water. The aqueous mixture including vanadium can be prepared from at least $VOSO_4\cdot XH_2O$ and a second water. The first and the second water can be chosen from distilled water, deionized water, demineralized water, mineral water, or a combination thereof. In some embodiments, the first and second water include distilled water.

In some embodiments, the molar ratio of molybdenum to vanadium in the aqueous mixture is from about 7:1 to about 7:5. For example, the molar ratio of $(NH_4)_6Mo_7O_{24}\cdot 4H_2O$ to $VOSO_4\cdot XH_2O$ used to prepare the aqueous mixture can be from about 1:1 to about 1:5. In some embodiments, the molar ratio of molybdenum to vanadium in the aqueous mixture is from about 7:3. For example, the molar ratio of $(NH_4)_6Mo_7O_{24}\cdot 4H_2O$ to $VOSO_4\cdot XH_2O$ used to prepare the aqueous mixture can be can be about 1:3.

In some embodiments, the aqueous mixture including molybdenum and vanadium further includes a surfactant. The surfactant can be added after the aqueous mixture including molybdenum and the aqueous mixture including vanadium are combined. The surfactant can be a non-ionic surfactant, an anionic surfactant, a cationic surfactant, or a combination thereof. In some embodiments, the aqueous mixture including molybdenum and vanadium further includes sodium octyl sulfate. In some embodiments, the aqueous mixture including molybdenum and vanadium further includes sodium dodecyl sulfate.

In some embodiments, hydrothermally reacting the mixture to form the precalcined catalyst includes heating the aqueous mixture of molybdenum and vanadium via a microwave.

In some embodiments, hydrothermally reacting the mixture to form the precalcined catalyst includes heating the aqueous mixture of molybdenum and vanadium in the presence of a catalyst seed.

In some embodiments, the catalyst seed is a composition that includes molybdenum and vanadium. For example, the catalyst seed can be an oxidative dehydrogenation catalyst described in this disclosure. In some embodiments, the catalyst seed is an oxidative dehydrogenation catalyst that includes molybdenum, vanadium, and oxygen, wherein the molar ratio of molybdenum to vanadium in the catalyst is from 1:0.15 to 1:0.75, oxygen is present in the catalyst at least in an amount to satisfy the valency of any present metal oxides, and the amorphous phase of the catalyst is greater than 55 wt. %.

In some embodiments, the catalyst seed is composition that includes molybdenum, vanadium, niobium, and tellurium. For example, the catalyst seed can be an oxidative dehydrogenation catalyst that includes molybdenum, vanadium, niobium, and tellurium. In some embodiments, the catalyst seed is an oxidative dehydrogenation catalyst that includes molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.12 to 1:0.49, the molar ratio of molybdenum to tellurium is from 1:0.01 to 1:0.30, and the molar ratio of molybdenum to niobium is from 1:0.01 to 1:0.30; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.20 to 1:0.45, the molar ratio of molybdenum to tellurium is from 1:0.05 to 1:0.25, and the molar ratio of molybdenum to tellurium is from 1:0.05 to 1:0.25; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.25 to 1:0.40, the molar ratio of molybdenum to tellurium is from 1:0.10 to 1:0.20, and the molar ratio of molybdenum to tellurium is from 1:0.10 to 1:0.20; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.30 to 1:0.35, the molar ratio of molybdenum to tellurium is from 1:0.13 to 1:0.17, and the molar ratio of molybdenum to tellurium is from 1:0.12 to 1:0.14; and wherein oxygen is present at least in an amount to satisfy the valency of any present metal oxides.

Hydrothermally reacting the aqueous mixture including molybdenum and vanadium to form a precalcined catalyst can include heating the aqueous mixture of molybdenum and vanadium to a temperature from about 150° C. to about 300° C., about 175° C. to about 275° C., or about 200° C. to about 250° C. For example, hydrothermally reacting the mixture to form the precalcined catalyst can include heating the aqueous mixture of molybdenum and vanadium at a temperature of about 230° C. Further, hydrothermally reacting the mixture to form the precalcined catalyst can include heating the aqueous mixture of molybdenum and vanadium under a pressure that is greater than the corresponding saturated water vapor pressure during the hydrothermal reaction. In some embodiments, hydrothermally reacting the mixture to form the precalcined catalyst includes heating the aqueous mixture of molybdenum and vanadium under a pressure from about 1 pounds per square inch (psi) to about 1,500 psi, about 700 psi to about 1,100 psi, or about 800 psi to about 1,000 psi. For example, hydrothermally reacting the mixture to form the precalcined catalyst can include heating the aqueous mixture of molybdenum and vanadium under a pressure of about 900 psi. In some embodiments, hydrothermally reacting the mixture to form the precalcined catalyst includes heating the aqueous mixture of molybdenum and vanadium under a pressure from about 400 psi to about 440 psi.

In some embodiments, hydrothermally reacting the mixture to form the precalcined catalyst includes heating the aqueous mixture of molybdenum and vanadium at a temperature from about 200° C. to about 250° C. under a pressure 100 psi to about 1,100 psi. For example, hydrothermally reacting the mixture to form the precalcined catalyst can include heating the aqueous mixture of molybdenum and vanadium at a temperature of about 230° C. under a pressure of about 200 psi to about 900 psi, such as about 400 psi to about 440 psi.

The method of preparing the oxidative dehydrogenation catalyst can also include contacting the aqueous mixture of molybdenum and vanadium with a surface selected from glass, stainless steel, or TEFLON® during the hydrothermal reaction. The glass, stainless steel, or TEFLON® surface can promote the formation of the oxidative dehydrogenation catalyst. For example, during the hydrothermal reaction, the aqueous mixture of molybdenum and vanadium can be contained with a glass liner, a stainless-steel liner, or a TEFLON® liner. In some embodiments, the method of forming the oxidative dehydrogenation catalyst includes contacting the aqueous mixture of molybdenum and vanadium with glass. For example, the aqueous mixture of molybdenum and vanadium can be contained by a glass liner during the hydrothermal reaction.

Calcining the precalcined catalyst in the presence of air to form the catalyst can include, for example, calcining the precalcined catalyst in a muffle furnace, a calciner or a rotary kiln.

The process of calcining the precalcined catalyst can be carried out at a temperature from about 300° C. to about 500° C., about 350° C. to about 450° C., or about 375° C. to about 425° C. For example, the precalcined catalyst can be calcined at about 375° C., 385° C., 395° C., 405° C., 415° C., or about 425° C. In some embodiments, the precalcined catalyst is calcined at about 400° C.

In some embodiments, the precalcined catalyst is calcined at about 300° C. to about 500° C. for about 1 hour to about 24 hours. For example, the precalcined catalyst can be calcined at about 375° C. to about 425° C. for about 1 hour to about 4 hours. In some embodiments, the precalcined catalyst is calcined at about 400° C. for about 2 hours.

In some embodiments, the acid solution used to wash the catalyst includes oxalic acid. The concentration of oxalic acid can be from about 0.05 molar (M) to about 0.5 M, about 0.1 M to about 0.36 M, or from about 0.15 M to about 0.3 M. In some embodiments, the concentration of oxalic acid is about 0.16 M or about 0.3 M.

Also provided in this disclosure is an oxidative dehydrogenation catalyst that includes molybdenum, vanadium, and oxygen. The molar ratio of molybdenum to vanadium in the catalyst is from 1:0.25 to 1:0.45. Oxygen is present in the catalyst at least in an amount to satisfy the valency of any present metal oxides. The amorphous phase of the catalyst is from about 65 wt. % to about 75 wt. %.

In some embodiments, the molar ratio of molybdenum to vanadium in the catalyst is from 1:0.25 to 1:0.35. In some embodiments, the molar ratio of molybdenum to vanadium in the catalyst is from 1:0.35 to 1:0.45.

The oxidative dehydrogenation catalyst can be prepared by a method that includes providing an aqueous mixture including molybdenum and vanadium, hydrothermally reacting the mixture to form a precalcined catalyst, calcining the precalcined catalyst in the presence of air to form the catalyst, and washing the catalyst with an oxalic acid solution having a concentration of oxalic acid from about 0.1 M to about 0.36 M. In some embodiments, the concentration of oxalic acid is from about 0.16 M to about 0.3 M.

In some embodiments, the catalyst is characterized by having XRD diffraction peaks (2θ degrees) at least at 12.7±0.3, 23.5±0.5, 25.7±0.3, and 27.1±0.7, wherein the XRD is obtained using CuKα radiation.

In some embodiments, the oxidative dehydrogenation catalyst is characterized by having at least one or more XRD diffraction peaks (2θ degrees) chosen from 6.7±0.2, 8.0±0.3, 9.0±0.2, 22.2±0.2, 23.5±0.2, 25.5±0.3, 27.3±0.2, 30.6±0.2, 35.3±0.2, 38.9±0.2, 45.3±0.2, 46.2±0.2, 46.2±0.2, 48.7±0.2, 51.9±0.2, and 55.2±0.2, wherein the XRD is obtained using CuKα radiation.

In some embodiments, the catalyst has a 35% conversion temperature from about 320° C. to about 380° C. and a selectivity to ethylene from about 75% to about 90%.

Also provided in this disclosure is an oxidative dehydrogenation catalyst that incudes molybdenum, vanadium, and oxygen, wherein the molar ratio of molybdenum to vanadium in the catalyst is from 1:0.30 to 1:0.70, and oxygen is present in the catalyst at least in amount to satisfy the valency of any present metal oxides.

In some embodiments, the amorphous phase of the catalyst is greater than 35% wt. %. In some embodiments, the amorphous phase of the catalyst is greater than 55% wt. %.

In some embodiments, the molar ratio of molybdenum to vanadium in the catalyst is from 1:0.35 to 1:0.65. For example, the molar ratio of molybdenum to vanadium in the catalyst can be from 1:0.40 to 1:0.60. In some embodiments, the molar ratio of molybdenum to vanadium in the catalyst is from 1:0.55 to 1:0.65.

In some embodiments, the amorphous phase of the catalyst is from 35 wt. % to 75 wt. %. In some embodiments, the amorphous phase of the catalyst is from 55 wt. % to 75 wt. %. For example, the amorphous phase of the catalyst can be from 56 wt. % to 66 wt. %.

The catalyst can have a 35% conversion temperature from about 300° C. to about 425° C. In some embodiments, the catalyst has a 35% conversion temperature from about 365° C. to about 405° C.

The catalyst can have a selectivity to ethylene from about 65% to about 95%. For example, the catalyst can have a selectivity to ethylene from about 65% to about 80%.

The oxidative dehydrogenation catalyst can be characterized by having XRD diffraction peaks (2θ degrees) at least at 26.3±0.3 and 29.4±0.3, wherein the XRD is obtained using CuKα radiation. In some embodiments, the catalyst is characterized by having XRD diffraction peaks (2θ degrees) at least at 22.3±0.4, 25.0±0.2, 26.2±0.2, 29.4±0.3, 32.6±0.2, and 33.4±0.2, wherein the XRD is obtained using CuKα radiation.

In some embodiments, the oxidative dehydrogenation catalyst is characterized by having at least one or more XRD diffraction peaks (2θ degrees) chosen from 6.7±0.2, 8.0±0.3, 9.0±0.2, 22.2±0.2, 23.5±0.2, 25.5±0.3, 27.3±0.2, 30.6±0.2, 35.3±0.2, 38.9±0.2, 45.3±0.2, 46.2±0.2, 46.2±0.2, 48.7±0.2, 51.9±0.2, and 55.2±0.2, wherein the XRD is obtained using CuKα radiation.

The oxidative dehydrogenation catalyst can an average particle size of from about 0.5 μm to about 10 μm. For example, the oxidative dehydrogenation catalyst can have an average particle size of about 1 μm, about 2 μm, about 3 μm, about 4 μm, about 5 μm, about 6 μm, about 7 μm, about 8 μm, about 9 μm, or about 10 μm. In some embodiments, the oxidative dehydrogenation catalyst has an average particle size of from about 0.5 μm to about 5 μm or about 1 μm to about 3 μm.

The oxidative dehydrogenation catalyst can have a Brunauer-Emmett-Teller (BET) surface area of about 1 $m^2/g$ to about 50 $m^2/g$. For example, the catalyst can have a BET surface area of about 1 $m^2/g$ to about 20 $m^2/g$ or about 20 $m^2/g$ to about 40 $m^2/g$. In some embodiments, the catalyst has a BET surface area of about 1 $m^2/g$ to about 5 $m^2/g$, about 5 $m^2/g$ to about 10 $m^2/g$, about 10 $m^2/g$ to about 15 $m^2/g$, about 15 $m^2/g$ to about 20 $m^2/g$, about 20 $m^2/g$ to about 25 $m^2/g$, about 25 $m^2/g$ to about 30 $m^2/g$, about 30 $m^2/g$ to about 35 $m^2/g$, or about 35 $m^2/g$ to about 40 $m^2/g$.

The oxidative dehydrogenation catalyst can be prepared by a method that includes providing an aqueous mixture including molybdenum and vanadium, hydrothermally reacting the mixture to form a precalcined catalyst, and calcining the precalcined catalyst under a nitrogen atmosphere to form the catalyst.

As used herein the term "nitrogen atmosphere" refers to an atmosphere that is greater than 95%, by volume, nitrogen. In some embodiments, calcining the precalcined catalyst under a nitrogen atmosphere includes calcining the precalcined catalyst under an atmosphere that is greater than 96%, 97%, 98%, 99%, 99.9% or greater than 99.999% nitrogen, by volume. In some embodiments, calcining the precalcined catalyst under a nitrogen atmosphere includes flowing the nitrogen atmosphere over the precalcined catalyst.

Providing the aqueous mixture including molybdenum and vanadium can include combining an aqueous mixture including molybdenum and an aqueous mixture including vanadium. The aqueous mixture including molybdenum can be prepared from at least $(NH_4)_6Mo_7O_{24} \cdot 4H_2O$ and a first water. The aqueous mixture including vanadium can be prepared from at least $VOSO_4 \cdot XH_2O$ and a second water. The first and the second water can be chosen from distilled water, deionized water, demineralized water, mineral water, or a combination thereof. In some embodiments, the first and second water include distilled water.

In some embodiments, the molar ratio of molybdenum to vanadium in the aqueous mixture is from about 7:1 to about 7:5. For example, the molar ratio of $(NH_4)_6Mo_7O_{24} \cdot 4H_2O$ to $VOSO_4 \cdot XH_2O$ used to prepare the aqueous mixture can be from about 1:1 to about 1:5. In some embodiments, the molar ratio of molybdenum to vanadium in the aqueous mixture is from about 7:3. For example, the molar ratio of $(NH_4)_6Mo_7O_{24} \cdot 4H_2O$ to $VOSO_4 \cdot XH_2O$ used to prepare the aqueous mixture can be can be about 1:3.

In some embodiments, the aqueous mixture including molybdenum and vanadium further includes a surfactant. The surfactant can be added after the aqueous mixture including molybdenum and the aqueous mixture including vanadium are combined. The surfactant can be a non-ionic surfactant, an anionic surfactant, a cationic surfactant, or a combination thereof. In some embodiments, the aqueous mixture including molybdenum and vanadium further includes sodium octyl sulfate. In some embodiments, the aqueous mixture including molybdenum and vanadium further includes sodium dodecyl sulfate.

In some embodiments, hydrothermally reacting the mixture to form the precalcined catalyst includes heating the aqueous mixture of molybdenum and vanadium via a microwave.

In some embodiments, hydrothermally reacting the mixture to form the precalcined catalyst includes heating the aqueous mixture of molybdenum and vanadium in the presence of a catalyst seed.

In some embodiments, the catalyst seed is a composition that includes molybdenum and vanadium. For example, the catalyst seed can be an oxidative dehydrogenation catalyst described in this disclosure. In some embodiments, the catalyst seed is an oxidative dehydrogenation catalyst that includes molybdenum, vanadium, and oxygen, wherein the molar ratio of molybdenum to vanadium in the catalyst is from 1:0.15 to 1:0.75, oxygen is present in the catalyst at least in an amount to satisfy the valency of any present metal oxides, and the amorphous phase of the catalyst is greater than 55 wt. %.

In some embodiments, the catalyst seed is composition that includes molybdenum, vanadium, niobium, and tellurium. For example, the catalyst seed can be an oxidative dehydrogenation catalyst that includes molybdenum, vanadium, niobium, and tellurium. In some embodiments, the catalyst seed is an oxidative dehydrogenation catalyst that includes molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.12 to 1:0.49, the molar ratio of molybdenum to tellurium is from 1:0.01 to 1:0.30, and the molar ratio of molybdenum to niobium is from 1:0.01 to 1:0.30; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.20 to 1:0.45, the molar ratio of molybdenum to tellurium is from 1:0.05 to 1:0.25, and the molar ratio of molybdenum to tellurium is from 1:0.05 to 1:0.25; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.25 to 1:0.40, the molar ratio of molybdenum to tellurium is from 1:0.10 to 1:0.20, and the molar ratio of molybdenum to tellurium is from 1:0.10 to 1:0.20; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.30 to 1:0.35, the molar ratio of molybdenum to tellurium is from 1:0.13 to 1:0.17, and the molar ratio of molybdenum to tellurium is from 1:0.12 to 1:0.14; and wherein oxygen is present at least in an amount to satisfy the valency of any present metal oxides.

Hydrothermally reacting the aqueous mixture including molybdenum and vanadium to form a precalcined catalyst can include heating the aqueous mixture of molybdenum and vanadium to a temperature from about 150° C. to about 300° C., about 175° C. to about 275° C., or about 200° C. to about 250° C. For example, hydrothermally reacting the mixture to form the precalcined catalyst can include heating the aqueous mixture of molybdenum and vanadium at a temperature of about 230° C. Further, hydrothermally reacting the mixture to form the precalcined catalyst can include heating the aqueous mixture of molybdenum and vanadium under a pressure that is greater than the corresponding saturated water vapor pressure during the hydrothermal reaction. In some embodiments, hydrothermally reacting the mixture to form the precalcined catalyst includes heating the aqueous mixture of molybdenum and vanadium under a pressure from about 1 psi to about 1,500 psi, about 700 psi to about 1,100 psi, or about 800 psi to about 1,000 psi. For example, hydrothermally reacting the mixture to form the precalcined catalyst can include heating the aqueous mixture of molybdenum and vanadium under a pressure of about 900 psi. In some embodiments, hydrothermally reacting the mixture to form the precalcined catalyst includes heating the aqueous mixture of molybdenum and vanadium under a pressure from about 400 psi to about 440 psi.

In some embodiments, hydrothermally reacting the mixture to form the precalcined catalyst includes heating the aqueous mixture of molybdenum and vanadium at a temperature from about 200° C. to about 250° C. under a pressure 100 psi to about 1,100 psi. For example, hydrothermally reacting the mixture to form the precalcined catalyst can include heating the aqueous mixture of molybdenum and vanadium at a temperature of about 230° C. under a pressure of about 200 psi to about 900 psi, such as about 400 psi to about 440 psi.

The method of preparing the oxidative dehydrogenation catalyst can also include contacting the aqueous mixture of molybdenum and vanadium with a surface selected from glass, stainless steel, or TEFLON® during the hydrothermal reaction. The glass, stainless steel, or TEFLON® surface can promote the formation of the oxidative dehydrogenation catalyst. For example, during the hydrothermal reaction, the aqueous mixture of molybdenum and vanadium can be contained with a glass liner, a stainless-steel liner, or a TEFLON® liner. In some embodiments, the method of forming the oxidative dehydrogenation catalyst includes contacting the aqueous mixture of molybdenum and vanadium with glass. For example, the aqueous mixture of molybdenum and vanadium can be contained by a glass liner during the hydrothermal reaction.

The process of calcining the precalcined catalyst can be carried out at a temperature from about 300° C. to about 500° C., about 350° C. to about 450° C., or about 375° C. to about 425° C. For example, the precalcined catalyst can be calcined at about 375° C., 385° C., 395° C., 405° C., 415° C., or about 425° C. In some embodiments, the precalcined catalyst is calcined at about 400° C.

In some embodiments, the precalcined catalyst is calcined at about 300° C. to about 500° C. for about 1 hour to about 24 hours. For example, the precalcined catalyst can be calcined at about 375° C. to about 425° C. for about 1 hour to about 4 hours. In some embodiments, the precalcined catalyst is calcined at about 400° C. for about 2 hours.

Also provided in this disclosure is an oxidative dehydrogenation catalyst that includes molybdenum, vanadium, and oxygen. The molar ratio of molybdenum to vanadium in the catalyst is from 1:0.50 to 1:070. Oxygen is present in the catalyst at least in an amount to satisfy the valency of any present metal oxides. The amorphous phase of the catalyst is from about 55 wt. % to about 70 wt. %.

In some embodiments, the molar ratio of molybdenum to vanadium in the catalyst is from 1:0.55 to 1:0.65. For example, the molar ratio of molybdenum to vanadium in the catalyst can be from 1:0.57 to 1:0.60.

The oxidative dehydrogenation catalyst can be prepared by a method that includes providing an aqueous mixture including molybdenum and vanadium, hydrothermally reacting the mixture to form a precalcined catalyst, and calcining the precalcined catalyst under a nitrogen atmosphere to form the catalyst.

The oxidative dehydrogenation catalyst can be characterized by having XRD diffraction peaks (2θ degrees) at least at 26.3±0.3 and 29.4±0.3, wherein the XRD is obtained using CuKα radiation. In some embodiments, the catalyst is characterized by having XRD diffraction peaks (2θ degrees) at least at 22.3±0.4, 25.0±0.2, 26.2±0.2, 29.4±0.3, 32.6±0.2, and 33.4±0.2, wherein the XRD is obtained using CuKα radiation.

In some embodiments, the catalyst has a 35% conversion temperature from about 370° C. to about 405° C. and a selectivity to ethylene from about 65% to about 85%. In some embodiments, the catalyst has a 35% conversion temperature from about 370° C. to about 380° C. and a selectivity to ethylene from about 75% to about 85%.

Also provided in this disclosure is an oxidative dehydrogenation catalyst including molybdenum, vanadium, and oxygen wherein the molar ratio of molybdenum to vanadium in the catalyst is from 1:0.30 to 1:0.50, oxygen is present in the catalyst at least in amount to satisfy the valency of any present metal oxides, and the amorphous phase of the catalyst is greater than 45 wt. %.

In some embodiments, the molar ratio of molybdenum to vanadium in the catalyst is from 1:0.35 to 1:0.45. For example, the molar ratio of molybdenum to vanadium in the catalyst can be about 1:0.41.

In some embodiments, the amorphous phase of the catalyst is from 45% wt. % to 75 wt. %. For example, the amorphous phase of the catalyst can be from 45 wt. % to 55 wt. %.

The catalyst can have a 35% conversion temperature from about 350° C. to about 425° C. For example, the catalyst can have a 35% conversion temperature from about 380° C. to about 400° C.

The oxidative dehydrogenation catalyst can be characterized by having XRD diffraction peaks (2θ degrees) at least at 26.3±0.3 and 29.4±0.3, wherein the XRD is obtained using CuKα radiation. In some embodiments, the catalyst is characterized by having XRD diffraction peaks (2θ degrees) at least at 25.4±0.2, 26.3±0.3, 25.6±0.2, 28.3±0.3, 29.3±0.2, 30.6±0.3, and 31.9±0.2, wherein the XRD is obtained using CuKα radiation. In some embodiments, the catalyst is characterized by having XRD diffraction peaks (2θ degrees) at least at 6.5±0.3, 7.8±0.2, 9.0±0.2, 10.8±0.2, 12.9±0.3, 13.4±0.2, 25.4±0.2, 26.3±0.3, 25.6±0.2, 28.3±0.3, 29.3±0.2, 29.8±0.2, 30.6±0.3, 31.5±0.3, 31.9±0.2, 34.2±0.3, and 35.4±0.3, wherein the XRD is obtained using CuKα radiation.

In some embodiments, the oxidative dehydrogenation catalyst is characterized by having at least one or more XRD diffraction peaks (2θ degrees) chosen from 6.7±0.2, 8.0±0.3, 9.0±0.2, 22.2±0.2, 23.5±0.2, 25.5±0.3, 27.3±0.2, 30.6±0.2, 35.3±0.2, 38.9±0.2, 45.3±0.2, 46.2±0.2, 46.2±0.2, 48.7±0.2, 51.9±0.2, and 55.2±0.2, wherein the XRD is obtained using CuKα radiation.

The oxidative dehydrogenation catalyst can have an average particle size of from about 0.5 μm to about 10 μm. For example, the oxidative dehydrogenation catalyst can have an average particle size of about 1 μm, about 2 μm, about 3 μm, about 4 μm, about 5 μm, about 6 μm, about 7 μm, about 8 μm, about 9 μm, or about 10 μm. In some embodiments, the oxidative dehydrogenation catalyst has an average particle size of from about 0.5 μm to about 5 μm or about 1 μm to about 3 μm.

The oxidative dehydrogenation catalyst can have a Brunauer-Emmett-Teller (BET) surface area of about 1 m$^2$/g to about 50 m$^2$/g. For example, the catalyst can have a BET surface area of about 1 m$^2$/g to about 20 m$^2$/g or about 20 m$^2$/g to about 40 m$^2$/g. In some embodiments, the catalyst has a BET surface area of about 1 m$^2$/g to about 5 m$^2$/g, about 5 m$^2$/g to about 10 m$^2$/g, about 10 m$^2$/g to about 15 m$^2$/g, about 15 m$^2$/g to about 20 m$^2$/g, about 20 m$^2$/g to about 25 m$^2$/g, about 25 m$^2$/g to about 30 m$^2$/g, about 30 m$^2$/g to about 35 m$^2$/g, or about 35 m$^2$/g to about 40 m$^2$/g.

The catalyst can be prepared by a method that includes providing an aqueous mixture including molybdenum and vanadium, hydrothermally reacting the mixture to form a precalcined catalyst, calcining the precalcined catalyst under a nitrogen atmosphere to form the catalyst, and washing the catalyst with an acid solution.

In some embodiments, calcining the precalcined catalyst under a nitrogen atmosphere includes calcining the precalcined catalyst under an atmosphere that is greater than 96%, 97%, 98%, 99%, 99.9% or greater than 99.999% nitrogen, by volume. In some embodiments, calcining the precalcined catalyst under a nitrogen atmosphere includes flowing the nitrogen atmosphere over the precalcined catalyst.

Providing the aqueous mixture including molybdenum and vanadium can include combining an aqueous mixture including molybdenum and an aqueous mixture including vanadium. The aqueous mixture including molybdenum can be prepared from at least $(NH_4)_6Mo_7O_{24}·4H_2O$ and a first water. The aqueous mixture including vanadium can be prepared from at least $VOSO_4·XH_2O$ and a second water. The first and the second water can be chosen from distilled water, deionized water, demineralized water, mineral water, or a combination thereof. In some embodiments, the first and second water include distilled water.

In some embodiments, the molar ratio of molybdenum to vanadium in the aqueous mixture is from about 7:1 to about 7:5. For example, the molar ratio of $(NH_4)_6Mo_7O_{24}·4H_2O$ to $VOSO_4·XH_2O$ used to prepare the aqueous mixture can be from about 1:1 to about 1:5. In some embodiments, the molar ratio of molybdenum to vanadium in the aqueous mixture is from about 7:3. For example, the molar ratio of $(NH_4)_6Mo_7O_{24}·4H_2O$ to $VOSO_4·XH_2O$ used to prepare the aqueous mixture can be can be about 1:3.

In some embodiments, the aqueous mixture including molybdenum and vanadium further includes a surfactant. The surfactant can be added after the aqueous mixture including molybdenum and the aqueous mixture including vanadium are combined. The surfactant can be a non-ionic surfactant, an anionic surfactant, a cationic surfactant, or a combination thereof. In some embodiments, the aqueous mixture including molybdenum and vanadium further includes sodium octyl sulfate. In some embodiments, the aqueous mixture including molybdenum and vanadium further includes sodium dodecyl sulfate.

In some embodiments, hydrothermally reacting the mixture to form the precalcined catalyst includes heating the aqueous mixture of molybdenum and vanadium via a microwave.

In some embodiments, hydrothermally reacting the mixture to form the precalcined catalyst includes heating the aqueous mixture of molybdenum and vanadium in the presence of a catalyst seed.

In some embodiments, the catalyst seed is a composition that includes molybdenum and vanadium. For example, the catalyst seed can be an oxidative dehydrogenation catalyst described in this disclosure. In some embodiments, the catalyst seed is an oxidative dehydrogenation catalyst that includes molybdenum, vanadium, and oxygen, wherein the molar ratio of molybdenum to vanadium in the catalyst is from 1:0.15 to 1:0.75, oxygen is present in the catalyst at least in an amount to satisfy the valency of any present metal oxides, and the amorphous phase of the catalyst is greater than 55 wt. %.

In some embodiments, the catalyst seed is a composition that includes molybdenum, vanadium, niobium, and tellurium. For example, the catalyst seed can be an oxidative dehydrogenation catalyst that includes molybdenum, vanadium, niobium, and tellurium. In some embodiments, the catalyst seed is an oxidative dehydrogenation catalyst that includes molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.12 to 1:0.49, the molar ratio of molybdenum to tellurium is from 1:0.01 to 1:0.30, and the molar ratio of molybdenum to niobium is from 1:0.01 to 1:0.30; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.20 to 1:0.45, the molar ratio of molybdenum to tellurium is from 1:0.05 to 1:0.25, and the molar ratio of molybdenum to tellurium is from 1:0.05 to 1:0.25; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.25 to 1:0.40, the molar ratio of molybdenum to tellurium is from 1:0.10 to 1:0.20, and the molar ratio of molybdenum to tellurium is from 1:0.10 to 1:0.20; and wherein oxygen is present at least in an amount to satisfy the valency of any present metal oxides. In some embodiments, the catalyst seed is an oxidative dehydrogenation catalyst that includes molybdenum, vanadium, tellurium, niobium, and oxygen, wherein the molar ratio of molybdenum to vanadium is from 1:0.30 to 1:0.35, the molar ratio of molybdenum to tellurium is from 1:0.13 to 1:0.17, and the molar ratio of molybdenum to tellurium is from 1:0.12 to 1:0.14; and wherein oxygen is present at least in an amount to satisfy the valency of any present metal oxides.

Hydrothermally reacting the aqueous mixture including molybdenum and vanadium to form a precalcined catalyst can include heating the aqueous mixture of molybdenum and vanadium to a temperature from about 150° C. to about 300° C., about 175° C. to about 275° C., or about 200° C. to about 250° C. For example, hydrothermally reacting the mixture to form the precalcined catalyst can include heating the aqueous mixture of molybdenum and vanadium at a temperature of about 230° C. Further, hydrothermally reacting the mixture to form the precalcined catalyst can include heating the aqueous mixture of molybdenum and vanadium under a pressure that is greater than the corresponding saturated water vapor pressure during the hydrothermal reaction. In some embodiments, hydrothermally reacting the mixture to form the precalcined catalyst includes heating the aqueous mixture of molybdenum and vanadium under a pressure from about 1 pounds per square inch (psi) to about 1,500 psi, about 700 psi to about 1,100 psi, or about 800 psi to about 1,000 psi. For example, hydrothermally reacting the mixture to form the precalcined catalyst can include heating the aqueous mixture of molybdenum and vanadium under a pressure of about 900 psi. In some embodiments, hydrothermally reacting the mixture to form the precalcined catalyst includes heating the aqueous mixture of molybdenum and vanadium under a pressure from about 400 psi to about 440 psi.

In some embodiments, hydrothermally reacting the mixture to form the precalcined catalyst includes heating the aqueous mixture of molybdenum and vanadium at a temperature from about 200° C. to about 250° C. under a pressure 100 psi to about 1,100 psi. For example, hydrothermally reacting the mixture to form the precalcined catalyst can include heating the aqueous mixture of molybdenum and vanadium at a temperature of about 230° C. under a pressure of about 200 psi to about 900 psi, such as about 400 psi to about 440 psi.

The method of preparing the oxidative dehydrogenation catalyst can also include contacting the aqueous mixture of molybdenum and vanadium with a surface selected from glass, stainless steel, or TEFLON® during the hydrothermal reaction. The glass, stainless steel, or TEFLON® surface can promote the formation of the oxidative dehydrogenation catalyst. For example, during the hydrothermal reaction, the aqueous mixture of molybdenum and vanadium can be contained with a glass liner, a stainless-steel liner, or a TEFLON® liner. In some embodiments, the method of forming the oxidative dehydrogenation catalyst includes contacting the aqueous mixture of molybdenum and vanadium with glass. For example, the aqueous mixture of molybdenum and vanadium can be contained by a glass liner during the hydrothermal reaction.

In some embodiments, calcining the precalcined catalyst under a nitrogen atmosphere includes calcining the precalcined catalyst under an atmosphere that is greater than 96%, 97%, 98%, 99%, or greater than 99.9% nitrogen, by volume.

The process of calcining the precalcined catalyst under a nitrogen atmosphere can be carried out at a temperature from about 300° C. to about 500° C., about 350° C. to about 450° C., or about 375° C. to about 425° C. For example, the precalcined catalyst can be calcined at about 375° C., 385° C., 395° C., 405° C., 415° C., or about 425° C. In some embodiments, the precalcined catalyst is calcined at about 400° C.

In some embodiments, the precalcined catalyst is calcined at about 300° C. to about 500° C. for about 1 hour to about 24 hours. For example, the precalcined catalyst can be calcined at about 375° C. to about 425° C. for about 1 hour to about 4 hours. In some embodiments, the precalcined catalyst is calcined at about 400° C. for about 2 hours.

In some embodiments, the acid solution used to wash the catalyst includes oxalic acid. The concentration of oxalic acid can be from about 0.05 molar (M) to about 0.05 M, about 0.1 M to about 0.36 M, or from about 0.15 M to about 0.3 M. In some embodiments, the concentration of oxalic acid is about 0.16 M or about 0.3 M.

Also provided in this disclosure is an oxidative dehydrogenation catalyst that includes molybdenum, vanadium, and oxygen. The molar ratio of molybdenum to vanadium in the catalyst is from 1:0.35 to 1:0.45. Oxygen is present in the catalyst at least in an amount to satisfy the valency of any present metal oxides. The amorphous phase of the catalyst is from about 45 wt. % to about 55 wt. %.

In some embodiments, the molar ratio of molybdenum to vanadium in the catalyst is from 1:0.39 to 1:0.43. In some embodiments, the molar ratio of molybdenum to vanadium in the catalyst is about 0.41.

The oxidative dehydrogenation catalyst can be prepared by a method that includes providing an aqueous mixture including molybdenum and vanadium, hydrothermally reacting the mixture to form a precalcined catalyst, calcining the precalcined catalyst under a nitrogen atmosphere to form the catalyst, and washing the catalyst with an oxalic acid solution having a concentration of oxalic acid from about 0.1 M to about 0.36 M. In some embodiments, the concentration of oxalic acid is from about 0.16 M to about 0.3 M.

The oxidative dehydrogenation catalyst can be characterized by having XRD diffraction peaks (2θ degrees) at least at 26.3±0.3 and 29.4±0.3, wherein the XRD is obtained using CuKα radiation. In some embodiments, the catalyst is characterized by having XRD diffraction peaks (2θ degrees) at least at 25.4±0.2, 26.3±0.3, 25.6±0.2, 28.3±0.3, 29.3±0.2, 30.6±0.3, and 31.9±0.2, wherein the XRD is obtained using CuKα radiation. In some embodiments, the catalyst is characterized by having XRD diffraction peaks (2θ degrees) at least at 6.5±0.3, 7.8±0.2, 9.0±0.2, 10.8±0.2, 12.9±0.3, 13.4±0.2, 25.4±0.2, 26.3±0.3, 25.6±0.2, 28.3±0.3, 29.3±0.2, 29.8±0.2, 30.6±0.3, 31.5±0.3, 31.9±0.2, 34.2±0.3, and 35.4±0.3, wherein the XRD is obtained using CuKα radiation.

In some embodiments, the catalyst has a 35% conversion temperature from about 380° C. to about 400° C. and a selectivity to ethylene from about 60% to about 70%.

Also provided in this disclosure is an oxidative dehydrogenation catalyst that includes molybdenum, vanadium, and oxygen. The molar ratio of molybdenum to vanadium in the catalyst is from 1:0.43 to 1:0.46. Oxygen is present in the catalyst at least in an amount to satisfy the valency of any present metal oxides. The catalyst has a 35% conversion temperature from about 360° C. to about 380° C. and a selectivity to ethylene of greater than 75%.

Also provided in this disclosure is an oxidative dehydrogenation catalyst that includes molybdenum, vanadium, and oxygen. The molar ratio of molybdenum to vanadium in the catalyst is from 1:0.43 to 1:0.46. Oxygen is present in the catalyst at least in an amount to satisfy the valency of any present metal oxides. The catalyst has a 35% conversion temperature from about 310° C. to about 330° C. and a selectivity to ethylene of greater than 80%.

Also provided in this disclosure is an oxidative dehydrogenation catalyst that includes molybdenum, vanadium, and oxygen. The molar ratio of molybdenum to vanadium in the catalyst is from 1:0.41 to 1:0.48. Oxygen is present in the catalyst at least in an amount to satisfy the valency of any present metal oxides. The catalyst is prepared by a method that includes preparing an aqueous mixture including molybdenum, vanadium, and an anionic surfactant; hydrothermally reacting the mixture at a temperature from about 200° C. to about 250° C. to form a precalcined catalyst; and calcining the precalcined catalyst at about 375° C. to about 425° C. for about 1 hour to about 4 hours to form the oxidative dehydrogenation catalyst. The aqueous mixture including molybdenum, vanadium, and the anionic surfactant is prepared by at least combining an aqueous mixture including molybdenum and an aqueous mixture including vanadium. The aqueous mixture including molybdenum is be prepared from at least $(NH_4)_6Mo_7O_{24}.4H_2O$ and a first water, while the aqueous mixture including vanadium is prepared from at least $VOSO_4.XH_2O$ and a second water. The molar ratio of $(NH_4)_6Mo_7O_{24}.4H_2O$ to $VOSO_4.XH_2O$ is about 1:1 to about 1:5. For example, the molar ratio of $(NH_4)_6Mo_7O_{24}.4H_2O$ to $VOSO_4.XH_2O$ can be about 1:3.

In some embodiments, the aqueous mixture of molybdenum, vanadium, and the anionic surfactant can be contained by a glass liner during the hydrothermal reaction.

Also provided in this disclosure is an oxidative dehydrogenation catalyst that includes molybdenum, vanadium, and oxygen. The molar ratio of molybdenum to vanadium in the catalyst is from 1:0.41 to 1:0.48. Oxygen is present in the catalyst at least in an amount to satisfy the valency of any present metal oxides. The catalyst can be prepared by a method that includes preparing an aqueous mixture that includes molybdenum, vanadium, and sodium octyl sulfate. The method further includes hydrothermally reacting the mixture to provide a precalcined catalyst at a temperature from about 200° C. to about 250° C. and calcining the precalcined catalyst at about 375° C. to about 425° C. for about 1 hour to about 4 hours to form the oxidative dehydrogenation catalyst. The aqueous mixture including molybdenum, vanadium, and sodium octyl sulfate is prepared by at least combining an aqueous mixture including molybdenum and an aqueous mixture including vanadium. The aqueous mixture including molybdenum is prepared from at least $(NH_4)_6Mo_7O_{24}.4H_2O$ and a first water, while the aqueous mixture including vanadium is prepared from at least $VOSO_4.XH_2O$ and a second water. The molar ratio of $(NH_4)_6Mo_7O_{24}.4H_2O$ to $VOSO_4.XH_2O$ can be about 1:1 to about 1:5. For example, the molar ratio of $(NH_4)_6Mo_7O_{24}.4H_2O$ to $VOSO_4.XH_2O$ can be about 1:3.

In some embodiments, the aqueous mixture including molybdenum, vanadium, and sodium octyl sulfate is be contained by a glass liner during the hydrothermal reaction.

Also provided in this disclosure is a composition that includes an oxidative dehydrogenation catalyst. The oxidative dehydrogenation catalyst can be any oxidative dehydrogenation catalyst described herein.

The composition can further include an adjuvant. The adjuvant can be a material or compound that is capable of functioning as a support, a binder, an agglomerating agent, a promoter, an agent capable of at least partially reacting with the oxidative dehydrogenation catalyst, or a combination thereof. In some embodiments, the adjuvant includes an alumina, goethite, or a combination thereof.

In some embodiments, the adjuvant is present in the composition in an amount from about 40 wt. % to about 80 wt. %, about 50 wt. % to about 70 wt. %, or about 55 wt. % to about 65 wt. %. For example, the composition can include about 55 wt. %, about 60 wt. %, or about 65 wt. % of the adjuvant.

In some embodiments, the oxidative dehydrogenation catalyst is present in an amount from about 20 wt. % to about 60 wt. %, about 30 wt. % to about 50 wt. %, or about 35 wt. % to about 45 wt. % of the composition. For example, the composition can include about 35 wt. %, about 40 wt. %, or about 45 wt. % of the oxidative dehydrogenation catalyst.

In some embodiments, the adjuvant is an alumina. The alumina can be an aluminum oxide, an alumina monohydrate, an alumina trihydrate, an alumina-silica, a bauxite, a calcined aluminum, a transition alumina, a calcined hydrotalcite, or a combination thereof. The calcined aluminum can include a gibbsite, a bayerite, a boehmite, or a combination thereof. As used herein, the term "boehmite" includes, but is not limited to, pseudoboehmites. In some embodiments, the adjuvant is a pseudoboehmite. For example, the adjuvant can be the pseudoboehmite VERSAL™ 250. VERSAL™ 250 has a dispersibility index (%<1 mu) of 20-30, a bulk density of 12-16 pounds per cubic foot (lbs/ft$^3$), a surface area of about 320 meters squared per gram (m$^2$/g), and a loss on ignition (LOI) of about 26 wt. %. The dispersibility index for VERSAL™ 250 can be determined by using 8 grams of sample on a volatile free basis and 96 ml of 0.22 normal (N) nitric acid solution, which is approximately 260 meq nitric acid per 100 g alumina, mixing the acidic alumina slurry in a WARING® blender at low speed (17000 rpm) for 5 min, and then determining particle size distribution by using a SEDIGRAPH® PSA—with the results reported as wt. % submicron particles.

In some embodiments, the composition includes the oxidative dehydrogenation catalyst and a pseudoboehmite, such as VERSAL™ 250. The oxidative dehydrogenation catalyst can be about 20 wt. % to about 60 wt. % of the composition and the pseudoboehmite can be about 40 wt. % to about 80 wt. % of the composition. For example, the oxidative dehydrogenation catalyst can be about 30 wt. % to about 50 wt. % of the composition and the pseudoboehmite can be about 50 wt. % to about 70 wt. % of the composition. In some embodiments, the oxidative dehydrogenation catalyst is about 40 wt. % of the composition and the pseudoboehmite is about 60 wt. % of the composition.

The composition including the oxidative dehydrogenation catalyst and an alumina adjuvant, such as the pseudoboehmite VERSAL™ 250, can be prepared by providing a mixture that includes the oxidative dehydrogenation catalyst, the alumina, and a water, and calcining the mixture to provide the catalyst composition. The water can be present in the mixture in an amount from about 10 wt. % to about 99 wt. %, about 30 wt. % to about 80 wt. %, or about 45 wt. % to about 75 wt. %. The ratio of alumina to the oxidative dehydrogenation catalyst in the mixture can be about 80:20 to about 40:60 or about 70:30 to about 50:50. For example, the ratio of alumina to the oxidative dehydrogenation catalyst in the mixture can be about 60:40.

In some embodiments, a substantial amount of the water in the mixture can be removed by heating the mixture prior to calcining the mixture. For example, the mixture including the oxidative dehydrogenation catalyst, the alumina, and the water can be heated at a temperature from about 60° C. to about 100° C., about 70° C. to about 90° C., or about 75° C. to about 85° C. to remove a substantial amount of the water in the mixture. In some embodiments, the mixture including the mixed metal oxide, the alumina, and the water can be heated at a temperature from about 70° C., 80° C., or about 90° C. The mixture including the oxidative dehydrogenation catalyst, the alumina, and the water can also be agitated, for example by stirring, while the mixture is heated. After a substantial amount of the water is removed, the mixture can be in the form of a paste.

The mixture including the catalyst and the alumina can be calcined at about 300° C. to about 450° C. or about 325° C. to about 375° C. For example, the mixture including the catalyst and the alumina can be calcined at about 330° C., 340° C., 350° C., 360° C., or about 370° C.

When the composition is prepared by providing the mixture including the oxidative dehydrogenation catalyst, the alumina, and the water; optionally heating the mixture to remove a substantial amount of the water; and then calcining the mixture to provide the composition, some of the alumina can react with the oxidative dehydrogenation catalyst to form an alumina reacted oxidative dehydrogenation catalyst while the unreacted alumina can function as a binder, a support, a promoter, or a combination thereof.

In some embodiments, the adjuvant includes alumina and goethite. The alumina can be present in the composition in an amount from about 40 wt. % to about 80 wt. % and the goethite is present in the composition in an amount of 1 wt. % to 20 wt. %. For example, the alumina can be present in an amount from about 55 wt. % to about 65 wt. % and the goethite can be present in an amount from about 5 wt. % to about 15 wt. %. In some embodiments, the composition can include about 60 wt. % alumina and about 8 wt. % goethite.

Additionally, when the composition further includes an adjuvant, the adjuvant can be a support. The support can be a solid material on which the oxidative dehydrogenation catalyst is affixed to, distributed of over, or both for the purpose of increasing the surface area of the dehydrogenation catalyst. The support can be an alumina-based support, a magnesia-based support, a silica-based support, a zirconia-based support, a zeolite-based support, an iron-based support, or a combination thereof. In some embodiments, the support is present in an amount from about 40 wt. % to about 80 wt. %, about 50 wt. % to about 70 wt. %, or about 55 wt. % to about 65 wt. % of the composition. For example, the composition can include about 55 wt. %, about 60 wt. %, or about 65 wt. % of the support.

In some embodiments, the adjuvant is a promoter. The effects of a promoter upon an oxidative dehydrogenation catalyst for a dehydrogenation process can include, for example, enhanced alkane conversion (e.g. a lower 35% conversion temperature), enhanced selectivity to ethylene, suppression of coke formation, elimination of high pre-heat temperature, and improved stability of the oxidative dehydrogenation catalyst.

The promoter can be present in the composition in an amount from about 1 wt. % to about 20 wt. %, about 5 wt. % to about 15 wt. %, or about 5 wt. % to about 10 wt. % of the composition. For example, the composition can include about 8 wt. % of the promoter.

The promoter can include lithium, sodium, potassium, rubidium, cesium, beryllium, magnesium, calcium, strontium, barium, goethite, or a combination thereof. In some embodiments, the promoter is a beryllium. For example, the promoter can be a beryllium oxide (i.e. a beryllia). The beryllium oxide can be present in the composition in an amount from about 1 wt. % to about 20 wt. %, about 5 wt. % to about 15 wt. %, or about 5 wt. % to about 10 wt. % of the composition. For example, the composition can include about 8 wt. % of the beryllium oxide.

Also provided herein, is a composition that includes an oxidative dehydrogenation catalyst and an adjuvant. The oxidative dehydrogenation catalyst includes molybdenum, vanadium, and oxygen. The molar ratio of molybdenum to vanadium in the catalyst is from 1:0.32 to 1:0.59. Oxygen is present in the catalyst at least in an amount to satisfy the valency of any present metal oxides. The adjuvant is an alumina. Further, the composition is prepared by a method that includes providing a mixture including the oxidative dehydrogenation catalyst, the alumina, and a water, and calcining the mixture to provide the composition.

In some embodiments, the composition includes about 40 wt. % to about 80 wt. % of the alumina and about 20 wt. % to about 60 wt. % of the oxidative dehydrogenation catalyst.

Further provided herein, is a composition that includes an oxidative dehydrogenation catalyst and a pseudoboehmite (e.g., VERSAL® 250). The oxidative dehydrogenation catalyst includes molybdenum, vanadium, and oxygen. The molar ratio of molybdenum to vanadium in the catalyst is from 1:0.41 to 1:0.48. Oxygen is present in the catalyst at least in an amount to satisfy the valency of any present metal oxides. The composition is prepared by a method that includes providing a mixture including the oxidative dehydrogenation catalyst, the alumina, and a water. The method further includes removing a substantial amount of the water (e.g., more than 50 wt. %, 60 wt. %, 70 wt. %, 80 wt. %, 90 wt. % or more than 95 wt. % of the water) by heating the mixture at a temperature from about 70° C. to about 90° C. and then calcining the mixture at a temperature from about 325° C. to about 375° C. to provide the composition.

In some embodiments, the composition includes about 50 wt. % to about 70 wt. % of the pseudoboehmite and about 30 wt. % to about 50 wt. % of the oxidative dehydrogenation catalyst.

Also provided in this disclosure, is a method of preparing an oxidative dehydrogenation catalyst includes molybdenum, vanadium, and oxygen. The molar ratio of molybdenum to vanadium in the catalyst is from 1:0.32 to 1:0.59. Oxygen is present in the catalyst at least in an amount to satisfy the valency of any present metal oxides. The method includes preparing an aqueous mixture including molybdenum and vanadium, hydrothermally reacting the mixture to form a precalcined catalyst, and calcining the precalcined catalyst to form the oxidative dehydrogenation catalyst.

The aqueous mixture including molybdenum and vanadium can be prepared by combining an aqueous mixture including molybdenum and an aqueous mixture including vanadium. The aqueous mixture including molybdenum can be prepared from $(NH_4)_6Mo_7O_{24} \cdot 4H_2O$ and a first water. The aqueous mixture including vanadium can be prepared from $VOSO_4 \cdot XH_2O$ and a second water. The molar ratio of $(NH_4)_6Mo_7O_{24} \cdot 4H_2O$ to $VOSO_4 \cdot XH_2O$ can be about 0.5:1 to about 1:10, about 1:1 to about 1:5, or about 1:2 to about 1:4. For example, the molar ratio of $(NH_4)_6Mo_7O_{24} \cdot 4H_2O$ to $VOSO_4 \cdot XH_2O$ can be about 1:3. In some embodiments, the molar ratio of $(NH_4)_6Mo_7O_{24} \cdot 4H_2O$ to $VOSO_4 \cdot XH_2O$ can also be about 1:1.5 to about 1:2.

The first and the second water can include distilled water, deionized water, demineralized water, mineral water, or a combination thereof. In some embodiments, the first and the second water are distilled water.

The aqueous mixture including molybdenum and vanadium can further include a surfactant. The surfactant can be a non-ionic surfactant, an anionic surfactant, a cationic surfactant, or a combination thereof. The anionic surfactant can be selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof. In some embodiments, the surfactant is sodium octyl sulfate.

Hydrothermally reacting the mixture to form the precalcined catalyst can include heating the aqueous mixture of molybdenum and vanadium at a temperature from about 150° C. to about 300° C., about 175° C. to about 275° C., or about 200° C. to about 250° C. For example, hydrothermally reacting the mixture to form the precalcined catalyst can include heating the aqueous mixture of molybdenum and vanadium at a temperature from about 230° C. Further, hydrothermally reacting the mixture to form the precalcined catalyst can include heating the aqueous mixture of molybdenum and vanadium under a pressure from about 1 psi to about 1,500 psi, about 700 psi to about 1,100 psi, or about 800 psi to about 1,000 psi.

In some embodiments, the method of preparing the oxidative dehydrogenation catalyst does not include washing the precalcined catalyst with an alcohol prior to calcination. For example, the method of preparing the oxidative dehydrogenation catalyst may not include washing the precalcined catalyst with ethanol. As such, the precalcined catalyst can be free of any residual alcohol, which may react with the precalcined catalyst during calcination. Further, it has been unexpectedly discovered, as shown in Example 1.2, that an oxidative dehydrogenation catalyst prepared without an ethanol wash can have a higher selectivity to ethylene as compared to a catalyst prepared with an ethanol wash.

The step of calcining the precalcined catalyst can be carried out at a temperature from about 300° C. to about 500° C., about 350° C. to about 450° C., or about 375° C. to about 425° C. For example, the precalcined catalyst can be calcined at about 375° C., 385° C., 395° C., 405° C., 415° C., or about 425° C. In some embodiments, the precalcined catalyst is calcined at about 400° C.

In some embodiments, the precalcined catalyst is calcined at about 300° C. to about 500° C. for about 1 hour to about 24 hours. For example, the precalcined catalyst can be calcined at about 375° C. to about 425° C. for about 1 hour to about 4 hours. In some embodiments, the precalcined catalyst is calcined at about 400° C. for about 2 hours Also provided herein is a method for the oxidative dehydrogenation of ethane to ethylene in an oxidative dehydrogenation reactor with any oxidative dehydrogenation catalyst or oxidative dehydrogenation composition described herein.

Ethylene can subsequently be converted into a variety of products. For example, ethylene can be converted into many various compounds including low density polyethylene, high density polyethylene, ethylene dichloride, ethylene oxide, ethylbenzene, linear alcohols, vinyl acetate, alkanes, alpha olefins, various hydrocarbon-based fuels, ethanol and the like. These compounds can then be further processed using methods well known to one of ordinary skill in the art to obtain other valuable chemicals and consumer products.

Non-limiting embodiments disclosed herein include:

Embodiment A: An oxidative dehydrogenation catalyst including molybdenum, vanadium, and oxygen, wherein: the molar ratio of molybdenum to vanadium in the catalyst is from 1:0.15 to 1:0.75, as determined by inductively coupled plasma mass spectrometry (ICP-MS), oxygen is present in the catalyst at least in an amount to satisfy the valency of any present metal oxides, and the amorphous phase of the catalyst is greater than 55 wt. %, as determined by X-ray diffraction (XRD).

Embodiment A may have one or more of the following additional elements in any combination:

Element A1: Wherein the molar ratio of molybdenum to vanadium in the catalyst is from 1:0.20 to 1:0.70.

Element A2: Wherein the molar ratio of molybdenum to vanadium in the catalyst is from 1:0.25 to 1:0.65.

Element A3: Wherein the molar ratio of molybdenum to vanadium in the catalyst is from 1:0.29 to 1:0.59.

Element A4: Wherein the molar ratio of molybdenum to vanadium in the catalyst is from 1:0.32 to 1:0.38.

Element A5: Wherein the molar ratio of molybdenum to vanadium in the catalyst is from 1:0.36 to 1:0.43.

Element A6: Wherein the molar ratio of molybdenum to vanadium in the catalyst is from 1:0.37 to 1:0.44.

Element A7: Wherein the molar ratio of molybdenum to vanadium in the catalyst is from 1:0.41 to 1:0.48.

Element A8: Wherein the molar ratio of molybdenum to vanadium in the catalyst is from 1:0.42 to 1:0.46.

Element A9: Wherein the molar ratio of molybdenum to vanadium in the catalyst is from 1:0.44 to 1:0.52.

Element A10: Wherein the molar ratio of molybdenum to vanadium in the catalyst is from 1:0.45 to 1:0.54.

Element A11: Wherein the molar ratio of molybdenum to vanadium in the catalyst is from 1:0.50 to 1:0.59.

Element A12: Wherein the catalyst has an amorphous phase from 55 wt. % to 80 wt. %.

Element A13: Wherein the catalyst has an amorphous phase from 55 wt. % to 75 wt. %.

Element A14: Wherein the catalyst has a 35% conversion temperature from about 300° C. to about 400° C.

Element A15: Wherein the catalyst has a 35% conversion temperature from about 310° C. to about 385° C.

Element A16: Wherein the catalyst has a 35% conversion temperature from about 310° C. to about 375° C.

Element A17: Wherein the catalyst has a 35% conversion temperature from about 360° C. to about 380° C.

Element A18: Wherein the catalyst has a 35% conversion temperature from about 310° C. to about 330° C.

Element A19: Wherein the catalyst has a selectivity to ethylene from 65% to 99%.

Element A20: Wherein the catalyst has a selectivity to ethylene from 75% to 80%.

Element A21: Wherein the catalyst has a selectivity to ethylene from 80% to 90%.

Element A22: Wherein the catalyst has a 35% conversion temperature from about 310° C. to about 385° C. and a selectivity to ethylene from about 75% to about 90%.

Element A23: Wherein the catalyst has a 35% conversion temperature from about 360° C. to about 380° C. and a selectivity to ethylene from about 75% to about 80%.

Element A24: Wherein the catalyst has a 35% conversion temperature from about 310° C. to about 330° C. and a selectivity to ethylene from 80% to 90%.

Element A25: Wherein the catalyst is prepared by a method that includes: providing an aqueous mixture including molybdenum and vanadium, hydrothermally reacting the mixture to form a precalcined catalyst, and calcining the precalcined catalyst to form the catalyst.

Element A26: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein providing the aqueous mixture including molybdenum and vanadium includes combining an aqueous mixture including molybdenum and an aqueous mixture including vanadium.

Element A27: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein providing the aqueous mixture including molybdenum and vanadium includes combining an aqueous mixture including molybdenum and an aqueous mixture including vanadium; and wherein the aqueous mixture including molybdenum is prepared from at least $(NH_4)_6Mo_7O_{24} \cdot 4H_2O$ and a first water.

Element A28: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein providing the aqueous mixture including molybdenum and vanadium includes combining an aqueous mixture including molybdenum and an aqueous mixture including vanadium; and wherein the aqueous mixture including vanadium is prepared from at least $VOSO_4 \cdot XH_2O$ and a second water.

Element A29: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the aqueous mixture including molybdenum and vanadium further includes a surfactant.

Element A30: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the aqueous mixture including molybdenum and vanadium further includes a surfactant; and wherein the surfactant is selected from a non-ionic surfactant, an anionic surfactant, a cationic surfactant, or a combination thereof.

Element A31: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the aqueous mixture including molybdenum and vanadium further includes an anionic surfactant selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof.

Element A32: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the aqueous mixture including molybdenum and vanadium further includes an anionic surfactant wherein the anionic surfactant includes sodium dodecyl sulfate.

Element A33: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the aqueous mixture including molybdenum and vanadium further includes an anionic surfactant wherein the anionic surfactant includes sodium dodecyl sulfate sodium octyl sulfate.

Element A34: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form the precalcined catalyst includes heating the aqueous mixture of molybdenum and vanadium in the presence of a catalyst seed.

Element A35: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium.

Element A36: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium; wherein the composition including molybdenum and vanadium includes a catalyst including molybdenum, vanadium, and oxygen, wherein the molar ratio of molybdenum to vanadium in the catalyst is from 1:0.15 to 1:0.75, as determined by ICP-MS.

Element A37: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium.

Element A38: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium; and wherein the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40, and wherein oxygen is present at least in an amount to satisfy the valency of any present metal oxides.

Element A39: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes heating the aqueous mixture of molybdenum and vanadium at a temperature from about 150° C. to about 300° C.

Element A40: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes heating the aqueous mixture of molybdenum and vanadium at a temperature from about 200° C. to about 250° C.

Element A41: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes heating the aqueous mixture of molybdenum and vanadium at a temperature from about 230° C.

Element A42: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes heating the aqueous mixture of molybdenum and vanadium under a pressure from about 1 psi to about 1,500 psi.

Element A43: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes heating the aqueous mixture of molybdenum and vanadium under a pressure from about 400 psi to about 440 psi.

Element A44: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes heating the aqueous mixture of molybdenum and vanadium at a temperature from about 200° C. to about 250° C. under a pressure from about 200 psi to about 900 psi.

Element A45: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes heating the aqueous mixture of molybdenum and vanadium at a temperature from about 230° C. under a pressure from about 400 psi to about 440 psi.

Element A46: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes contacting the mixture with a glass liner, stainless steel, or a Teflon liner.

Element A47: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes contacting the mixture with a glass liner.

Element A48: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein hydrothermally reacting the mixture to form a precalcined catalyst includes contacting the mixture with a Teflon liner.

Element A49: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the precalcined catalyst is calcined at about 300° C. to about 500° C.

Element A50: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the precalcined catalyst is calcined at about 375° C. to about 425° C.

Element A51: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and, wherein the precalcined catalyst is calcined at about 400° C.

Element A52: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the precalcined catalyst is calcined at about 300° C. to about 500° C. for about 1 hour to about 24 hours.

Element 53: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the precalcined catalyst is calcined at about 375° C. to about 425° C. for about 1 hour to about 4 hours.

Element A54: Wherein the catalyst is prepared by a method that includes: providing an aqueous mixture including molybdenum and vanadium, hydrothermally reacting the mixture to form a precalcined catalyst, and calcining the precalcined catalyst to form the catalyst; and wherein the precalcined catalyst is calcined at about 400° C. for about 2 hours.

By way of non-limiting example, exemplary element combinations applicable to Embodiment A include: A12, A14, and A19; and A12 and A25; A12, A25, A27, and A28; and A12, A25, A27, A28, A39, and A50.

Embodiment B: An oxidative dehydrogenation catalyst including molybdenum, vanadium, and oxygen, wherein: the molar ratio of molybdenum to vanadium in the catalyst is from 1:0.20 to 1:0.60, oxygen is present in the catalyst at least in amount to satisfy the valency of any present metal oxides, and the amorphous phase of the catalyst is greater than 55 wt. %.

Embodiment B may have one or more of the following additional elements in any combination:

Element B1: Wherein the molar ratio of molybdenum to vanadium in the catalyst is from 1:0.24 to 1:0.58.

Element B2: Wherein the molar ratio of molybdenum to vanadium in the catalyst is from 1:0.29 to 1:0.53.

Element B3: Wherein the amorphous phase of the catalyst is from 55 wt. % to 75 wt. %.

Element B4: Wherein the amorphous phase of the catalyst is from 60 wt. % to 65 wt. %.

Element B5: Wherein the catalyst characterized by having XRD diffraction peaks (2θ degrees) at least at 23.5±0.5, 25.6±0.5, and 27.1±0.7, wherein the XRD is obtained using CuKα radiation.

Element B6: Wherein the catalyst is characterized by having XRD diffraction peaks (2θ degrees) at least at 21.7±0.2, 23.5±0.5, 25.0±0.3, 25.6±0.3, and 27.1±0.7, wherein the XRD is obtained using CuKα radiation.

Element B7: Wherein the catalyst has a 35% conversion temperature from about 300° C. to about 425° C.

Element B8: Wherein the catalyst has a selectivity to ethylene from 65% to 95%.

Element B9: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst.

Element B10: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein providing the aqueous mixture including molybdenum and vanadium includes combining an aqueous mixture including molybdenum and an aqueous mixture including vanadium.

Element B11: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein providing the aqueous mixture including molybdenum and vanadium includes combining an aqueous mixture including molybdenum and an aqueous mixture including vanadium; and wherein the aqueous mixture including molybdenum is prepared from at least $(NH_4)_6Mo_7O_{24} \cdot 4H_2O$ and a first water.

Element B12: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein providing the aqueous mixture including molybdenum and vanadium includes combining an aqueous mixture including molybdenum and an aqueous mixture including vanadium; and wherein the aqueous mixture including vanadium is prepared from at least $VOSO_4 \cdot XH_2O$ and a second water.

Element B13: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the aqueous mixture including molybdenum and vanadium further includes a surfactant.

Element B14: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the aqueous mixture including molybdenum and vanadium further includes a surfactant; and wherein the surfactant is selected from a non-ionic surfactant, an anionic surfactant, a cationic surfactant, or a combination thereof.

Element B15: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the aqueous mixture including molybdenum and vanadium further includes a surfactant; and wherein the surfactant is selected from a non-ionic surfactant, an anionic surfactant, a cationic surfactant, or a combination thereof; and wherein the anionic surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof.

Element B16: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the aqueous mixture including molybdenum and vanadium further includes a surfactant; and wherein the surfactant includes sodium dodecyl sulfate.

Element B17: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the aqueous mixture including molybdenum and vanadium further includes a surfactant; and wherein the surfactant includes sodium octyl sulfate.

Element B18: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form the precalcined catalyst includes heating the aqueous mixture of molybdenum and vanadium in the presence of a catalyst seed.

Element B19: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium.

Element B20: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium; and wherein the composition including molybdenum and vanadium includes a catalyst including molybdenum, vanadium, and oxygen, wherein the molar ratio of molybdenum to vanadium in the catalyst is from 1:0.15 to 1:0.75.

Element B20: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium.

Element B21: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium; and wherein the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40, and wherein oxygen is present at least in an amount to satisfy the valency of any present metal oxides.

Element B22: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes heating the aqueous mixture of molybdenum and vanadium at a temperature from about 150° C. to about 300° C.

Element B23: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes heating the aqueous mixture of molybdenum and vanadium at a temperature from about 200° C. to about 250° C.

Element B24: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes heating the aqueous mixture of molybdenum and vanadium at a temperature from about 230° C.

Element B25: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes heating the aqueous mixture of molybdenum and vanadium under a pressure from about 1 psi to about 1,500 psi.

Element B26: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes heating the aqueous mixture of molybdenum and vanadium under a pressure from about 400 psi to about 440 psi.

Element B27: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes heating the aqueous mixture of molybdenum and vanadium at a temperature from about 200° C. to about 250° C. under a pressure from about 200 psi to about 900 psi.

Element B28: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and hydrothermally reacting the mixture to form a precalcined catalyst includes heating the aqueous mixture of molybdenum and vanadium at a temperature of about 230° C. under a pressure from about 400 psi to about 440 psi.

Element B29: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes contacting the mixture with a glass liner, stainless steel, or a Teflon liner.

Element B30: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes contacting the mixture with a glass liner.

Element B31: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein hydrothermally reacting the mixture to form a precalcined catalyst includes contacting the mixture with a Teflon liner.

Element B32: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the precalcined catalyst is calcined at about 300° C. to about 500° C.

Element B33: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the precalcined catalyst is calcined at about 375° C. to about 425° C.

Element B34: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the precalcined catalyst is calcined at about 400° C.

Element B35: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the precalcined catalyst is calcined at about 300° C. to about 500° C. for about 1 hour to about 24 hours.

Element B36: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the precalcined catalyst is calcined at about 375° C. to about 425° C. for about 1 hour to about 4 hours.

Element B32: Wherein the catalyst is prepared by a method that includes: providing an aqueous mixture including molybdenum and vanadium, hydrothermally reacting the mixture to form a precalcined catalyst, and calcining the precalcined catalyst in the presence of air to form the catalyst; and wherein the precalcined catalyst is calcined at about 400° C. for about 2 hours.

By way of non-limiting example, exemplary element combinations applicable to Embodiment B include: B1 and B3; B1, B3, and B5; B1, B3, B7, and B8; B1, B3, B11, and B12; and B1, B3, B11, B12, and B27.

Embodiment C: An oxidative dehydrogenation catalyst including molybdenum, vanadium, and oxygen, wherein the molar ratio of molybdenum to vanadium in the catalyst is from 1:0.20 to 1:0.50, oxygen is present in the catalyst at least in amount to satisfy the valency of any present metal oxides, and the amorphous phase of the catalyst is greater than 55 wt. %.

Embodiment C may have one or more of the following additional elements in any combination:

Element C1: Wherein the molar ratio of molybdenum to vanadium in the catalyst is from 1:0.25 to 1:0.45.

Element C2: Wherein the molar ratio of molybdenum to vanadium in the catalyst is from 1:0.29 to 1:0.39.

Element C3: Wherein the amorphous phase of the catalyst is from 55 wt. % to 85 wt. %.

Element C4: Wherein the amorphous phase of the catalyst is from 65 wt. % to 75 wt. %.

Element C5: Wherein the catalyst is characterized by having XRD diffraction peaks (2θ degrees) at least at 23.5±0.5, 25.6±0.5, and 27.1±0.7, wherein the XRD is obtained using CuKα radiation.

Element C6: Wherein the catalyst is characterized by having XRD diffraction peaks (2θ degrees) at least at 12.7±0.3, 23.5±0.5, 25.7±0.3, and 27.1±0.7, wherein the XRD is obtained using CuKα radiation.

Element C7: Wherein the catalyst has a 35% conversion temperature from about 320° C. to about 400° C.

Element C8: Wherein the catalyst has a selectivity to ethylene from 70% to 95%.

Element C9: Wherein the catalyst has a selectivity to ethylene from 80% to 85%.

Element C10: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution.

Element C11: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein providing the aqueous mixture including molybdenum and vanadium includes combining an aqueous mixture including molybdenum and an aqueous mixture including vanadium.

Element C12: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the aqueous mixture including molybdenum is prepared from at least $(NH_4)_6Mo_7O_{24}\cdot 4H_2O$ and a first water.

Element C13: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the aqueous mixture including vanadium is prepared from at least $VOSO_4\cdot XH_2O$ and a second water.

Element C14: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the aqueous mixture including molybdenum and vanadium further includes a surfactant.

Element C15: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the aqueous mixture including molybdenum and vanadium further includes a surfactant; and wherein the surfactant is selected from a non-ionic surfactant, an anionic surfactant, a cationic surfactant, or a combination thereof.

Element C16: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the aqueous mixture including molybdenum and vanadium further includes a surfactant; and wherein the surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof.

Element C17: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the aqueous mixture including molybdenum and vanadium further includes a surfactant; and wherein the surfactant includes sodium dodecyl sulfate.

Element C18: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the aqueous mixture including molybdenum and vanadium further includes a surfactant; and wherein the surfactant includes sodium octyl sulfate.

Element C19: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form the precalcined catalyst includes heating the aqueous mixture of molybdenum and vanadium in the presence of a catalyst seed.

Element C20: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium.

Element C20: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium; and wherein the composition including molybdenum and vanadium includes a catalyst including molybdenum, vanadium, and oxygen, wherein the molar ratio of molybdenum to vanadium in the catalyst is from 1:0.15 to 1:0.75.

Element C21: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium.

Element C22: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium; and wherein the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40, as determined by ICP-MS; and wherein oxygen is present at least in an amount to satisfy the valency of any present metal oxides.

Element C23: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes heating the aqueous mixture of molybdenum and vanadium at a temperature from about 150° C. to about 300° C.

Element C24: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes heating the aqueous mixture of molybdenum and vanadium at a temperature from about 200° C. to about 250° C.

Element C25: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes heating the aqueous mixture of molybdenum and vanadium at a temperature from about 230° C.

Element C26: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and hydrothermally reacting the mixture to form a precalcined catalyst includes heating the aqueous mixture of molybdenum and vanadium under a pressure from about 1 psi to about 1,500 psi.

Element C27: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes heating the aqueous mixture of molybdenum and vanadium under a pressure from about 400 psi to about 440 psi.

Element C28: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes heating the aqueous mixture of molybdenum and vanadium at a temperature from about 200° C. to about 250° C. under a pressure from about 200 psi to about 900 psi.

Element C29: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes heating the aqueous mixture of molybdenum and vanadium at a temperature of about 230° C. under a pressure from about 400 psi to about 440 psi.

Element C30: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes contacting the mixture with a glass liner, stainless steel, or Teflon liner.

Element C31: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes contacting the mixture with a glass liner.

Element C32: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein hydrothermally reacting the mixture to form a precalcined catalyst includes contacting the mixture with a Teflon liner.

Element C33: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the precalcined catalyst is calcined at about 300° C. to about 500° C.

Element C34: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the precalcined catalyst is calcined at about 375° C. to about 425° C.

Element C35: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the precalcined catalyst is calcined at about 400° C.

Element C36: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the precalcined catalyst is calcined at about 300° C. to about 500° C. for about 1 hour to about 24 hours.

Element C37: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the precalcined catalyst is calcined at about 375° C. to about 425° C. for about 1 hour to about 4 hours.

Element C38: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the precalcined catalyst is calcined at about 400° C. for about 2 hours.

Element C39: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the acid solution includes oxalic acid.

Element C40: Wherein the catalyst is prepared by a method that includes: providing an aqueous mixture including molybdenum and vanadium, hydrothermally reacting the mixture to form a precalcined catalyst, air calcining the precalcined catalyst to form the catalyst, and washing the catalyst with an acid solution; and wherein the acid solution includes oxalic acid; and wherein the concentration of oxalic acid is from about 0.05 M to about 0.5 M.

By way of non-limiting example, exemplary element combinations applicable to Embodiment C include: C1 and C3; C1, C3, and C5; C1, C3, C7, and C8; C1, C3, and C10; C1, C3, C12, and C13; C1, C3, C12, C13, and C39; and C1, C3, C12, C13, and C40.

Embodiment D: An oxidative dehydrogenation catalyst including molybdenum, vanadium, and oxygen, wherein the molar ratio of molybdenum to vanadium in the catalyst is from 1:0.30 to 1:0.70, oxygen is present in the catalyst at least in amount to satisfy the valency of any present metal oxides, and the amorphous phase of the catalyst is greater than 55 wt. %.

Embodiment D may have one or more of the following additional elements in any combination:

Element D1: Wherein the molar ratio of molybdenum to vanadium in the catalyst is from 1:0.35 to 1:0.65.

Element D2: Wherein the molar ratio of molybdenum to vanadium in the catalyst is from 1:0.40 to 1:0.60.

Element D3: Wherein the amorphous phase of the catalyst is from 55 wt. % to 75 wt. %.

Element D4: Wherein the amorphous phase of the catalyst is from 56 wt. % to 66 wt. %.

Element D5: Wherein the catalyst is characterized by having XRD diffraction peaks (2θ degrees) at least at 26.3±0.3 and 29.4±0.3, wherein the XRD is obtained using CuKα radiation.

Element D6: Wherein the catalyst is characterized by having XRD diffraction peaks (2θ degrees) at least at 22.3±0.4, 25.0±0.2, 26.2±0.2, 29.4±0.3, 32.6±0.2, and 33.4±0.2, wherein the XRD is obtained using CuKα radiation.

Element D7: Wherein the catalyst has a 35% conversion temperature from about 300° C. to about 425° C.

Element D8: Wherein the catalyst has a selectivity to ethylene from 65% to 95%.

Element D9: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst.

Element D10: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein providing the aqueous mixture including molybdenum and vanadium includes combining an aqueous mixture including molybdenum and an aqueous mixture including vanadium.

Element D11: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein providing the aqueous mixture including molybdenum and vanadium includes combining an aqueous mixture including molybdenum and an aqueous mixture including vanadium; and wherein the aqueous mixture including molybdenum is prepared from at least $(NH_4)_6Mo_7O_{24} \cdot 4H_2O$ and a first water.

Element D12: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein providing the aqueous mixture including molybdenum and vanadium includes combining an aqueous mixture including molybdenum and an aqueous mixture including vanadium; and wherein the aqueous mixture including vanadium is prepared from at least $VOSO_4 \cdot XH_2O$ and a second water.

Element D13: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the aqueous mixture including molybdenum and vanadium further includes a surfactant.

Element D14: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the aqueous mixture including molybdenum and vanadium further includes a surfactant; and wherein the surfactant is selected from a non-ionic surfactant, an anionic surfactant, a cationic surfactant, or a combination thereof.

Element D15: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the aqueous mixture including molybdenum and vanadium further includes a surfactant; and wherein the surfactant includes a surfactant is selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof.

Element D16: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the aqueous mixture including molybdenum and vanadium further includes a surfactant; and wherein the surfactant includes sodium dodecyl sulfate.

Element D17: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the aqueous mixture including molybdenum and vanadium further includes a surfactant; and wherein the surfactant includes sodium octyl sulfate.

Element D18: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form the precalcined catalyst includes heating the aqueous mixture of molybdenum and vanadium in the presence of a catalyst seed.

Element D19: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium.

Element D20: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium; and wherein the composition including molybdenum and vanadium includes a catalyst including molybdenum, vanadium, and oxygen, wherein the molar ratio of molybdenum to vanadium in the catalyst is from 1:0.15 to 1:0.75.

Element D21: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium.

Element D22: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium; and wherein the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40; and wherein oxygen is present at least in an amount to satisfy the valency of any present metal oxides.

Element D23: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes heating the aqueous mixture of molybdenum and vanadium at a temperature from about 150° C. to about 300° C.

Element D24: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes heating the aqueous mixture of molybdenum and vanadium at a temperature from about 200° C. to about 250° C.

Element D25: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes heating the aqueous mixture of molybdenum and vanadium at a temperature of about 230° C.

Element D26: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes heating the aqueous mixture of molybdenum and vanadium under a pressure from about 1 psi to about 1,500 psi.

Element D27: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes heating the aqueous mixture of molybdenum and vanadium under a pressure from about 400 psi to about 440 psi.

Element D28: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes heating the aqueous mixture of molybdenum and vanadium at a temperature from about 200° C. to about 250° C. under a pressure from about 200 psi to about 900 psi.

Element D29: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes heating the aqueous mixture of molybdenum and vanadium at a temperature of about 230° C. under a pressure from about 400 psi to about 440 psi.

Element D30: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and hydrothermally reacting the mixture to form a precalcined catalyst includes contacting the mixture with a glass liner, stainless steel, or Teflon liner.

Element D31: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein hydrothermally reacting the mixture to form a precalcined catalyst includes contacting the mixture with a glass liner.

Element D32: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and hydrothermally reacting the mixture to form a precalcined catalyst includes contacting the mixture with a Teflon liner.

Element D33: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and the precalcined catalyst is calcined at about 300° C. to about 500° C.

Element D34: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the precalcined catalyst is calcined at about 375° C. to about 425° C.

Element D35: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and the precalcined catalyst is calcined at about 400° C.

Element D36: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the precalcined catalyst is calcined at about 300° C. to about 500° C. for about 1 hour to about 24 hours.

Element D37: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the precalcined catalyst is calcined at about 375° C. to about 425° C. for about 1 hour to about 4 hours.

Element D38: Wherein the catalyst is prepared by a method that includes: providing an aqueous mixture including molybdenum and vanadium, hydrothermally reacting the mixture to form a precalcined catalyst, and calcining the precalcined catalyst under a nitrogen atmosphere to form the catalyst; and wherein the precalcined catalyst is calcined at about 400° C. for about 2 hours.

By way of non-limiting example, exemplary element combinations applicable to Embodiment D include: D1 and D3; D1, D3, and D5; D1, D3, D7, and D8; D1, D3, and D9; and D1, D3, D11, and D12.

Embodiment E: An oxidative dehydrogenation catalyst including molybdenum, vanadium, and oxygen, wherein the molar ratio of molybdenum to vanadium in the catalyst is from 1:0.30 to 1:0.50, oxygen is present in the catalyst at least in amount to satisfy the valency of any present metal oxides, and the amorphous phase of the catalyst is greater than 45 wt. %, and wherein the catalyst is prepared by a method that includes providing an aqueous mixture including molybdenum and vanadium, hydrothermally reacting the mixture to form a precalcined catalyst, calcining the precalcined catalyst under a nitrogen atmosphere to form the catalyst, and washing the catalyst with an acid solution.

Embodiment E may have one or more of the following additional elements in any combination:

Element E1: Wherein the molar ratio of molybdenum to vanadium in the catalyst is from 1:0.35 to 1:0.45.

Element E2: Wherein the molar ratio of molybdenum to vanadium in the catalyst is about 1:0.41.

Element E3: Wherein the amorphous phase of the catalyst is from 45 wt. % to 75 wt. %.

Element E4: Wherein the amorphous phase of the catalyst is from 45 wt. % to 55 wt. %.

Element E5: Wherein the catalyst is characterized by having XRD diffraction peaks (2θ degrees) at least at 26.3±0.3 and 29.4±0.3, wherein the XRD is obtained using CuKα radiation.

Element E6: Wherein the catalyst is characterized by having XRD diffraction peaks (2θ degrees) at least at 25.4±0.2, 26.3±0.3, 25.6±0.2, 28.3±0.3, 29.3±0.2, 30.6±0.3, and 31.9±0.2, wherein the XRD is obtained using CuKα radiation.

Element E7: Wherein the catalyst is characterized by having XRD diffraction peaks (2θ degrees) at least at 6.5±0.3, 7.8±0.2, 9.0±0.2, 10.8±0.2, 12.9±0.3, 13.4±0.2, 25.4±0.2, 26.3±0.3, 25.6±0.2, 28.3±0.3, 29.3±0.2, 29.8±0.2, 30.6±0.3, 31.5±0.3, 31.9±0.2, 34.2±0.3, and 35.4±0.3, wherein the XRD is obtained using CuKα radiation.

Element E8: Wherein the catalyst has a 35% conversion temperature from about 350° C. to about 425° C.

Element E9: Wherein providing the aqueous mixture including molybdenum and vanadium includes combining an aqueous mixture including molybdenum and an aqueous mixture including vanadium.

Element E10: Wherein providing the aqueous mixture including molybdenum and vanadium includes combining an aqueous mixture including molybdenum and an aqueous mixture including vanadium; and wherein the aqueous mixture including molybdenum is prepared from at least $(NH_4)_6Mo_7O_{24} \cdot 4H_2O$ and a first water.

Element E11: Wherein providing the aqueous mixture including molybdenum and vanadium includes combining an aqueous mixture including molybdenum and an aqueous mixture including vanadium; and wherein the aqueous mixture including vanadium is prepared from at least $VOSO_4 \cdot XH_2O$ and a second water.

Element E12: Wherein the aqueous mixture including molybdenum and vanadium further includes a surfactant.

Element E13: Wherein the aqueous mixture including molybdenum and vanadium further includes a surfactant; and wherein the surfactant is selected from a non-ionic surfactant, an anionic surfactant, a cationic surfactant, or a combination thereof.

Element E14: Wherein the aqueous mixture including molybdenum and vanadium further includes a surfactant; and wherein the surfactant includes a surfactant selected from sodium dodecyl sulfate, sodium decyl sulfate, sodium tetradecyl sulfate, sodium pentadecyl sulfate, sodium heptadecyl sulfate, sodium octyl sulfate, sodium oleate, sodium laurate, sodium 2-ethylhexyl sulfate, potassium stearate, calcium oleate, ammonium dodecyl sulfate, or a combination thereof.

Element E15: Wherein the aqueous mixture including molybdenum and vanadium further includes a surfactant; and wherein the surfactant includes sodium dodecyl sulfate.

Element E16: Wherein the aqueous mixture including molybdenum and vanadium further includes a surfactant; and wherein the surfactant includes sodium octyl sulfate.

Element E17: Wherein hydrothermally reacting the mixture to form the precalcined catalyst includes heating the aqueous mixture of molybdenum and vanadium in the presence of a catalyst seed.

Element E18: Wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium.

Element E19: Wherein hydrothermally reacting the mixture to form the precalcined catalyst includes heating the aqueous mixture of molybdenum and vanadium in the presence of a catalyst seed; and wherein the catalyst seed includes a composition including molybdenum and vanadium; and wherein the composition including molybdenum and vanadium includes a catalyst including molybdenum, vanadium, and oxygen, wherein the molar ratio of molybdenum to vanadium in the catalyst is from 1:0.15 to 1:0.75.

Element E20: Wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium.

Element E21: Wherein hydrothermally reacting the mixture to form the precalcined catalyst includes heating the aqueous mixture of molybdenum and vanadium in the presence of a catalyst seed; and wherein the catalyst seed includes a composition including molybdenum, vanadium, niobium, and tellurium; and wherein the composition including molybdenum, vanadium, niobium, and tellurium includes a catalyst including molybdenum, vanadium, tellurium, niobium, and oxygen, wherein the molar ratio of molybdenum to vanadium is from 1:0.05 to 1:0.60, the molar ratio of molybdenum to tellurium is from 1:0.01 to 1:0.30, and the molar ratio of molybdenum to niobium is from 1:0.01 to 1:0.40, and wherein oxygen is present at least in an amount to satisfy the valency of any present metal oxides.

Element E22: Wherein hydrothermally reacting the mixture to form a precalcined catalyst includes heating the aqueous mixture of molybdenum and vanadium at a temperature from about 150° C. to about 300° C.

Element E23: Wherein hydrothermally reacting the mixture to form a precalcined catalyst includes heating the aqueous mixture of molybdenum and vanadium at a temperature from about 200° C. to about 250° C.

Element E24: Wherein hydrothermally reacting the mixture to form a precalcined catalyst includes heating the aqueous mixture of molybdenum and vanadium at a temperature of about 230° C.

Element E25: Wherein hydrothermally reacting the mixture to form a precalcined catalyst includes heating the aqueous mixture of molybdenum and vanadium under a pressure from about 1 psi to about 1,500 psi.

Element E26: Wherein hydrothermally reacting the mixture to form a precalcined catalyst includes heating the aqueous mixture of molybdenum and vanadium under a pressure from about 400 psi to about 440 psi.

Element E27: Wherein hydrothermally reacting the mixture to form a precalcined catalyst includes heating the aqueous mixture of molybdenum and vanadium at a temperature from about 200° C. to about 250° C. under a pressure from about 200 psi to about 900 psi.

Element E28: Wherein hydrothermally reacting the mixture to form a precalcined catalyst includes heating the aqueous mixture of molybdenum and vanadium at a temperature of about 230° C. under a pressure from about 400 psi to about 440 psi.

Element E29: Wherein hydrothermally reacting the mixture to form a precalcined catalyst includes contacting the mixture with a glass liner, stainless steel, or Teflon liner.

Element E30: Wherein hydrothermally reacting the mixture to form a precalcined catalyst includes contacting the mixture with a glass liner.

Element E31: Wherein hydrothermally reacting the mixture to form a precalcined catalyst includes contacting the mixture with a Teflon liner.

Element E32: Wherein the precalcined catalyst is calcined at about 300° C. to about 500° C.

Element E33: Wherein the precalcined catalyst is calcined at about 375° C. to about 425° C.

Element E34: Wherein the precalcined catalyst is calcined at about 400° C.

Element E35: Wherein the precalcined catalyst is calcined at about 300° C. to about 500° C. for about 1 hour to about 24 hours.

Element E36: Wherein the precalcined catalyst is calcined at about 375° C. to about 425° C. for about 1 hour to about 4 hours.

Element E37: Wherein the precalcined catalyst is calcined at about 400° C. for about 2 hours.

Element E38: Wherein the acid solution includes oxalic acid.

Element E39: Wherein the acid solution includes oxalic acid; and wherein the concentration of oxalic acid is from about 0.05 M to about 0.5 M.

By way of non-limiting example, exemplary element combinations applicable to Embodiment E include: E1 and E3; E1 and E4; E1, E3, and E5; E1, E3, and E8 E1, E3, E10, and E11; E1, E3, E10, E11, and E38; and E1, E3, E10, E11, and E39.

EXAMPLES

General Procedures:
Reagents

Reagents purchased from manufacturers were used as received, without further purification. All reagents, with the exception of alumina, were purchased from Sigma Aldrich®. The supplied certificates of analysis were used to establish the hydrate content for Ammonium molybdate (($NH_4$)$_6Mo_7O_{24}$·$4H_2O$) and vanadium (IV) oxide sulfate hydrate ($VOSO_4$·$3.46H_2O$ and $VOSO_4$·$3.36H_2O$).

Distilled water was prepared inhouse using a CORNING® MEGA-PURE® 12A System ACS as distillation apparatus.

MRU

The ability of catalysts described herein to participate in the oxidative dehydrogenation of ethane were tested in a microreactor unit (MRU).

The MRU included a reactor tube made from SS316L stainless-steel SWAGELOK® Tubing, which had an outer diameter of 0.5 inches, an internal diameter of about 0.4 inches, and a length of about 15 inches. A 6-point WIKA Instruments Ltd. K-type thermocouple having an outer diameter of 0.125 inches was inserted axially through the center of the reactor, which was used to measure and control the temperature within the catalyst bed. A room temperature glass tight sealed condenser was located after the reactor to collect water/acidic acid condensates. The gas product flow was allowed to either vent or was directed to a gas chromatography (Agilent 6890N Gas Chromatograph, using CHROMPERFECT®—Analysis, Version 6.1.10 for data evaluation) via a sampling loop.

To prepare catalyst and catalyst materials for testing in the MRU, the catalyst or catalyst material was loaded into a 1-inch round die and pressed with 8 tons of compression force for 10 to 15 seconds of dwelling time. The pressed catalyst or catalyst material was then crushed into small pieces using a mortar and pestle. The crushed catalyst or catalyst material was sieved and a particle sizes between 425 μm and 1 mm were collected to be loaded for testing on the MRU.

Figure 9:
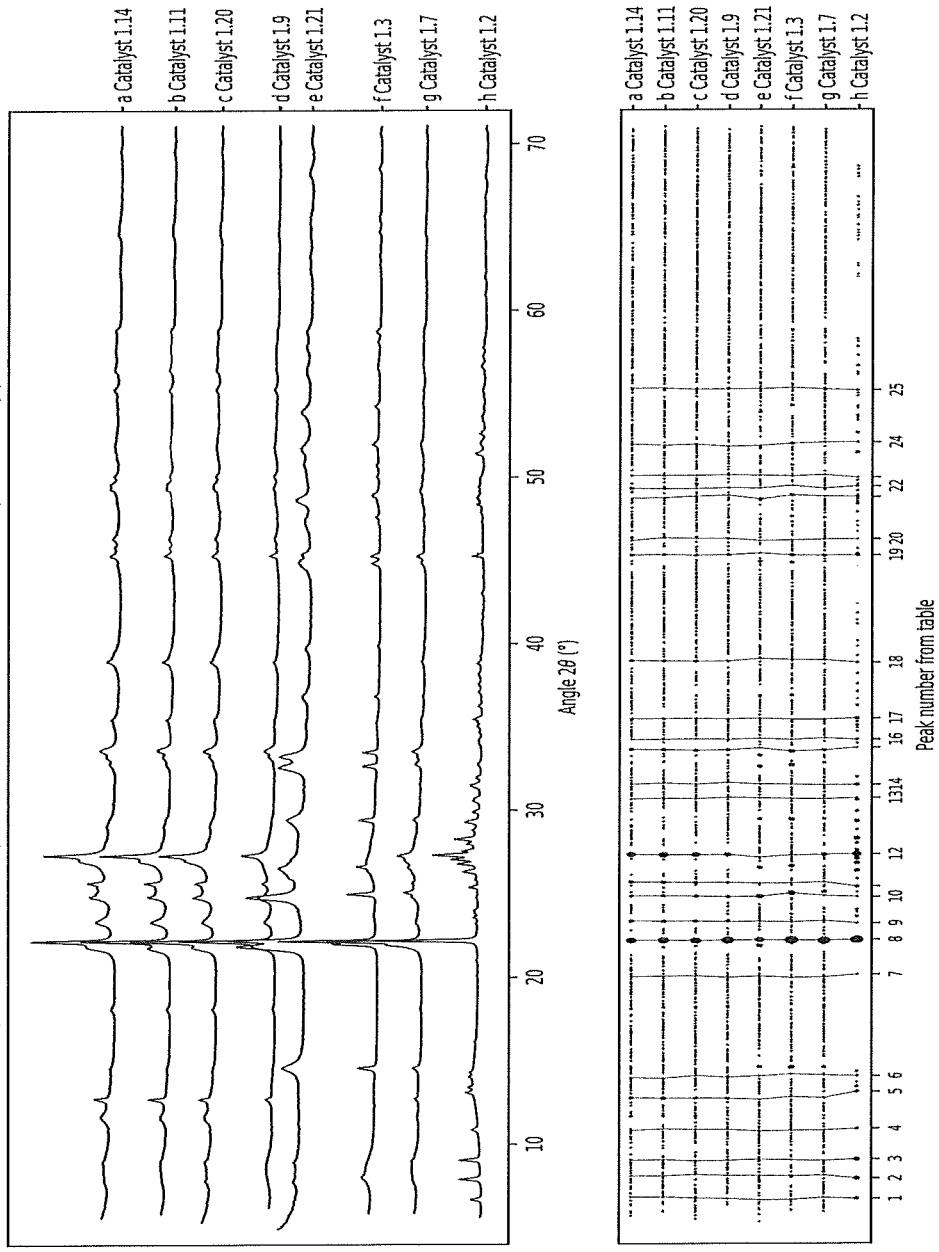
FIG. 9 shows PXRD stacked plots and peaks prominence plot for select samples.
Figure 10:
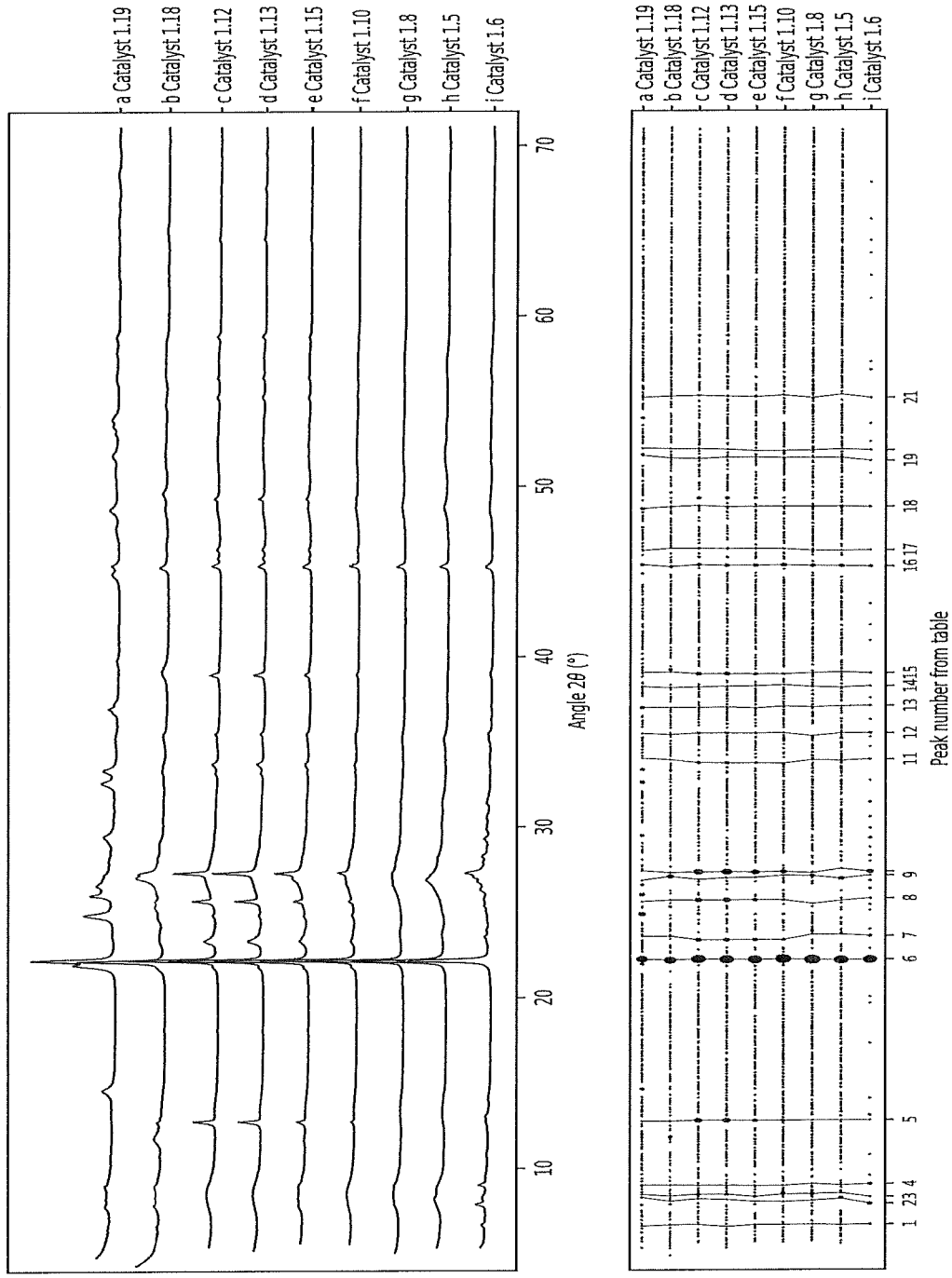
FIG. 10 shows PXRD stacked plots and peaks prominence plot for select samples.
Figure 11:
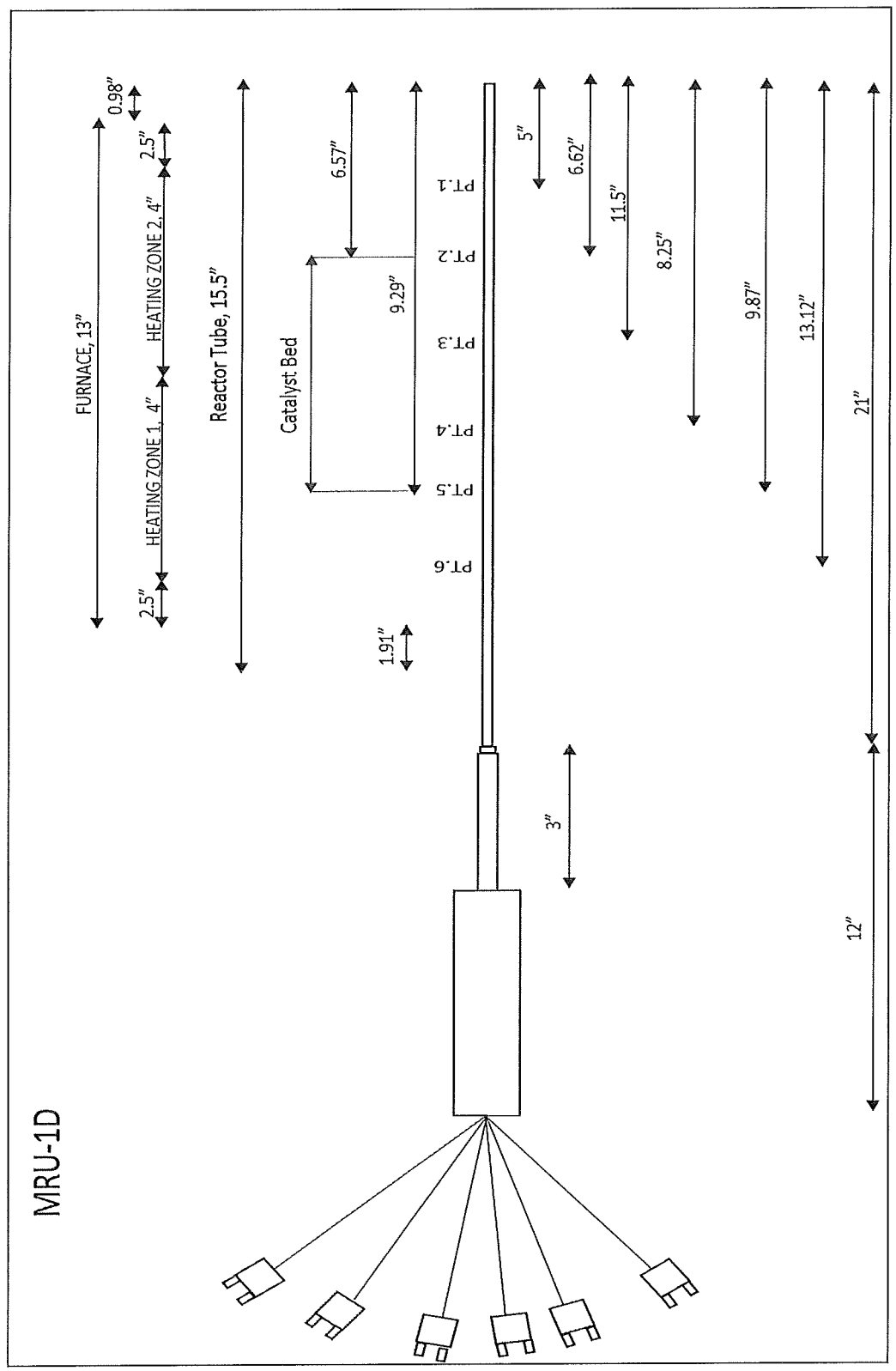
FIG. 11 shows the drawing of Reactor 1 discussed in the examples.
Figure 12:
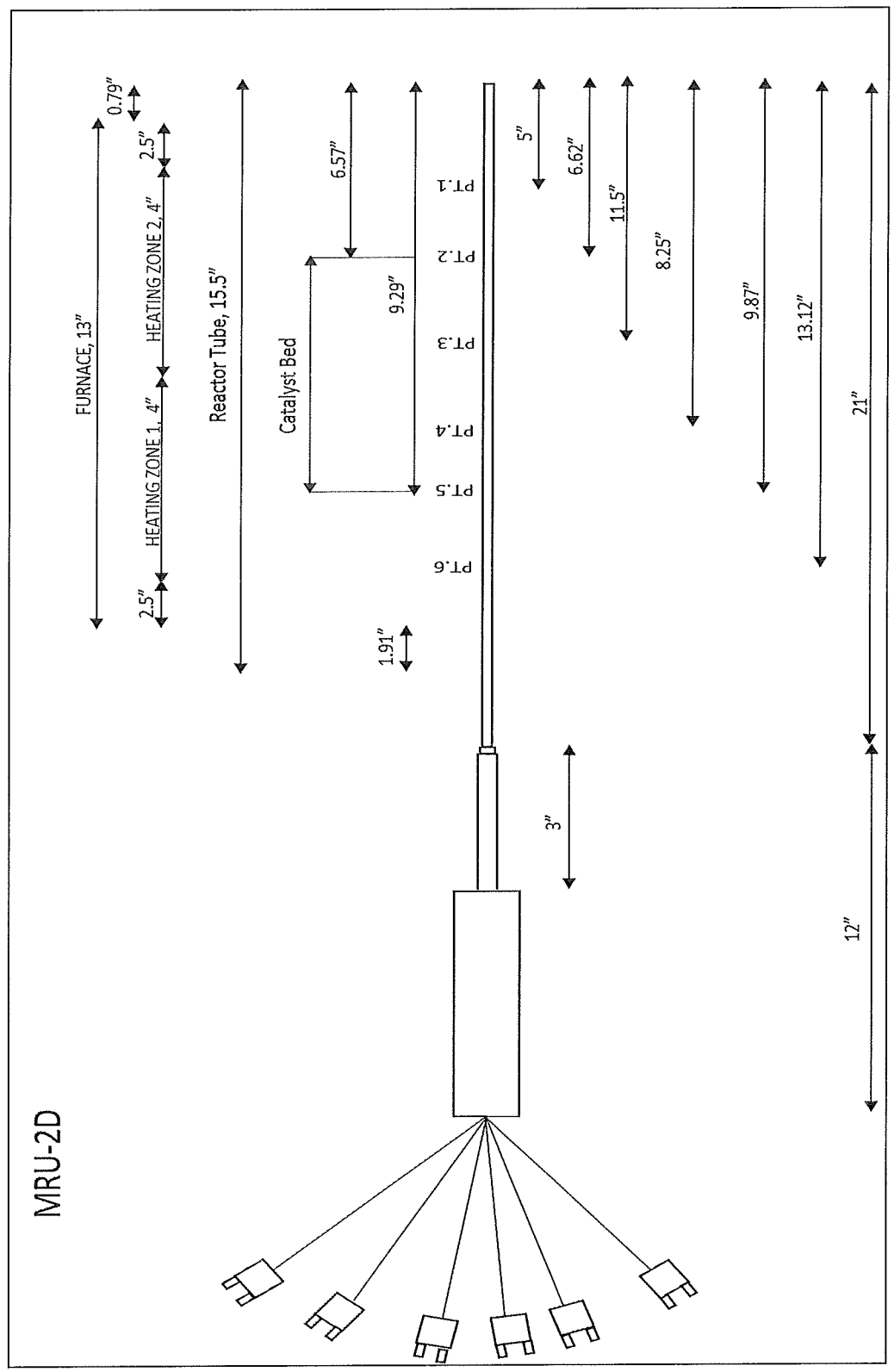
FIG. 12 shows the drawing of Reactor 2 discussed in the examples.

For MRU experiments, the catalyst bed was prepared by physically mixing 2.00 g of catalyst with quartz sand such that the catalyst bed had a total volume of about 6 mL. The catalyst bed was loaded in the middle zone of the reactor—located between points 2 and 5 of the thermocouple—and the remaining volume of the reactor was packed with quartz sand (FIGS. 9 and 10). The load was then secured with glass wool on the top and the bottom of reactor.

For the MRU testing, a pre-mixed feed gas was fed through the reactor. The pre-mixed feed gas entering the reactor was 36 mol. % ethane, 18 mol. % oxygen, and 46 mol. % nitrogen. Further, the pre-mixed feed gas flow was adjusted by a calibrated mass flow controller to obtain a gas hourly space velocity (GHSV) of about 3,000 $h^{-1}$, based on the catalyst volume in the catalyst bed.

The flow rate of the feed gas was between about 70 standard cubic centimeters per minute (sccm) to about 80 sccm (e.g., about 74.6 sccm). The catalyst bed placed in the reactor tube can include the catalyst or catalyst material and a filler. With reference to the MRU's catalyst bed, a filler refers to a material that does not participate in the oxidative dehydrogenation of ethane or have other catalytic activity, such as non-selective oxidation under the MRU test conditions. The filler was quartz sand. The ratio of catalyst or catalyst material to filler was 1:1 (by volume). The 35% conversion temperature was determined at a weight hourly space velocity (WHSV) of 2.90 $h^{-1}$, with the WHSV based on the amount of catalyst or the amount of catalyst used to prepare the catalyst material, and a gas hourly space velocity (GHSV) of about 3,000 $h^{-1}$. Whereby WHSV is defined as mass flow of feed gas to the reactor divided by the weight of the catalyst in the catalyst bed, GHSV is defined as volumetric flow of the reactor feed gas divided by the volume of the catalyst bed.

Typically, the inlet pressure was in the range of about 1 pound per square inch gauge (psig) to about 2.5 psig and the outlet pressure was in the range of about 0 psig to about 0.5 psig. The gas feed exiting the catalyst bed was be analyzed by gas chromatography to determine the percent of various hydrocarbons (e.g., ethane and ethylene) and, optionally other gases such as $O_2$, $CO_2$, and CO.

The gas exiting the reactor was analyzed by gas chromatography (Agilent 6890N Gas Chromatograph, using CHROMPERFECT®—Analysis, Version 6.1.10 for data evaluation) to determine the percent of various hydrocarbons (e.g., ethane and ethylene) and, optionally other gases such as $O_2$, $CO_2$, and CO and acetylene.

A catalyst or 35% conversion temperature was determined as follows. Conversion of the feed gas was calculated as a mass flow rate change of ethane in the product compared to feed ethane mass flow rate using the following formula:

$$C = \left( \frac{2 * X_{Ethylene} + X_{CO2} + X_{CO}}{2 * X_{Ethylene} + 2 * X_{Ethane} + X_{CO2} + X_{CO}} \right) * 100\%$$

In the above equation, C is the percent of feed gas that has been converted from ethane to another product (i.e., ethane conversion) and X is the molar concentration of the corresponding compound in the gaseous effluent exiting the reactor at corresponding temperature. The ethane conversion was then plotted as a function of temperature to acquire a linear algebraic equation. The linear equation for ethane conversion was solved to determine the temperature in which the ethane conversion was 35% (i.e. the 35% conversion temperature).

Further, the gas exiting the reactor was analyzed by gas chromatography to determine catalyst selectivity to ethylene (i.e., the percentage on a molar basis of ethane that forms ethylene). Selectivity to ethylene was determined using the following equation:

$$S_{Ethylene} = \left( \frac{2 * X_{Ethylene}}{2 * X_{Ethylene} + X_{CO2} + X_{CO}} \right) * 100\%$$

In the above equation, $S_{Ethylene}$ is the selectivity to ethylene and X is the molar concentration of the corresponding compound in the gaseous effluent exiting the reactor at corresponding temperature. The selectivity to ethylene was determined at the 35% conversion temperature, unless otherwise indicated. As such, after the 35% conversion temperature was determined, the above equation for selectivity was solved using the corresponding values for $X_{Ethylene}$, $X_{CO2}$, and $X_{CO}$ at the 35% conversion temperature.

When reported, acetic acid production was determined by running MRU testing long enough to collect an aqueous condensate in the condenser (e.g., 1-3 days). After collecting a sample of the condensate, the sample was submitted for liquid GC analysis (Agilent 6890N Gas Chromatograph, Using CHROMPERFECT®—Analysis, Version 6.1.10 for data evaluation). To perform the liquid GC analysis, 300-450 mg of liquid sample was transferred to a scintillation vial. Next, 25 mg of isopropanol (IPA) was added as an internal standard. Further, 18-20 mL of distilled $H_2O$ was added to dilute the sample. Prepared samples were then transferred to GC vials and set in sequence to tested using an auto sampler. The GC analysis was a split injection method with a temperature program and FID detector. Further, a set of 3 calibration standards were run in duplicate for the relative response factor used for calculating acetic acid content in sample.

ICP-MS

Inductively Coupled Plasma Mass Spectrometry (ICP-MS), sensitive enough to detect elements in ppb concentration ranges, was the analytical technique used for measuring the elemental composition of catalyst or catalyst materials. ICP-MS analysis was performed on an Agilent 7700X ICP-MS system. Quantitative determination of atoms' concentration in the original sample was determined with the use of an external standard calibration. The calibration curves were constructed after subtracting the reagent blank. Concentrations were given in ng/mg (wt-ppm) or μg/g (wt-ppm) units in this analysis.

Samples were prepared by placing 10 milligram (mg) of catalyst or catalyst material in either 3 milliliters (mL) of 10-15 wt. % NaOCl solution or 3 mL of a 6.25-35.0 molar (M) NaOH solution. The solution was then heated in an oil bath at 90° C. with rigorous mixing.

ICP Digestion Method:

Catalyst materials were digested in an oxalic acid solution to produce a suitable homogenous sample for ICP-MS.

Approximately 10 mg of catalyst material and 2-3 g of oxalic acid were added to a vial. Then, 2-3 mL of distilled water was added to create a suspension. The suspension was heated in an oil bath at 90° C. with rigorous mixing. Dissolution of the catalyst generally took 24-72 hours to produce a homogenous, blue solution. After dissolution was complete, the resulting solution was diluted to a final volume of 60-80 mL. The diluted solution was then further diluted 10-100× using 5% nitric acid and analyzed by ICP-MS.

The multi-element scan optimizes the instrument parameters to scan for trace (ppb) levels of 50+ elements. The 50+ elements included in the multi-element scan. When scanning for the molybdenum and vanadium elements higher concentrations of calibration standards were used and the instrument sensitivity was reduced as the elements of interest were found in percent levels. This was done by preparing calibration standards for each of the two elements. These calibration standards were prepared in percentage levels in high concentrations. Normally calibration standards were prepared in ppm level concentrations. The ICP-MS program was developed such that only the two elements molybdenum and vanadium are detected with a high degree of accuracy. The elements that were normally calibrated to ppm level concentrations would be excluded as the detector was calibrated for only the four elements at high percentages.

XRD

Instrument

Powder X-Ray Diffractometry (PXRD) data was collected using a PANalytical Aeris X-ray diffractometer by SEMx Incorporated. This diffractometer instrument consisted of three basic elements: X-ray tube, sample holder, and X-ray detector. X-rays are generated in a cathode ray tube (Cu source with K$\alpha$ radiation=1.5418 Å) with the resulting X-rays being directed onto the sample. As the sample and detector were rotated, the intensity of the reflected X-rays was recorded to produce characteristic X-ray spectra. When the incident X-rays reflecting off the sample satisfies the Bragg Equation (n$\lambda$=2d sin $\theta$), constructive interference occurs and a peak in intensity occurs (y-axis). X-ray diffractometers were setup such that the sample rotates in the path of the X-ray beams at an angle $\theta$, while the X-ray detector is mounted on an arm to collect the diffracted X-rays and rotates at an angle of 2$\theta$ from ~5° to 70° (x-axis).

Qualitative XRD analysis and Rietveld Refinement was performed using HighScore Plus XRD analysis software. The samples were finely ground to reduce particle size and to obtain a uniform mixture. They were then loaded onto the XRD sample holder and the XRD spectrum was acquired. The Rietveld Refinement results were combined with HighScore Plus and EDS results to perform qualitative and quantitative analysis.

Amorphous Phase Determination

The weight percentage of amorphous phase was determined by external standard. With an external standard phase, the instrument intensity constant, K-factor, is determined. Corundum was used as the external standard and was measured with the same instrument configuration shortly after the unknown sample was measured. The K-factor approach is described by O'Connor and Raven: 1988, Powder Diffraction, 3 (1), 2-6. For each sample, the weight percentage of the crystalline MoVO$_x$ orthorhombic phase had to be determined in order to assign weight percentages to the amorphous phase. The Degree of Crystallinity (DOC) Method, based on the estimation that the total intensity of area contributed to the overall diffraction pattern by each component in the analysis, was used to determine the amount of amorphous phase. The degree of crystallinity was calculated from the total areas under the defined crystalline and amorphous components from:

$$DOC = \text{Crystalline Area} / (\text{Crystalline Area} + \text{Amorphous Area})$$

Where the weight fraction of the amorphous material was calculated from:

$$W_{amorphous} = 1 - DOC$$

The Ortho-MoVO$_x$ phase contributed to the crystalline area and therefore needed to be quantified in order to determine the amorphous area. To compensate for the fact that different materials and backgrounds would have different effects, a sample of MoVTeNbO$_x$ was used to calibrate some constants needed for the DOC method. Samples containing MoVO$_x$ phases had the ortho-MoVO$_x$ phase weight percentages qualitatively determined using only two elements (Mo and V) based on the MoVTeNbO$_x$ calibration.

M1 Phase Content Determination

Method A: The MoVO$_x$ orthorhombic phase (also referred to in literature as the M1 phase) was fitted using literature crystal structure reference 04-022-1665 in the HighScore Plus XRD analysis software.

Method B: The MoVO$_x$ orthorhombic phase (also referred to in literature as the M1 phase) was fitted using literature crystal structure data for a crystallographically similar compound.

MoVO$_x$ XRD simulation were performed as described in S. Ishikawa, D. Kobayashi, T. Konya, T. Murayama, N. Yasuda, M. Sadakane, W. Ueda. *J. Phys. Chem. C*, 119, 7195, (2015).

The lattice parameters utilized were: a=21.0083 Å, b=26.4755 Å, c=4.0111 Å.

Comparative Raw Data Analysis

The PXRD raw data was also analyzed using a Python code through the program Spyder. The code generated overlaid plots. It also analyzed the data by comparing the peak prominence of all the local maxima and generated a plot with peaks meeting an established threshold. Relevant catalyst peaks are highlighted in the plot with vertical lines and the range of the relative peak intensities were provided by the code.

SEM

Scanning electron microscope (SEM) images were collected using a JSM-IT300LV InTouchScope. The sample was prepared on an aluminum stud with double sided carbon tape. The sample was scanned on an SEM stage.

SEM-EDS

Energy-dispersive X-ray spectroscopy (EDS) was conducted using a JEOL JED-2300 DRY SDD EDS detector. Samples were sent to SEMx Incorporated for EDS analysis. The samples were finely ground to reduce particle size and obtain the uniform mixture. They were then loaded onto EDS stub for analysis by SEM. EDS was used for elemental analysis and surface examination. EDS is a micro-analytical technique that provides a semi-quantitative elemental analysis of the surface of a sample (e.g. the top 1 to 3 microns). The SEM is used to examine the surface morphology at magnifications ranging from 20 to 100,000 times. The EDS instrument can detect elements with an atomic number equal or greater than sodium, but also has light element capability, which means that it can also detect carbon, nitrogen, oxygen, and fluorine. The estimated lower detectable limit for any given element generally is between about 0.2 and 0.5 wt. %.

PSD by SEM

Samples were sent to SEMx Incorporated for particle size analysis using scanning electron microscopy (SEM), model JEOL-JSM300 LV. SEM was used to observe and count the particles in the sample to obtain the Particle Size Distribution (PSD). For the PSD measurements, the SEM instrument took pictures at different magnifications. Measurements are done for 400-800 particles at different magnifications to cover the size range (statistical population). Size is measured by length in micrometers and is measured on the longest dimension of the particles. SEM based PSD is the preferred method for analyzing samples where particles are agglomerated (stuck together) because the analyst can visually see this through the microscope and make the judicious decision to measure the distinct particles rather than the agglomerates. Statistics and analysis were based on total counts measured by SEM.

Pore Volume, BET Surface Area Analysis and BJH Pore Size Distribution Analysis Gas adsorption manometry is the method that was used for the determination of adsorption isotherms of nitrogen at the temperature of liquid nitrogen (~77 K). The amount of gas adsorbed was evaluated by measuring the change in gas pressures. Isothermal nitrogen adsorption processes are measured, and surface areas and volumes were calculated through the application of various theories/equations.

Total pore volume was calculated by nitrogen gas uptake at the relative pressure $P/P_0=0.99$.

Brunauer-Emmett-Teller (BET) analysis was applied to quantify the specific surface area ($m^2/g$) of the solid samples. BET valuations were performed by multilayer adsorption of nitrogen and measured as a function of relative pressure. Since different solids can have drastically different isotherm shapes, they are difficult to compare. Applying BET theory allows for a more quantitative comparison of solids' surface areas by determining the so-called monolayer capacity from nitrogen multilayer adsorption experiment. Monolayer capacity is a representation of total specific surface area and encompasses both the external area and pore area of porous solid.

Barrett-Joyner-Halenda (BJH) method was used for calculating pore size (Å) distributions from experimentally collected adsorption isotherms using the Kelvin model of pore filling ($cm^3/g·A$). This technique characterizes pore size distribution independently of external area due to particle size of the sample and can be applied to mesopore and small macropores.

Nitrogen physisorption experiments were performed on a TriStar (Micromeritics Instruments) by the University of Calgary. Samples were analyzed by nitrogen adsorption at 77 K. The as-received samples were loaded into physisorption cells. The samples were degassed at 200° C. for 1 h prior to the adsorption experiments.

Synthetic Details:

Example 1: Synthesis of Catalyst 1.1

A solution of $(NH_4)_6Mo_7O_{24}·4H_2O$ (8.83 g, 7.14 mmol, white solid) in 120 mL of $dH_2O$ was prepared in a 600-mL glass liner equipped with magnetic stir bar. A solution of $VOSO_4·3.46H_2O$ (2.81 g, 12.47 mmol, bright blue solid) in 120 mL of $dH_2O$ was prepared in a 250-mL beaker equipped with a magnetic stir bar. Both solutions were stirred in a 60° C. water bath until homogeneous. The blue vanadium solution was then added slowly to the clear colorless molybdenum solution. This resulted in a dark purple solution with a fine suspension. Sodium dodecyl sulfate (2.71 g, 9.39 mmol, white solid) was added to the reaction mixture. The slurry was left to stir at 60° C. for 30 minutes.

The liner was loaded into a 600-mL Parr reactor and the gap filled with $dH_2O$. The reactor was sealed and the head space evacuated and backfilled with $N_2$ gas 10× times. The headspace was left under 15 psig $N_2$ gas and sealed. The reactor was loaded into an oven at 230° C. for 20 hours (1-hour ramp to reaction temperature) without stirring. Once cooled to room temperature, the reactor was vented, and the contents were filtered using a Buchner funnel and 4 quantitative filter papers. The filter cake was rinsed with 500 mL of $dH_2O$ and 500 mL of ethanol. The filtrate was a dark blue color and the product was a grey color.

The grey product was transferred to a 200 mL RBF equipped with a stir bar, along with 50 mL of $dH_2O$. In a 100 mL beaker, 4 g of oxalic acid was dissolved in 50 mL of $dH_2O$. The oxalic acid solution was transferred to the 200-mL RBF. The mixture was stirred (500 rpm) at 80° C. for 40 mins. The mixture was allowed to cool for 15 minutes, before being filtered using a Buchner funnel and 4 quantitative filter papers. The filter cake was rinsed with 500 mL of $dH_2O$.

The filter cake was dried in the oven at 90° C. overnight. The dry powder product was ground manually with a mortar and pestle. The powder was divided into two portions, half being calcined in a quartz spilt tube at 400° C., the other half being calcined in a quartz spilt tube at 600° C. Both calcinations occurred under nitrogen atmosphere. The portion calcined at 400° C. was characterized and examined as described in this disclosure.

Figure 6:
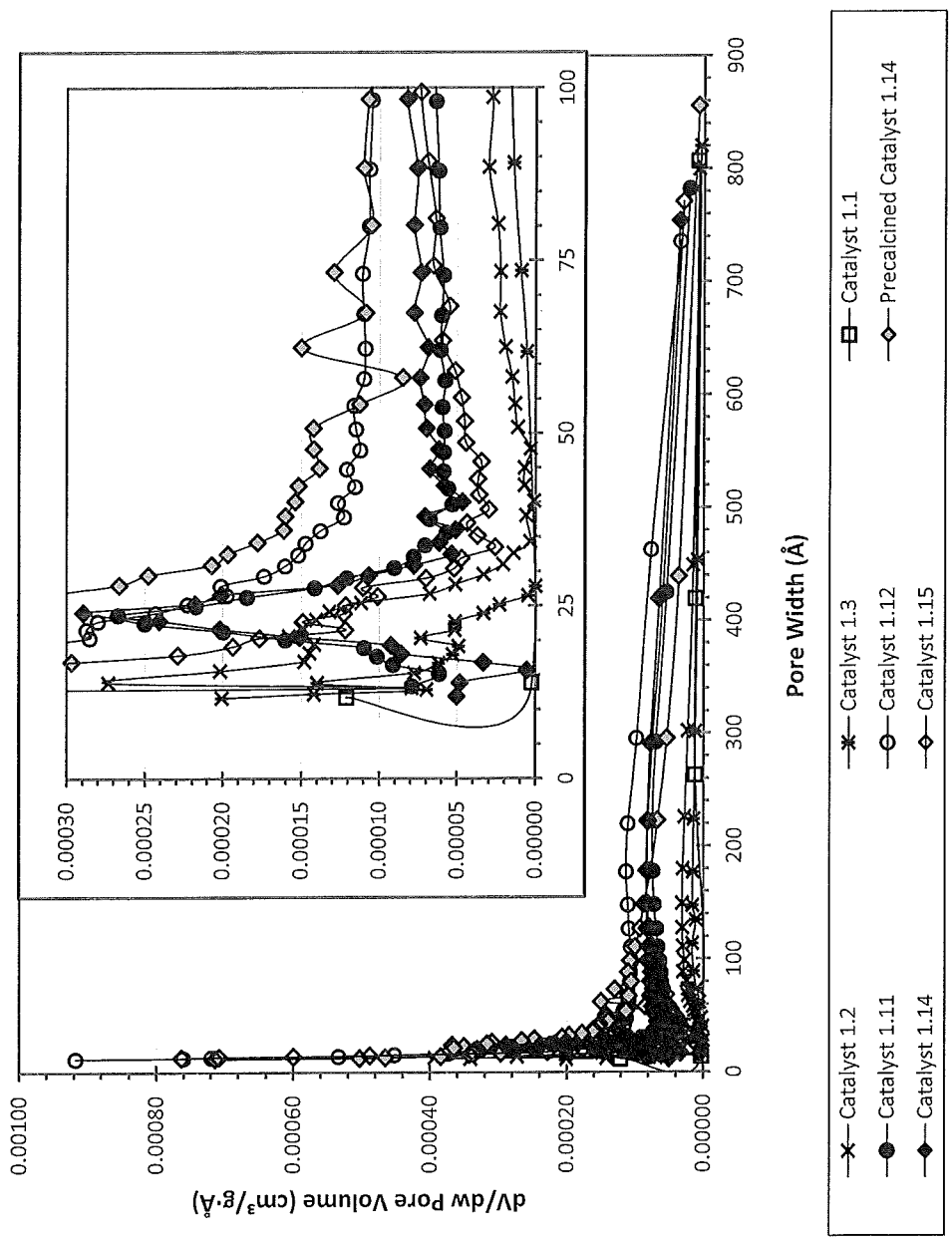
FIG. 6 shows BJH Pore size distribution.
Figure 8:
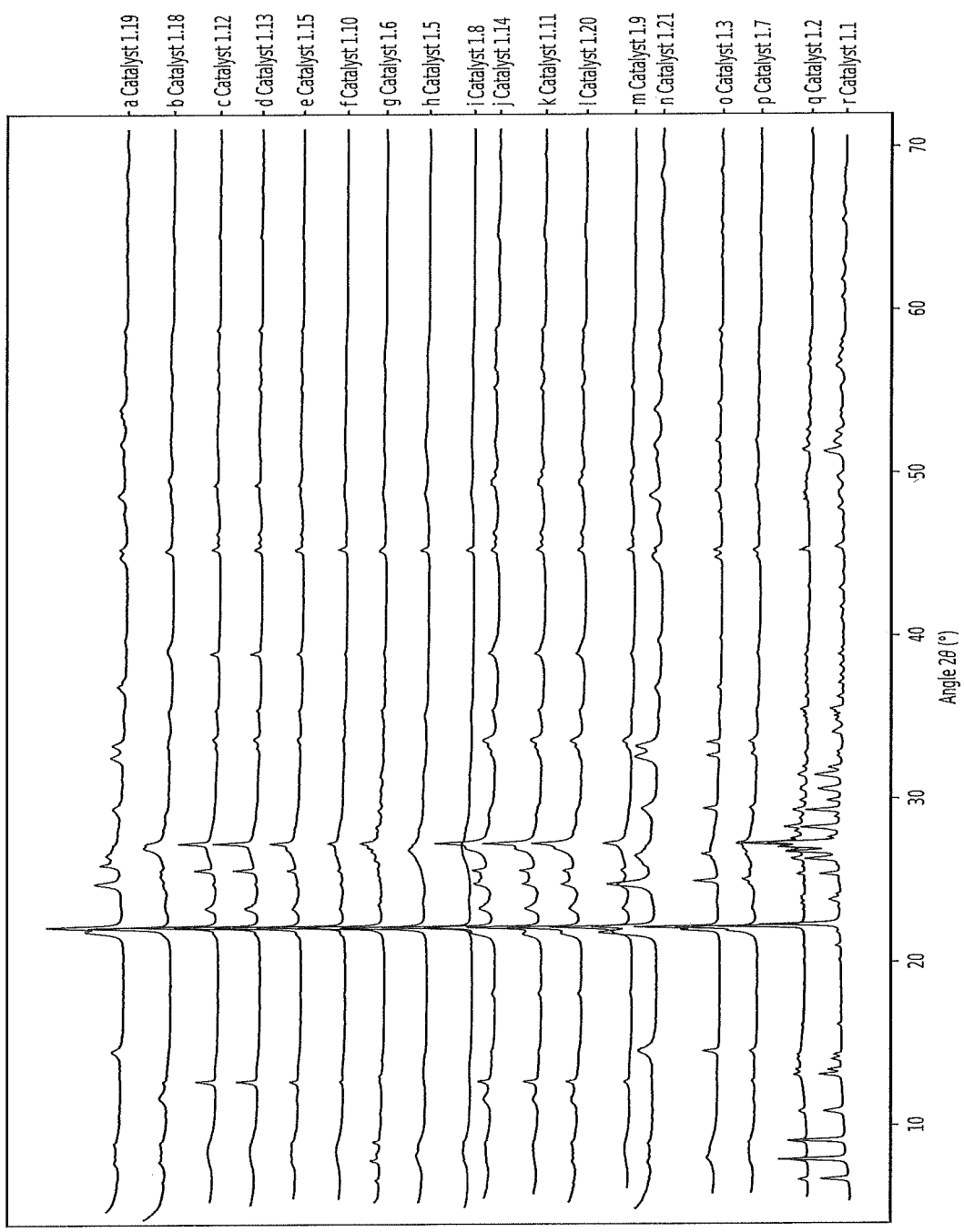
FIG. 8 shows PXRD stacked plots for select catalysts and a comparative baseline.

Characterization: The activity for Catalyst 1.1 is presented in Table 1. BET surface area and pore volume data are presented in Table 3. The BJH Pore size distribution curve is presented in FIG. 6. SEM-EDS elemental analysis is presented in Table 4. XRD calculated phases and amorphous phase is presented in Table 6a. The XRD diffractogram is presented in FIG. 8. ICP-MS elemental analysis is presented in Table 9.

Example 2: Synthesis of Catalyst 1.2

A solution of $(NH_4)_6Mo_7O_{24}·4H_2O$ (13.26 g, 10.73 mmol, white crystalline solid) in 120 mL of $dH_2O$ was prepared in a 500-mL RBF equipped with magnetic stir bar. A solution of $VOSO_4·3.46H_2O$ (7.21 g, 32.00 mmol, bright blue crystalline solid) in 120 mL of $dH_2O$ was prepared in a 250-mL beaker equipped with magnetic stir bar. Both solutions were stirred in a 60° C. water bath until homogeneous. The blue vanadium solution was then added dropwise to the clear colorless molybdenum solution. This resulted in a dark burgundy solution with a fine suspension. Solid sodium dodecyl sulfate (SDS) (4.05 g, 14.04 mmol, white solid) was added to the mixture. The slurry was left to stir at 60° C. for 30 minutes.

The reaction mixture was transferred to a glass liner. The liner was loaded into a 600-mL Parr reactor and the gap filled with $dH_2O$. The reactor was sealed and the head space evacuated and backfilled with $N_2$ gas 10× times. The headspace was left under 15 psig $N_2$ gas and sealed. The reactor was heated to 230° C. using a heating mantel and jacket insulation for 20 h. Once cooled to room temperature, the reactor was vented, and the contents filtered using a Buchner funnel and 4 quantitative filter papers. The filter cake was rinsed with $dH_2O$. The product was dense compared to the baseline.

The filter cake was dried in the oven at 90° C. overnight. The dry powder product was ground manually with mortar and pestle.

Figure 7:
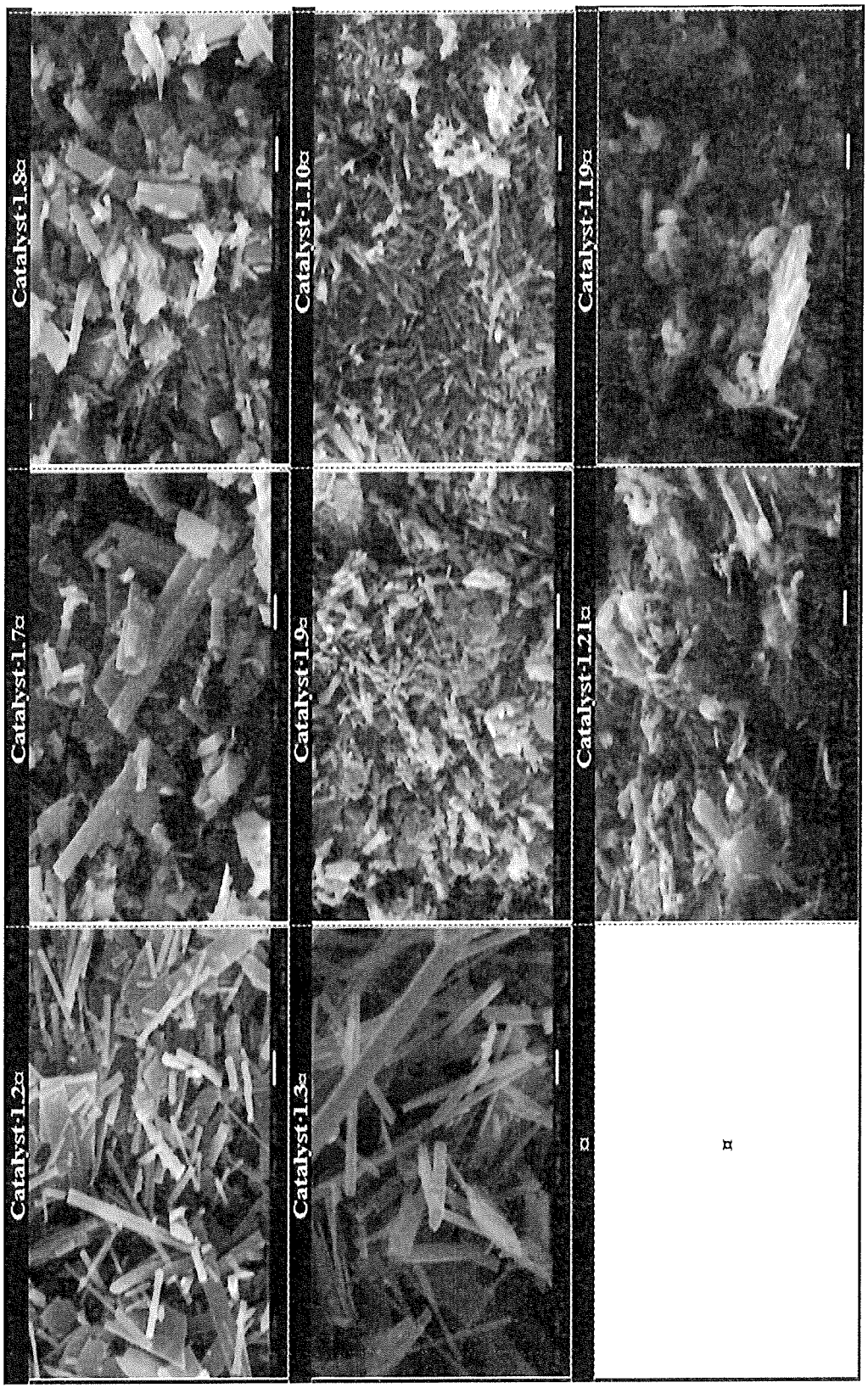
FIG. 7 shows images of select catalyst at 10,000× magnification.
Figure 7:
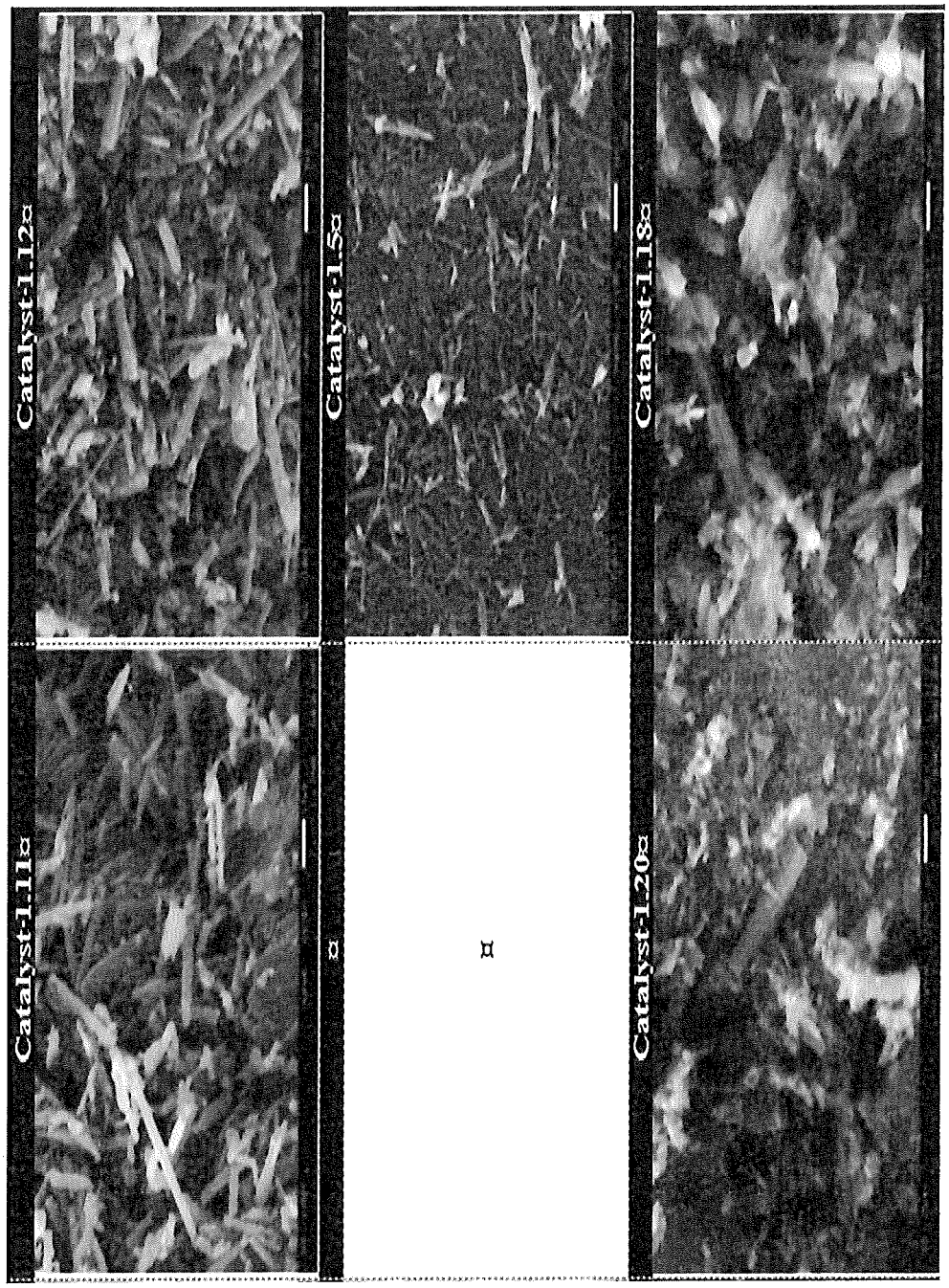

Characterization: The activity for Catalyst 1.2 is presented in Table 1. Particle size distribution statistical data is presented in Table 2. Particle size distribution graph is presented in FIG. 1. BET surface area and pore volume data are presented in Table 3. The BJH Pore size distribution curve is presented in FIG. 6. SEM-EDS elemental analysis is presented in Table 4. An SEM image at 10,000× magnification is presented in FIG. 7. XRD calculated phases and amorphous phase are presented in Tables 6a and 6b. The XRD diffractogram is presented in FIG. 8. The XRD diffractogram with corresponding peak prominence plot is presented in FIG. 9. The XRD ranges of peaks identified in prominence plot are presented in Table 8. The ICP-MS elemental analysis is presented in Table 9.

Example 3: Synthesis of Catalyst 1.3

A solution of $(NH_4)_6Mo_7O_{24}·4H_2O$ (13.26 g, 10.73 mmol, white crystalline solid) in 180-mL of $dH_2O$ was prepared in a 500-mL RBF equipped with a magnetic stir bar. A solution of $VOSO_4·3.46H_2O$ (7.21 g, 32.00 mmol, bright blue crystalline solid) in 180 mL of dH$_2$O was prepared in a 250-mL beaker equipped with magnetic stir bar. Both solutions were stirred in a 60° C. water bath until homogeneous. The blue vanadium solution was then added to the clear colorless molybdenum solution. This resulted in a dark burgundy solution with a fine suspension. The slurry was left to stir at 60° C. for 30 minutes.

The reaction mixture was transferred to a glass liner equipped with magnetic stir bar. The liner was loaded into a 600-mL Parr reactor and the gap filled with dH$_2$O. The reactor was sealed and the head space evacuated and backfilled with N$_2$ gas 10× times. The headspace was left under 15 psig N$_2$ gas and sealed. The reactor was loaded into an oven at 230° C. overnight (1-hour ramp to reaction temperature) without stirring. Once cooled to room temperature, the reactor was vented, and the contents filtered using a Buchner funnel and 4 quantitative filter papers. The filter cake was rinsed with dH$_2$O. The product was dense compared to the baseline.

The filter cake was dried in the oven at 90° C. overnight. The dry powder product was ground manually with mortar and pestle.

The product was calcined in a quartz spilt tube at 400° C. under nitrogen atmosphere.

Characterization: The activity for Catalyst 1.3 is presented in Table 1. BET surface area and pore volume data is presented in Table 3. The BJH Pore size distribution curve is presented in FIG. 6. SEM-EDS elemental analysis is presented in Table 4. The SEM image at 10,000× magnification is presented in FIG. 7. XRD calculated phases and amorphous phase are presented in Tables 6a and 6b. The XRD diffractogram presented in FIG. 8. The XRD diffractogram with corresponding peak prominence plot is presented in FIG. 9. The XRD ranges of peaks identified in prominence plot are presented in Table 8. The ICP-MS elemental analysis is presented in Table 9.

Example 4: Synthesis of Precalcined Catalyst 1.4

A solution of (NH$_4$)$_6$Mo$_7$O$_{24}$.4H$_2$O (26.52 g, 21.46 mmol, white crystalline solid) in 100 mL of dH$_2$O was prepared in a 500-mL RBF equipped with magnetic stir bar. A solution of VOSO$_4$.3.36H$_2$O (14.50 g, 64.87 mmol, bright blue crystalline solid) in 90 mL of dH$_2$O was prepared in a 250-mL beaker equipped with magnetic stir bar. Both solutions were stirred in a 60° C. water bath until homogeneous. The blue vanadium solution was then added to the clear colorless molybdenum solution. This resulted in a dark burgundy solution with a fine suspension. The slurry was left to stir at 60° C. for 30 minutes.

The reaction mixture was transferred to a glass liner equipped with magnetic stir bar. The liner was loaded into a 600-mL Parr reactor and the gap filled with dH$_2$O. The reactor was sealed and the head space evacuated and backfilled with N$_2$ gas 10× times. The headspace was left under 15 psig N$_2$ gas and sealed. The reactor was connected to a magnetic stir plate. A heating mantel and insulation were used to heat the reaction for 26 hours at 232° C. (heating mantel controller set to 235° C.). Once cooled to room temperature, the reactor was vented, and the contents filtered using a Buchner funnel and 4 qualitative filter papers. The filter cake was rinsed with 1.8 L of dH$_2$O. The product was a dark purple color.

The filter cake was dried in the oven at 90° C. overnight with 26.08 g of product being recovered (98% estimated yield). The dry powder product was ground manually with mortar and pestle.

Example 5: Synthesis of Catalyst 1.5

The ground powder from Precalcined Catalyst 1.4 (10.00 g) was loaded into a beaker and calcined in a programmable muffle furnace: ramp 30 minutes to 280° C., dwell at 280° C. for 30 minutes, ramp 30 minutes to 400° C., dwell at 400° C. for 6 hours, cool to room temperature without control. There was 9.30 g of catalyst recovered after calcination.

An oxalic acid solution was prepared by dissolving 10.00 g of oxalic acid dehydrate in 100 mL of distilled water within a 500 mL RBF equipped with magnetic stir bar. To the solution was added the 9.30 g of calcined Precalcined Catalyst 1.4. The solution was allowed to stir for 6 hours. The contents of the RBF were filtered using a Buchner funnel and 4 quantitative filter papers. The filter cake was rinsed with dH$_2$O until clear. The filtrate was an emerald green color and the product was a very fine grey powder.

The filter cake was dried in the oven at 90° C. overnight with 1.07 g of catalyst being recovered (11% yield). The dry powder product was a very fine grey powder.

Characterization: An SEM image at 10,000× magnification is presented in FIG. 7. SEM-EDS elemental analysis is presented in Table 4. XRD calculated phases and amorphous phase are presented in Tables 7a and 7b. An XRD diffractogram is presented in FIG. 8. The XRD diffractogram with corresponding peak prominence plot is presented in FIG. 10. The XRD ranges of peaks identified in prominence plot are presented in Table 8. ICP-MS elemental analysis is presented in Table 11.

Example 6: Synthesis of Catalyst 1.6

The ground powder from Precalcined Catalyst 1.4 (8.45 g) was loaded into a beaker and calcined in a muffle furnace and calcined at 400° C. for 2 hours, before being cool to room temperature without control. There was 8.00 g of green catalyst recovered after calcination.

An oxalic acid solution was prepared by dissolving 3.00 g of oxalic acid dehydrate in 100 mL of distilled water within a 500 mL RBF equipped with magnetic stir bar. To the solution was added the 8.45 g of calcined Precalcined Catalyst 1.4. The solution was allowed to stir in an 80° C. oil bath for 3 hours. The contents of the RBF were filtered using a Buchner funnel and 4 quantitative filter papers. The filter cake was rinsed with 200 mL of dH$_2$O. The filtrate was an emerald green color and the product was a very fine grey powder.

The filter cake was dried in the oven at 90° C. overnight. The dry powder product was very fine grey powder.

Characterization: The activity for Catalyst 1.6 is presented in Table 1. SEM-EDS elemental analysis is presented in Table 4. XRD calculated phases and amorphous phase are presented in Tables 7a and 7b. An XRD diffractogram is presented in FIG. 8. The XRD diffractogram with corresponding peak prominence plot is presented in FIG. 10. The XRD ranges of peaks identified in prominence plot are presented in Table 8. ICP-MS elemental analysis is presented in Table 11.

Example 7: Synthesis of Catalyst 1.7

A solution of (NH$_4$)$_6$Mo$_7$O$_{24}$.4H$_2$O (26.52 g, 21.46 mmol, white crystalline solid) in 100 mL of dH$_2$O was prepared in a 500-mL RBF equipped with magnetic stir bar. A solution of VOSO$_4$.3.36H$_2$O (14.50 g, 64.87 mmol, bright blue crystalline solid) in 90 mL of dH$_2$O was prepared in a 250-mL beaker equipped with magnetic stir bar. Both solutions were stirred in a 60° C. water bath until homogeneous. The blue vanadium solution was then added to the clear colorless molybdenum solution. This resulted in a dark burgundy solution with a fine suspension. The slurry was left to stir at 60° C. for 30 minutes.

The reaction mixture (total volume of about 285 mL measured after rinsing) was transferred to a glass liner. To the mixture was added 278.7 mg of Catalyst 1.6 seeds. The liner was loaded into a 600-mL Parr reactor and the gap filled with $dH_2O$. The reactor was sealed and the head space evacuated and backfilled with $N_2$ gas 10× times. The headspace was left under 15 psig $N_2$ gas and sealed. The reactor was loaded into a programmable oven: ramp 1-hour to 230° C., dwell at 230° C. for 24 hours, cool to 25° C. over 24 hours. Once cooled to room temperature, the reactor was vented, and the contents filtered using a Buchner funnel and 4 qualitative filter papers. The filter cake was rinsed with 800 mL of $dH_2O$. The filtrate was a dark navy-blue color and the product was a mixture of dark purple and light grey color.

The filter cake was dried in the oven at 90° C. overnight with 22.18 g of product being recovered (81% estimated yield). The dry powder product was ground manually with mortar and pestle.

The ground powder was loaded (20.88 g) into a beaker and calcined in a programmable muffle furnace: ramp 30 minutes to 280° C., dwell at 280° C. for 30 minutes, ramp 30 minutes to 400° C., dwell at 400° C. for 6 hours, cool to room temperature without control. There was 20.04 g of catalyst recovered after calcination.

Figure 2:
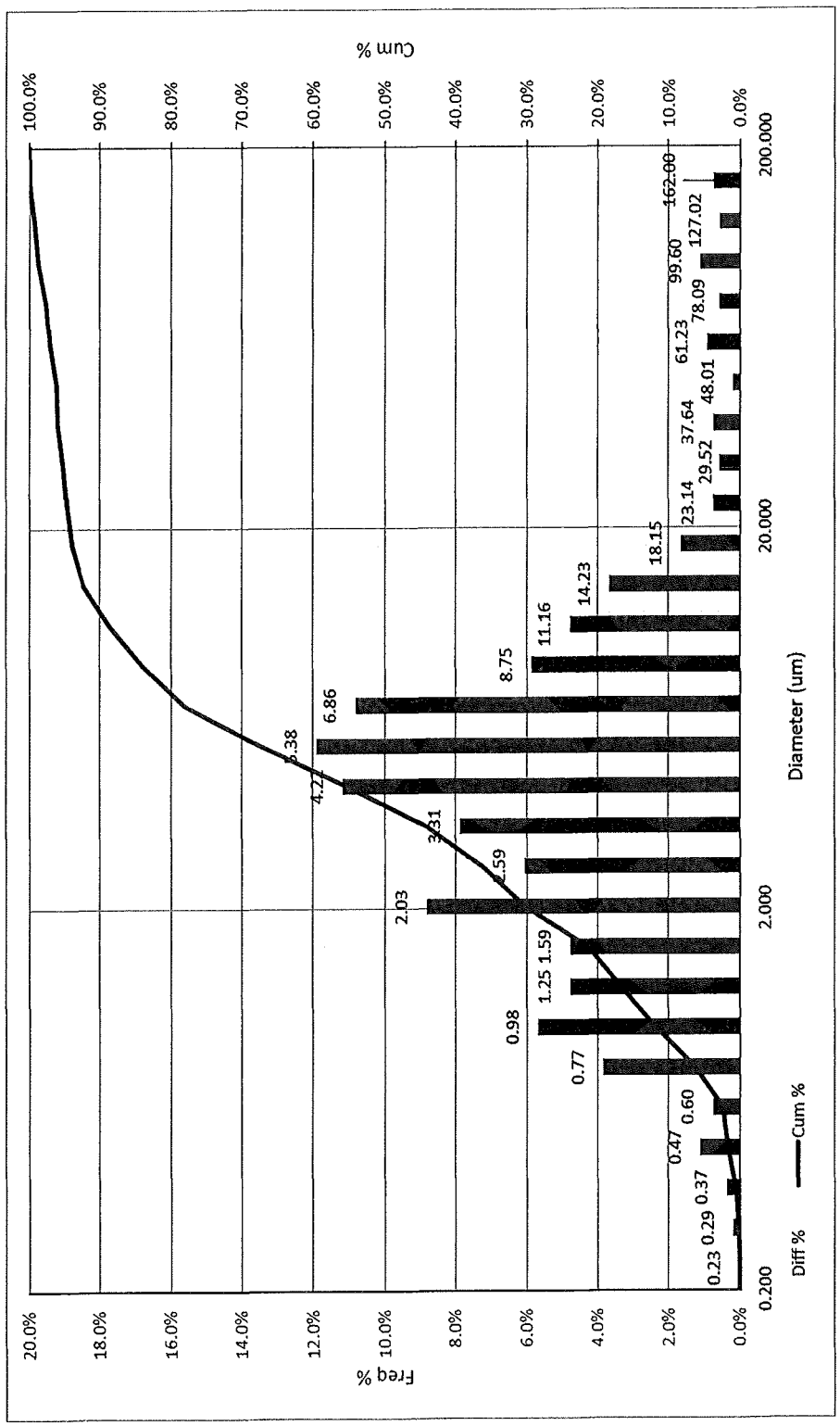
FIG. 2 shows the particle size graph for Catalyst 1.7.

Characterization: The activity for Catalyst 1.7 is presented in Table 1. Particle size distribution statistical data is presented in Table 2. The particle size distribution graph is presented in FIG. 2. SEM-EDS elemental analysis is presented in Table 4. An SEM image at 10,000× magnification is presented in FIG. 7. The bulk density is presented in Table 5. The XRD calculated phases and amorphous phase are presented in Tables 6a and 6b. An XRD diffractogram is presented in FIG. 8. The XRD diffractogram with corresponding peak prominence plot are presented in FIG. 9. The XRD ranges of peaks identified in prominence plot are presented in Table 8. ICP-MS elemental analysis is presented in Table 10.

Example 8: Synthesis of Catalyst 1.8

An oxalic acid solution was prepared by dissolving 3.75 g of oxalic acid dehydrate in 185 mL of distilled water within a 500 mL RBF equipped with magnetic stir bar. To the solution was added 15.01 g of Catalyst 1.8. The solution was allowed to stir in an 80° C. oil bath for 3 hours. Very mild bubbling was observed. The contents of the RBF were filtered using a Buchner funnel and 4 quantitative filter papers. The filter cake was rinsed with 1.1 L of $dH_2O$. The filtrate was an emerald green color and the product was a very fine grey powder.

Since the filtrate was not clear, the filter cake was loaded into a 250 mL bottle and centrifuged at 8000 rpms for 30 minutes. The fine suspension had not settled so the sample was re-centrifuged at 10000 rpms for 30 minutes. The fine suspension had not settled so the sample was re-centrifuged at 9000 rpms for 125 minutes twice. At this point, the top half of the mother liquor (light yellow/lime green color) was removed, and the remainder of the sample was filtered using a Buchner funnel and 4 quantitative filter papers. The filter cake was rinsed with 900 mL of $dH_2O$.

The filter cake was dried in the oven at 90° C. overnight with 9.02 g of catalyst being recovered (60% estimated yield). The dry powder product was very fine grey powder.

Figure 3:
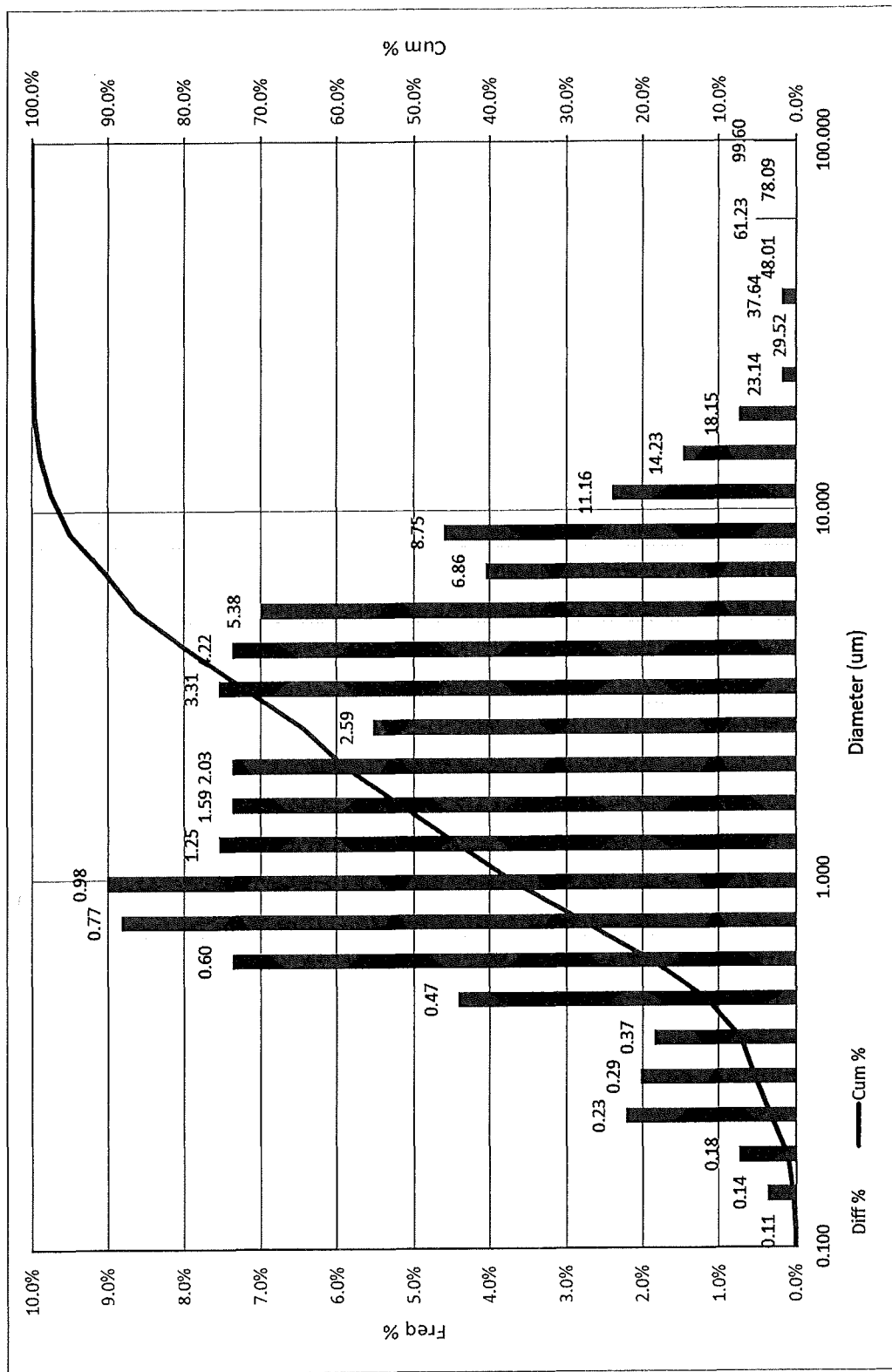
FIG. 3 shows the particle size graph for Catalyst 1.8.

Characterization: The activity for Catalyst 1.8 is presented in Table 1. Particle size distribution statistical data is presented in Table 2. The particle size distribution graph is presented in FIG. 3. SEM-EDS elemental analysis is presented in Table 4. An SEM image at 10,000× magnification is presented in FIG. 7. Bulk density is presented in Table 5. XRD calculated phases and amorphous phase are presented in Tables 7a and 7b. An XRD diffractogram is presented in FIG. 8. The XRD diffractogram with corresponding peak prominence plot is presented in FIG. 10. The XRD ranges of peaks identified in prominence plot are presented in Table 8. ICP-MS elemental analysis is presented in Table 11.

Example 9: Synthesis of Catalyst 1.9

A solution of $(NH_4)_6Mo_7O_{24}.4H_2O$ (26.50 g, 21.44 mmol, white crystalline solid) in 100 mL of $dH_2O$ was prepared in a 500-mL RBF equipped with magnetic stir bar. A solution of $VOSO_4.3.36H_2O$ (14.50 g, 64.87 mmol, bright blue crystalline solid) in 90 mL of $dH_2O$ was prepared in a 250-mL beaker equipped with magnetic stir bar. Both solutions were stirred in a 60° C. water bath until homogeneous. The blue vanadium solution was then added to the clear colorless molybdenum solution. This resulted in a dark burgundy solution with a fine suspension. The slurry was left to stir at 60° C. for 30 minutes.

The reaction mixture (total volume of about 260 mL measured after rinsing) was transferred to a glass liner equipped with magnetic stir bar. To the mixture was added 282.4 mg of Catalyst 1.5 seeds. The liner was loaded into a 600-mL Parr reactor and the gap filled with $dH_2O$. The reactor was sealed and the head space evacuated and backfilled with $N_2$ gas 10× times. The headspace was left under 15 psig $N_2$ gas and sealed. The reactor was connected to a magnetic stir plate. A heating mantel and insulation were used to heat the reaction for 24 hours at 165° C. (heating mantel controller set to 167° C.). Once cooled to room temperature, the reactor was vented, and the contents filtered using a Buchner funnel and 4 qualitative filter papers. The filter cake was rinsed with 800 mL of $dH_2O$. The filtrate was a turquoise/peacock blue color and the product was a dark purple color.

The filter cake was dried in the oven at 90° C. overnight with 28.96 g of product being recovered (100% estimated yield). The dry powder product was ground manually with mortar and pestle.

The ground powder was loaded into a beaker and calcined in a programmable muffle furnace: ramp 30 minutes to 280° C., dwell at 280° C. for 30 minutes, ramp 30 minutes to 400° C., dwell at 400° C. for 6 hours, cool to room temperature without control. There was 26.87 g of catalyst recovered after calcination.

Characterization: The activity for Catalyst 1.9 is presented in Table 1. SEM-EDS elemental analysis is presented in Table 4. An SEM image at 10,000× magnification is presented in FIG. 7. Bulk density is presented in Table 5. The XRD calculated phases and amorphous phase is presented in Tables 6a and 6b. An XRD diffractogram is presented in FIG. 8. The XRD diffractogram with corresponding peak prominence plot presented in FIG. 9. The XRD ranges of peaks identified in prominence plot are presented in Table 8.

Example 10: Synthesis of Catalyst 1.10

An oxalic acid solution was prepared by dissolving 2.50 g of oxalic acid dehydrate in 250 mL of distilled water within a 500 mL RBF equipped with magnetic stir bar. To the solution was added 10.00 g of Catalyst 1.9. The solution was allowed to stir in an 80° C. oil bath for 3 hours. Very mild bubbling was observed. The contents of the RBF were filtered using a Buchner funnel and 4 quantitative filter papers. The filter cake was rinsed with 500 mL of $dH_2O$. The filtrate was an emerald green color and the product was a very fine grey powder.

The filter cake was dried in the oven at 90° C. overnight with 5.72 g of catalyst being recovered (57% yield). The dry powder product was very fine grey powder.

Characterization: The activity for Catalyst 1.10 is presented in Table 1. SEM-EDS elemental analysis is presented in Table 4. An SEM image at 10,000× magnification is presented in FIG. 7. Bulk density is presented in Table 5. XRD calculated phases and amorphous phase are presented in Tables 7a and 7b. An XRD diffractogram is presented in FIG. 8. The XRD diffractogram with corresponding peak prominence plot is presented in FIG. 10. The XRD ranges of peaks identified in prominence plot are presented in Table 8.

Example 11: Synthesis of Catalyst 1.11

A solution of $(NH_4)_6Mo_7O_{24} \cdot 4H_2O$ (88.40 g, 71.56 mmol, white crystalline solid) in 330 mL of $dH_2O$ was prepared in a 2-L RBF equipped with magnetic stir bar. A solution of $VOSO_4 \cdot 3.36H_2O$ (48.00 g, 214.74 mmol, bright blue crystalline solid) in 300 mL of $dH_2O$ was prepared in a 500-mL beaker equipped with magnetic stir bar. Both solutions were stirred in a 60° C. water bath until homogeneous. The blue vanadium solution was then added to the clear colorless molybdenum solution. This resulted in a dark burgundy solution with a fine suspension. The slurry was left to stir at 60° C. for 30 minutes.

The reaction mixture (total volume of about 735 mL measured after rinsing) was transferred to a glass liner. To the mixture was added 327.1 mg of Catalyst 1.5 seeds. The liner was loaded into a 2-L Parr reactor and the gap filled with $dH_2O$. The reactor was sealed and the head space evacuated and backfilled with $N_2$ gas 10× times. The headspace was left under 15 psig $N_2$ gas and sealed. The reactor was connected to an overhead stirrer. A heating mantel and insulation were used to heat the reaction for 24 hours at 220° C. (heating mantel controller set to 245° C.). Once cooled to room temperature, the reactor was vented, and the contents filtered using a Buchner funnel and 4 qualitative filter papers. The filter cake was rinsed with 1.8 L of $dH_2O$. The filtrate was a dilute navy-blue color and the product was a dark purple/grey color.

The filter cake was dried in the oven at 90° C. overnight with 90.64 g of product being recovered (99% estimated yield). The dry powder product was ground manually with mortar and pestle.

The ground powder was loaded (39.53) into a beaker and calcined in a programmable muffle furnace: ramp 30 minutes to 280° C., dwell at 280° C. for 30 minutes, ramp 30 minutes to 400° C., dwell at 400° C. for 6 hours, cool to room temperature without control. There was 37.53 g of catalyst, grey color with olive green tint, recovered after calcination.

Figure 4:
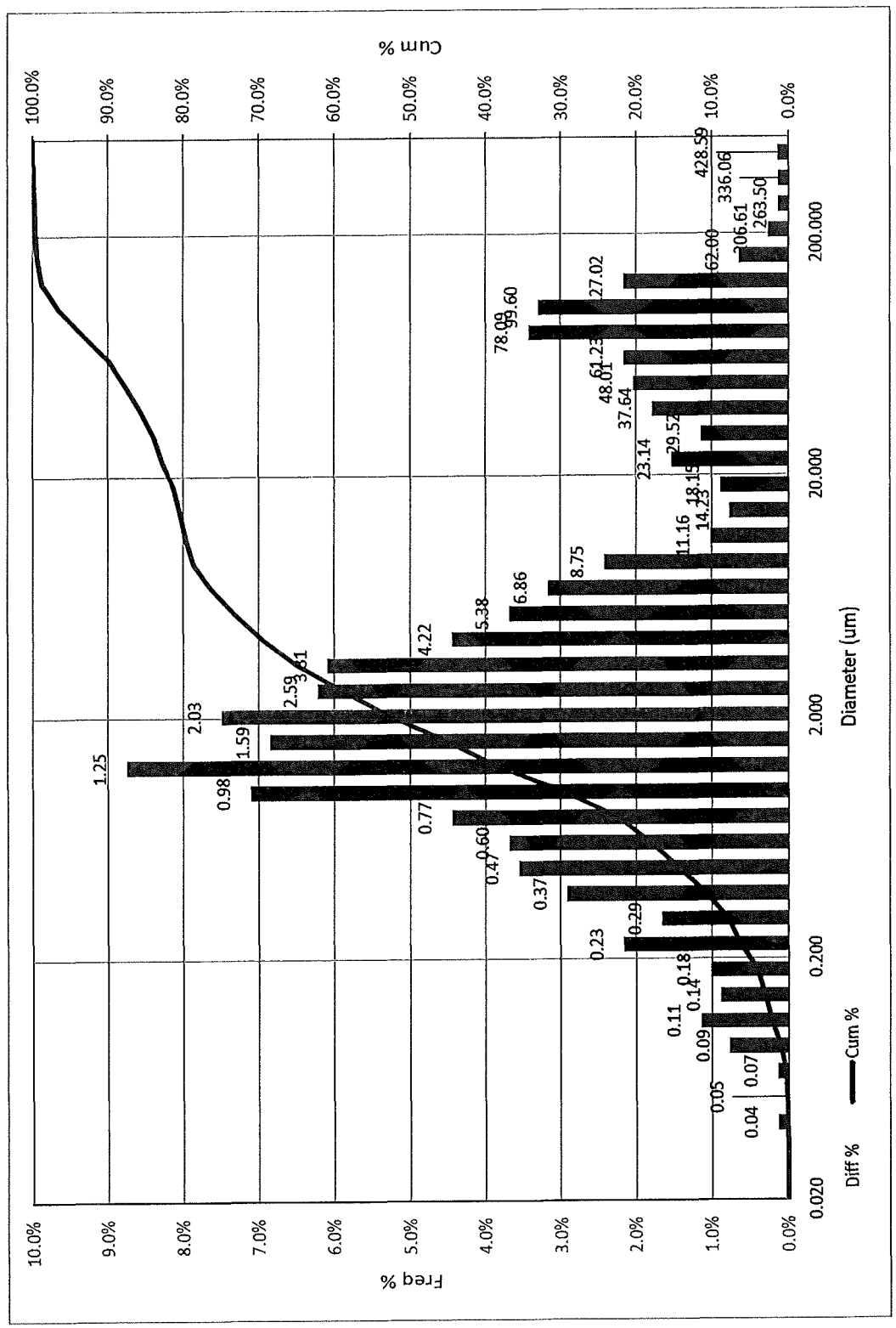
FIG. 4 shows the particle size graph for Catalyst 1.11.

Characterization: The activity for Catalyst 1.11 is presented in Table 1. Particle size distribution statistical data is presented in Table 2. The particle size distribution graph is presented in FIG. 4. BET surface area and pore volume data presented in Table 3. BJH Pore size distribution curve presented in FIG. 6. SEM-EDS elemental analysis is presented in Table 4. An SEM image at 10,000× magnification is presented in FIG. 7. Bulk density is presented in Table 5. The XRD calculated phases and amorphous phase is presented in Tables 6a and 6b. An XRD diffractogram is presented in FIG. 8. The XRD diffractogram with corresponding peak prominence plot presented in FIG. 9. The XRD ranges of peaks identified in prominence plot are presented in Table 8. ICP-MS elemental analysis is presented in Table 10.

Example 12: Synthesis of Catalyst 1.12

An oxalic acid solution was prepared by dissolving 3.75 g of oxalic acid dehydrate in 100 mL of distilled water within a 500 mL RBF equipped with magnetic stir bar. To the solution was added 10.00 g of Catalyst 1.11. The solution was allowed to stir in an 80° C. oil bath for 3 hours. Very mild bubbling was observed. The contents of the RBF were filtered using a Buchner funnel and 4 quantitative filter papers. The filter cake was rinsed with 1.2 L of $dH_2O$. The filtrate was an emerald green color and the product was a very fine grey powder.

The filter cake was dried in the oven at 90° C. overnight with 4.31 g of catalyst being recovered (43% yield). The dry powder product was very fine grey powder.

Figure 5:
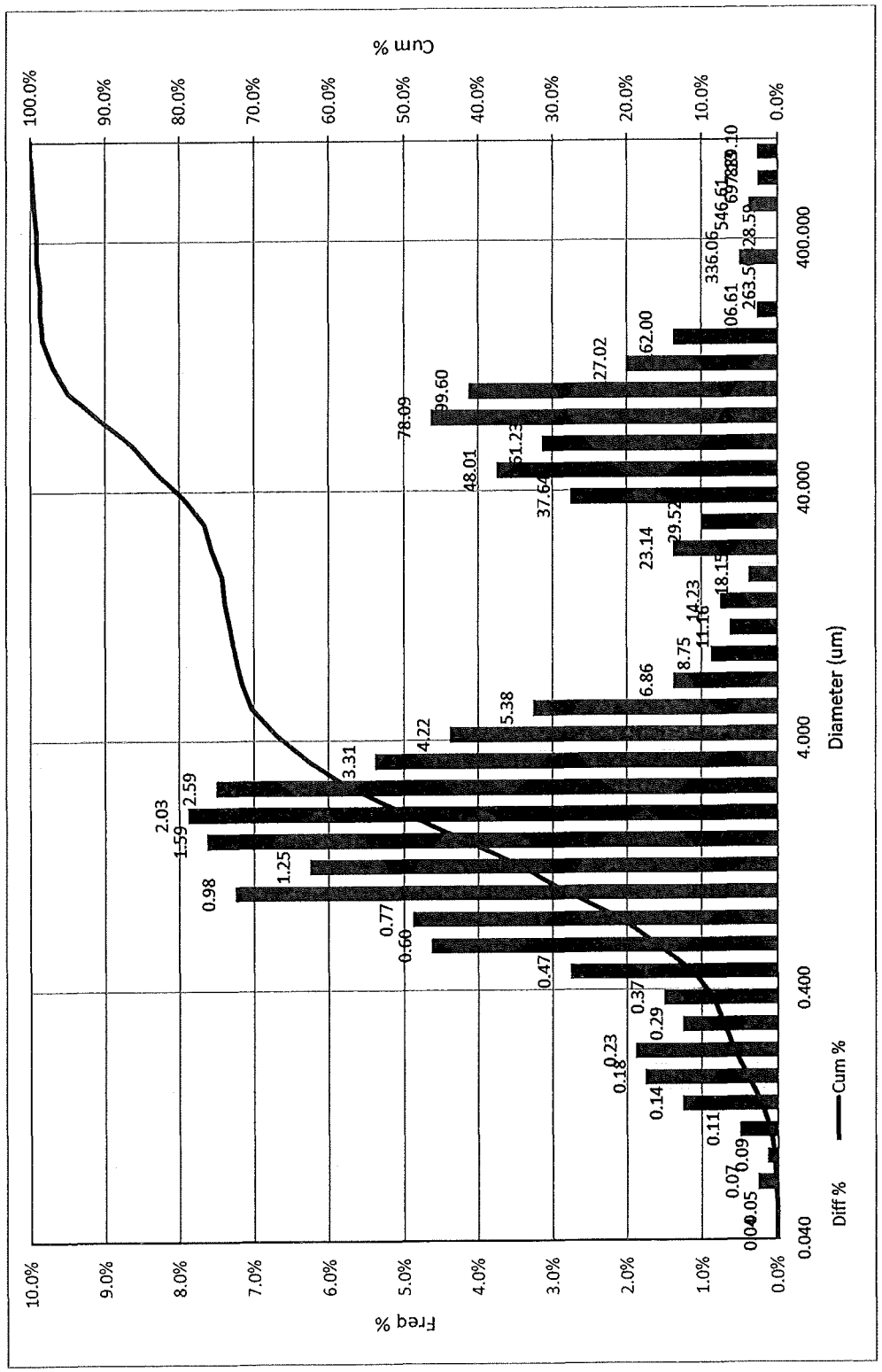
FIG. 5 shows the particle size graph for Catalyst 1.12.

Characterization: The activity for Catalyst 1.12 is presented in Table 1. Particle size distribution statistical data is presented in Table 2. The particle size distribution graph is presented in FIG. 5. BET surface area and pore volume data presented in Table 3. BJH Pore size distribution curve presented in FIG. 6. SEM-EDS elemental analysis is presented in Table 4. An SEM image at 10,000× magnification is presented in FIG. 7. Bulk density is presented in Table 5. XRD calculated phases and amorphous phase are presented in Tables 7a and 7b. An XRD diffractogram is presented in FIG. 8. The XRD diffractogram with corresponding peak prominence plot is presented in FIG. 10. The XRD ranges of peaks identified in prominence plot are presented in Table 8. ICP-MS elemental analysis is presented in Table 11.

Example 13: Synthesis of Catalyst 1.13

An oxalic acid solution was prepared by dissolving 5.64 g of oxalic acid dehydrate in 152 mL of distilled water within a 500-mL RBF equipped with magnetic stir bar. To the solution was added 15.03 g of calcined Catalyst 1.11. The solution was allowed to stir in an 80° C. oil bath for 3 hours. Very mild bubbling was observed. The contents of the RBF were filtered using a Buchner funnel and 4 quantitative filter papers. The filter cake was rinsed with 900 mL of $dH_2O$. The filtrate was an emerald green color and the product was a very fine grey powder.

The filter cake was dried in the oven at 90° C. overnight with 6.50 g of catalyst being recovered (43% yield). The dry powder product was very fine grey powder.

Characterization: The activity for Catalyst 1.13 is presented in Table 1. SEM-EDS elemental analysis is presented in Table 4. The XRD calculated phases and amorphous phase is presented in Table 7a. An XRD diffractogram is presented in FIG. 8. The XRD diffractogram with corresponding peak prominence plot is presented in FIG. 10. The XRD ranges of peaks identified in prominence plot are presented in Table 8. ICP-MS elemental analysis is presented in Table 11.

Example 14: Synthesis of Catalyst 1.14

A solution of $(NH_4)_6Mo_7O_{24} \cdot 4H_2O$ (88.40 g, 71.53 mmol, white crystalline solid) in 330 mL of $dH_2O$ was prepared in a 2-L RBF equipped with magnetic stir bar. A solution of $VOSO_4.3.36H_2O$ (48.00 g, 214.74 mmol, bright blue crystalline solid) in 300 mL of $dH_2O$ was prepared in a 500-mL beaker equipped with magnetic stir bar. Both solutions were stirred in a 60° C. water bath until homogeneous. The blue vanadium solution was then added to the clear colorless molybdenum solution. This resulted in a dark burgundy solution with a fine suspension. The slurry was left to stir at 60° C. for 30 minutes.

The reaction mixture (total volume of about 830 mL measured after rinsing) was transferred to a glass liner. To the mixture was added 510.8 mg of Catalyst Seeds 2.1. The liner was loaded into a 2-L Parr reactor and the gap filled with $dH_2O$. The reactor was sealed and the head space evacuated and backfilled with $N_2$ gas 10 times. The headspace was left under 15 psig $N_2$ gas and sealed. The reactor was connected to an overhead stirrer. A heating mantel and insulation were used to heat the reaction for 24 hours at 231° C. (heating mantel controller set to 242° C.). Once cooled to room temperature, the reactor was vented, and the contents filtered using a Buchner funnel and 4 qualitative filter papers. The filter cake was rinsed with 1.2 L of $dH_2O$. The filtrate was a dilute navy-blue color and the product was a dark purple/grey color.

The filter cake was dried in the oven at 90° C. overnight with 88.81 g of product being recovered (97% estimated yield). The dry powder product was ground manually with mortar and pestle.

The ground powder was loaded (38.44 g) into a beaker and calcined in a programmable muffle furnace: ramp 30 minutes to 280° C., dwell at 280° C. for 30 minutes, ramp 30 minutes to 400° C., dwell at 400° C. for 6 hours, cool to room temperature without control. There was 36.09 g of catalyst, grey color with olive green tint, recovered after calcination.

Characterization: The activity for Catalyst 1.14 is presented in Table 1. BET surface area and pore volume data presented in Table 3. BJH Pore size distribution curve presented in FIG. 6. SEM-EDS elemental analysis is presented in Table 4. Bulk density is presented in Table 5. The XRD calculated phases and amorphous phase is presented in Tables 6a and 6b. An XRD diffractogram is presented in FIG. 8. The XRD diffractogram with corresponding peak prominence plot presented in FIG. 9. The XRD ranges of peaks identified in prominence plot are presented in Table 8. ICP-MS elemental analysis is presented in Table 10.

Example 15: Synthesis of Catalyst 1.15

An oxalic acid solution was prepared by dissolving 3.75 g of oxalic acid dehydrate in 100 mL of distilled water within a 500-mL RBF equipped with magnetic stir bar. To the solution was added 10.01 g of calcined Catalyst 1.14. The solution was allowed to stir in an 80° C. oil bath for 3 hours. Very mild bubbling was observed. The contents of the RBF were filtered using a Buchner funnel and 4 quantitative filter papers. The filter cake was rinsed with 500 mL of $dH_2O$. The filtrate was an emerald green color and the product was a very fine grey powder.

The filter cake was dried in the oven at 90° C. overnight with 4.22 g of catalyst being recovered (42% yield). The dry powder product was very fine grey powder.

Characterization: The activity for Catalyst 1.15 is presented in Table 1. BET surface area and pore volume data presented in Table 3. BJH Pore size distribution curve presented in FIG. 6. SEM-EDS elemental analysis is presented in Table 4. XRD calculated phases and amorphous phase are presented in Tables 7a and 7b. An XRD diffractogram is presented in FIG. 8. The XRD diffractogram with corresponding peak prominence plot is presented in FIG. 10. The XRD ranges of peaks identified in prominence plot are presented in Table 8. ICP-MS elemental analysis is presented in Table 11.

Example 16: Synthesis of Precalcined Catalyst 1.16

A solution of $(NH_4)_6Mo_7O_{24}.4H_2O$ (88.40 g, 71.53 mmol, white crystalline solid) in 330 mL of $dH_2O$ was prepared in a 2-L RBF equipped with magnetic stir bar. A solution of $VOSO_4.3.36H_2O$ (48.00 g, 214.74 mmol, bright blue crystalline solid) in 300 mL of $dH_2O$ was prepared in a 500-mL beaker equipped with magnetic stir bar. Both solutions were stirred in a 60° C. water bath until homogeneous. The blue vanadium solution was then added to the clear colorless molybdenum solution. This resulted in a dark burgundy solution with a fine suspension. The slurry was left to stir at 60° C. for 30 minutes.

The reaction mixture (total volume of about 840 mL measured after rinsing) was transferred to a glass liner. To the mixture was added 1.00 g of Catalyst 2.1 Seeds. The liner was loaded into a 2-L Parr reactor and the gap filled with $dH_2O$. The reactor was sealed and the head space evacuated and backfilled with $N_2$ gas 10 times. The headspace was left under 15 psig $N_2$ gas and sealed. The reactor was connected to an overhead stirrer. A heating mantel and insulation were used to heat the reaction for 24 hours at 232° C. (heating mantel controller set to 240° C.). Once cooled to room temperature, the reactor was vented, and the contents filtered using a Buchner funnel and 4 qualitative filter papers. The filter cake was rinsed with 850 mL of $dH_2O$. The filtrate was a dilute navy-blue color and the product was a dark purple/grey color.

The filter cake was dried in the oven at 90° C. overnight with 87.19 g of product being recovered (95% estimated yield). The dry powder product was ground manually with mortar and pestle.

Example 17: Synthesis of Precalcined Catalyst 1.17

An oxalic acid solution was prepared by dissolving 16.20 g of oxalic acid dehydrate in 450 mL of distilled water within a 1-L RBF equipped with magnetic stir bar. To the solution was added 43.25 g of Precalcined Catalyst 1.16. The solution was allowed to stir in an 80° C. oil bath for 3 hours. Very mild bubbling was observed. The contents of the RBF were filtered using a Buchner funnel and 4 quantitative filter papers. The filter cake was rinsed with 1200 mL of $dH_2O$. The filtrate was a blue/green turquoise color and the product was a very fine purple powder.

The filter cake was dried in the oven at 90° C. overnight with 22.60 g of catalyst being recovered (52% yield). The dry powder product was very fine grey powder.

Example 18: Synthesis of Catalyst 1.18

Precalcined Catalyst 1.17 was loaded (10.06 g) into a beaker and calcined in a programmable muffle furnace: ramp 30 minutes to 280° C., dwell at 280° C. for 30 minutes, ramp 30 minutes to 400° C., dwell at 400° C. for 6 hours, cool to room temperature without control. There was 9.58 g of catalyst, grey color with olive green tint, recovered after calcination.

Characterization: The activity for Catalyst 1.18 is presented in Table 1. SEM-EDS elemental analysis is presented in Table 4. An SEM image at 10,000× magnification is presented in FIG. 7. The XRD calculated phases and amorphous phase is presented in Table 7a. An XRD diffractogram is presented in FIG. 8. The XRD diffractogram with corresponding peak prominence plot is presented in FIG. 10. The XRD ranges of peaks identified in prominence plot are presented in Table 8.

Example 19: Synthesis of Catalyst 1.19

The powder from Precalcined Catalyst 1.17 was loaded (10.00 g) into a quartz boat and placed in a quartz tube. The quartz tube was loaded into a split tube furnace. The quartz tube was then purged with purified nitrogen at approximately 85 sccm (0.085 standard liter per minute (slpm)) for 18 hours. The flow of nitrogen was then reduced to approximately 30 sccm and the material was calcined in the programmable split tube furnace: ramp 4 hours to 400° C., dwell at 400° C. for 2 hours, cool to room temperature without control. There was 9.15 g of catalyst, dark purple, almost black, recovered after calcination.

Characterization: The activity for Catalyst 1.19 is presented in Table 1. SEM-EDS elemental analysis is presented in Table 4. An SEM image at 10,000× magnification is presented in FIG. 7. The XRD calculated phases and amorphous phase is presented in Table 7a. An XRD diffractogram is presented in FIG. 8. The XRD diffractogram with corresponding peak prominence plot is presented in FIG. 10. The XRD ranges of peaks identified in prominence plot are presented in Table 8.

Example 20: Synthesis of Catalyst 1.20

The powder from Precalcined Catalyst 1.16 was loaded (20.82 g) into a beaker and calcined in a programmable muffle furnace: ramp 30 minutes to 280° C., dwell at 280° C. for 30 minutes, ramp 30 minutes to 400° C., dwell at 400° C. for 6 hours, cool to room temperature without control. There was 19.60 g of catalyst, grey color with olive green tint, recovered after calcination.

Characterization: The activity for Catalyst 1.20 is presented in Table 1. SEM-EDS elemental analysis is presented in Table 4. An SEM image at 10,000× magnification is presented in FIG. 7. The XRD calculated phases and amorphous phase is presented in Table 6a. An XRD diffractogram is presented in FIG. 8. The XRD diffractogram with corresponding peak prominence plot presented in FIG. 9. The XRD ranges of peaks identified in prominence plot are presented in Table 8.

Example 21: Synthesis of Catalyst 1.21

The powder from Precalcined Catalyst 1.16 was loaded (21.5 g) into a quartz boat and placed in a quartz tube. The quartz tube was loaded into a large split tube furnace. The quartz tube was purged with bulk nitrogen for 3 hours, and then purified nitrogen at approximately 400 sccm (0.085 standard liter per minute (slpm)) for 18 hours. The material was calcined in the programmable split tube furnace: ramp 4 hours to 400° C., dwell at 400° C. for 2 hours, cool to room temperature without control. There was 19.7 g of catalyst, dark purple, almost black, recovered after calcination.

Characterization: The activity for Catalyst 1.21 is presented in Table 1. SEM-EDS elemental analysis is presented in Table 4. An SEM image at 10,000× magnification is presented in FIG. 7. The XRD calculated phases and amorphous phase is presented in Table 6a. An XRD diffractogram is presented in FIG. 8. The XRD diffractogram with corresponding peak prominence plot presented in FIG. 9. The XRD ranges of peaks identified in prominence plot are presented in Table 8.

Example 22: Synthesis of Catalyst Seeds 2.1

A solution of oxalic acid (1102 g, 12.2 mol, white solid) in 10 L of $dH_2O$ was prepared in a large vessel equipped with an overhead stirrer. The solution was stirred at 65° C. until homogeneous (clear and colorless). To the solution was added $Nb_2O_5.xH_2O$ (656.3 g, 2.0 mmol, assumed from 80% weight $Nb_2O_5$ with MW of 265.81 g/mol, white crystalline solid), which formed a white suspension. An additional 1 L of $dH_2O$ was used to rinse off the edges of the vessel, and the mixture was allowed to stir at 65° C. for 24-72 hours, obtaining a clear colorless solution. Once homogeneous, the solution was allowed to cool to room temperature.

A solution of $Te(OH)_6$ (10.54.6 g, 4.6 mol, white crystalline solid) in 6 L of $dH_2O$ was prepared in a large vessel equipped with an overhead stirrer. An additional 1 L of $dH_2O$ was used to rinse off the edges of the vessel. The solution was stirred at 60° C. until homogeneous (clear and colorless). Once homogeneous, the solution was allowed to cool to room temperature.

A solution of $(NH_4)_6Mo_7O_{24}.4H_2O$ (4865 g, 3.9 mol, white crystalline solid) in 16 L of $dH_2O$ was prepared in a jacketed glass reactor. The solution was heated 30-35° C. via circulating bath and silicone oil. An additional 1 L of $dH_2O$ was used to rinse off the edges of the vessel. After stirring, the resulting mixture formed a white, some-what turbid solution. The 7 L of $TeOH_{6(aq)}$ solution was transferred at ambient temperature to the stirred, 30-35° C. $(NH_4)_6Mo_7O_{24}.4H_2O_{(aq)}$ turbid solution at a rate of 412 mL/min to form a clear and colorless solution (herein referred to as "MoTe solution"). The telluric acid vessel was rinsed with 1 L of $dH_2O$ and the rinsing was transferred to the glass reactor. The resulting MoTe solution was heated to 80° C. Once the MoTe solution had reached 80° C., the pH of the MoTe solution was adjusted to 7.50±0.1 using 1680-2000 grams (calculated 1.85-2.20 L at density of 0.91 g/cm³) of 28-30% ammonium hydroxide solution. The MoTe solution was stirred at 80° C. for 1 hour, after which the pH was adjusted from 7.50 to 5.00±0.1 using 1270-1550 grams (calculated 0.69-0.84 L at density of 1.85 g/cm³) of 95-98% sulfuric acid. The resulting aqueous ammonium molybdotellurate, $(NH_4)_6Mo_6TeO_{24(aq)}$, solution was transferred to a pre-heated 60° C. hydrothermal treatment reactor. The glass reactor vessel was rinsed with 2 L of $dH_2O$ and the rinsing was transferred to the pre-heated (60° C.) hydrothermal reactor. The solution was stirred via an agitator inside the high-pressure reactor at 60° C.

A solution of $VOSO_4.3.41H_2O$ (4043 g, 18.1 mol, bright blue crystalline solid) in 11 L of $dH_2O$ was prepared in a large vessel equipped with an overhead stirrer. The vessel was rinsed with 1 L of $dH_2O$. The solution was stirred vigorously at 60° C. until homogeneous (clear and bright blue). Once homogeneous, this $VOSO_{4(aq)}$ solution was transferred to the MoTe solution in the high-pressure reactor at a rate of 367 mL/min. The large vessel was rinsed with 2 L of $dH_2O$ and the rinsing was transferred to the glass reactor. The resulting black solution was stirred for 30 minutes at 60° C.

The slurry inside the high-pressure reactor was heated to 160-165° C. over approximately 5 hours using a heating mantel, and the pressure maintained at 95-105 psig using a back-pressure regulator connected to a condenser. The reaction was stirred slowly, preventing the slurry from settling at these conditions for 24-48 hours. Note, if the skin temperature of the reactor exceeded 185° C., the quality of the catalyst would suffer. The reactor was then cooled back down to roughly 30° C. and then filtered. The product was washed with 200 L of dH$_2$O in 40 L increments. The product was then dried in an oven at 90° C. for 3-5 days. Once dry, CHNS analysis was performed to ensure that the following specifications are met: N=0.90 to 1.75% and S<0.02%. The product was then ground to particle sizes in the 125-500 μm range.

Catalyst samples were loaded into 3 quartz boats, each capable of holding 1000 g portions. These boats were loaded into the quartz tube of the Catalyst Calcining Furnace (CCF), such that the boats sat in the middle of the heating zone. Ceramic boats were loaded horizontally into the quartz tube at the inlet of the tube. These were intended to act as an obstruction to the nitrogen flow, pushing the nitrogen to the walls of the tube and promoting it to heat up. The tube was sealed, and bulk nitrogen was allowed to flow at 207-948.22 cc/min sccm for 8 hours. After 8 hours of purging, the feed gas was switched to purified nitrogen (purified by a catalyst bed vessel). The tube was purged with purified nitrogen for 12 hours. The tube was heated from room temperature to 600° C. at a rate of 1.61° C./minute over the span of 6 hours. The temperature was held at 600° C. for 6 hours and then the tube allowed to cool back to ambient temperature through natural heat dissipation.

Microreactor Unit Results

The 35% conversion temperature (° C.) and selectivity to ethylene for Catalysts 1.1-1.3, 1.6-1.15, and 1.21 are presented in Table 1.

TABLE 1

| Catalyst | 35% Conversion Temperature (° C.) | Selectivity to Ethylene |
| --- | --- | --- |
| Catalyst 1.1 | 310 | 86% |
| Catalyst 1.2 | 376 | 77% |
| Catalyst 1.3 | 395 | 67% |
| Catalyst 1.6 | 327 | 85% |
| Catalyst 1.7 | 390 | 80% |
| Catalyst 1.8 | 351 | 81% |
| Catalyst 1.9 | 372 | 79% |
| Catalyst 1.10 | 369 | 84% |
| Catalyst 1.11 | 424 | 70% |
| Catalyst 1.12 | 350 | 83% |
| Catalyst 1.13 | 339 | 83% |
| Catalyst 1.14 | 408 | 71% |
| Catalyst 1.15 | 353 | 81% |
| Catalyst 1.18 | 352 | 80% |
| Catalyst 1.19 | 391 | 63% |
| Catalyst 1.20 | 376 | 76% |
| Catalyst 1.21 | 422 | 56% |

Particle Size Distribution

The particle size distribution statistical data in μm for catalyst 1.2, 1.7, 1.8, 1.11, and 1.12 is presented in Table 2.

TABLE 2

|  | Catalyst 1.2 | Catalyst 1.7 | Catalyst 1.8 | Catalyst 1.11 | Catalyst 1.12 |
| --- | --- | --- | --- | --- | --- |
| Maximum | 11.19 | 154.20 | 33.62 | 367.60 | 888.20 |
| Minimum | 0.11 | 0.27 | 0.12 | 0.04 | 0.06 |
| Mean | 1.79 | 8.19 | 2.73 | 15.22 | 24.93 |
| Median | 1.32 | 3.75 | 1.52 | 1.87 | 2.04 |
| Mode | 0.98-1.25 | 4.22-5.38 | 0.77-0.98 | 0.98-1.25 | 1.59-2.03 |
| Range | 11.08 | 153.93 | 33.50 | 367.56 | 888.14 |
| Skewness | 2.05 | 5.25 | 3.21 | 4.03 | 7.37 |
| Kurtosis | 5.53 | 30.22 | 18.28 | 24.94 | 69.78 |
| Standard Deviation | 1.55 | 18.56 | 3.24 | 33.98 | 71.37 |
| D10 | 0.44 | 0.92 | 0.43 | 0.35 | — |
| D25 (Quartile 1) | 0.73 | 1.76 | 0.71 | 0.86 | 0.89 |
| D50 | 1.32 | 3.75 | 1.52 | 1.87 | — |
| D75 (Quartile 3) | 2.29 | 6.53 | 3.56 | 6.28 | 20.77 |
| D90 | 3.73 | 11.89 | 6.67 | 61.82 | — |

BET and BJH Analysis

The BET surface area and pore volume for Catalyst 1.1-1.3, 1.11, 1.12, uncalcined Catalyst 1.14, Catalyst 1.14, and Catalyst 1.15 are presented in Table 3.

TABLE 3

| Catalyst | BET Surface Area (m$^2$/g) | Pore Volume (cm$^3$/g) |
| --- | --- | --- |
| Catalyst 1.1 | 3 | 0.02 |
| Catalyst 1.2 | 8 | 0.02 |
| Catalyst 1.3 | 4 | 0.01 |
| Catalyst 1.14 - uncalcined | 24 | 0.07 |
| Catalyst 1.11 | 15 | 0.07 |
| Catalyst 1.14 | 16 | 0.09 |
| Catalyst 1.12 | 27 | 0.11 |
| Catalyst 1.15 | 18 | 0.08 |

SEM-EDS Elemental Analysis

The SEM-EDS elemental analysis results for Catalysts 1.1-1.3, 1.5-1.15, and 1.18-1.21 are presented in Table 4.

TABLE 4

| Sample | Elemental Mass % | | Catalyst Material Formula |
| --- | --- | --- | --- |
|  | Mo | V |  |
| Catalyst 1.1 | 51.97 | 12.29 | Mo$_1$V$_{0.45}$ |
| Catalyst 1.2 | 46.66 | 14.61 | Mo$_1$V$_{0.59}$ |
| Catalyst 1.3 | 49.95 | 15.35 | Mo$_1$V$_{0.58}$ |
| Catalyst 1.21 | 53.94 | 12.93 | Mo$_1$V$_{0.45}$ |
| Catalyst 1.7 | 50.23 | 14.07 | Mo$_1$V$_{0.53}$ |
| Catalyst 1.9 | 53.85 | 12.03 | Mo$_1$V$_{0.42}$ |
| Catalyst 1.11 | 53.15 | 11.42 | Mo$_1$V$_{0.40}$ |
| Catalyst 1.14 | 52.05 | 12.36 | Mo$_1$V$_{0.45}$ |
| Catalyst 1.20 | 53.29 | 12.2 | Mo$_1$V$_{0.43}$ |
| Catalyst 1.5 | 50.68 | 10.14 | Mo$_1$V$_{0.38}$ |
| Catalyst 1.6 | 51.88 | 10.67 | Mo$_1$V$_{0.39}$ |
| Catalyst 1.8 | 52.63 | 11.00 | Mo$_1$V$_{0.39}$ |
| Catalyst 1.10 | 54.94 | 9.92 | Mo$_1$V$_{0.34}$ |
| Catalyst 1.12 | 54.45 | 8.43 | Mo$_1$V$_{0.29}$ |
| Catalyst 1.13 | 55.13 | 8.49 | Mo$_1$V$_{0.29}$ |
| Catalyst 1.15 | 52.45 | 8.91 | Mo$_1$V$_{0.32}$ |
| Catalyst 1.18 | 52.39 | 11.44 | Mo$_1$V$_{0.41}$ |
| Catalyst 1.19 | 54.62 | 11.79 | Mo$_1$V$_{0.41}$ |

Bulk Density

The bulk densities for Catalyst 1.7-1.12 and 1.14 are presented in Table 5.

TABLE 5

| Sample | Bulk Density (g/cm$^3$) | | | |
|---|---|---|---|---|
| | 1$^{st}$ Measurement | 2$^{nd}$ Measurement | Average | Standard deviation |
| Catalyst 1.7 | 0.5266 | 0.5292 | 0.5279 | 0.002 |
| Catalyst 1.8 | 1.4688 | 1.4676 | 1.4682 | 0.0008 |
| Catalyst 1.9 | 1.3512 | 1.3111 | 1.3312 | 0.03 |
| Catalyst 1.10 | 1.2505 | 0.8554 | 1.0530 | 0.3 |
| Catalyst 1.11 | 0.9491 | 1.1174 | 1.0333 | 0.1 |
| Catalyst 1.12 | 1.0386 | 1.0296 | 1.0341 | 0.006 |
| Catalyst 1.14 | 0.5786 | 0.5295 | 0.5541 | 0.03 |

XRD Calculated Phases and Amorphous Phases

Calculated phases as per Rietveld Refinement (Method A), MoVOx phase (isostructural to M1* phase) determination, and amorphous content for Catalysts 1.1-1.3, 1.7, 1.9, 1.14, 1.20, and 1.21 are presented in Table 6a. Calculated phases as per Rietveld Refinement (Method B), M1* phase determination, and amorphous content for Catalysts 1.1-1.3, 1.7, 1.9, 1.11, and 1.14 are presented in Table 6b. Calculated phases as per Rietveld Refinement (Method A), MoVO$_x$ phase (isostructural to M1* phase) determination, and amorphous content for Catalysts 1.5, 1.6, 1.8, 1.10, 1.12, 1.13, 1.15, 1.18, and 1.19 are presented in Table 7a. Calculated phases as per Rietveld Refinement (Method B), M1* phase determination, and amorphous content for Catalysts 1.5, 1.6, 1.8, 1.10, 1.12, 1.13, and 1.15 are presented in Table 7b.

TABLE 6a

| Ref. Code | Chemical formula | Compound name | Mineral name | Catalyst (Cat.) 1.1 | Cat. 1.2 | Cat. 1.3 | Cat. 1.21 | Cat. 1.7 | Cat. 1.9 | Cat. 1.11 | Cat. 1.14 | Cat. 1.20 |
|---|---|---|---|---|---|---|---|---|---|---|---|---|
| 04-022-1665 | $V_{5.5}Mo_{14.5}O_{54.65}$ | Vanadium Molybdenum Oxide | — | 34.1 | 3.9 | 7.0 | 2.5 | 9.6 | 6.4 | 4.3 | 2.9 | 4.9 |
| 04-022-1664 | $V_{5.5}Mo_{14.5}O_{52.6}$ | Vanadium Molybdenum Oxide | — | 13.7 | — | 2.8 | 3.6 | 1.5 | 1.4 | — | 0.2 | 1.5 |
| 04-010-3742 | $V_6Mo_{12}(VO_4)O_{42}(OH)_9(H_2O)_{11}$ | Vanadium Molybdenum Vanadium Oxide Hydroxide Hydrate | — | — | 2.3 | 4.2 | — | 1.7 | 3.6 | 2.4 | 1.2 | 1.3 |
| 04-015-1304 | $V_{5.5}Mo_{6.6}O_{24.2}$ | Vanadium Molybdenum Oxide | — | — | — | — | — | 0.1 | — | — | — | — |
| 04-015-1304 | $V_{2.2}Mo_{6.6}O_{24.2}$ | Vanadium Molybdenum Oxide | — | — | — | — | — | — | — | — | — | 0.7 |
| 04-011-5829 | $V_{1.80}Mo_{0.20}O_3$ | Vanadium Molybdenum Oxide | — | 0.3 | — | — | — | — | — | — | — | — |
| 04-011-9636 | $V_{1.48}Mo_{1.52}O_8$ | Vanadium Molybdenum Oxide | — | — | — | — | — | — | — | 11.9 | 13.0 | 14.4 |
| 04-013-6424 | $V_{1.1}Mo_{0.9}O_5$ | Vanadium Molybdenum Oxide | — | — | 29.6 | 15.9 | 5.9 | 2.3 | — | — | — | — |
| 04-015-6540 01-077-0649 | $V_{0.95}Mo_{0.97}O_5$ | Vanadium Molybdenum Oxide | — | — | — | — | — | 38.8 | 13.7 | 10.8 | 7.7 | 4.9 | 4.5 |
| 04-016-9683 | $V_{0.65}Mo_{0.35}O_2$ | Vanadium Molybdenum Oxide | — | 2.2 | — | — | — | — | — | — | — | — |
| 04-016-9685 | $V_{0.5}Mo_{0.5}O_2$ | Vanadium Molybdenum Oxide | — | 12.7 | — | 6.2 | — | — | — | — | — | — |
| 04-005-4566 | $Mo_8O_{23}$ | Molybdenum Oxide | — | — | — | — | — | 2.3 | — | — | — | 0.2 |
| 04-008-4547 00-035-0609 04-008-2625 01-074-7911 00-005-0508 | $MoO_3$ | Molybdenum Oxide | Molybdite | — | — | — | — | 8.6 | 15.0 | 10.5 | 11.4 | 18.4 |
| 04-013-3645 04-005-7241 01-086-0135 | $MoO_2$ | Molybdenum Oxide | Tugarinovite | 0.1 | 5.7 | — | 4.2 | — | — | — | — | — |
| 04-005-4338 04-003-5848 | $VO_2$ | Vanadium Oxide | — | — | 0.1 | 0.2 | — | — | — | — | — | — |
| 00-064-0088 | $V_2O_3$ | Vanadium Oxide | — | — | — | — | — | — | 0.1 | — | — | — |
| 04-002-6772 | $V_3O_4$ | Vanadium Oxide | — | — | 1.1 | — | — | — | — | — | — | — |

TABLE 6a-continued

| Ref. Code | Chemical formula | Compound name | Mineral name | Catalyst (Cat.) 1.1 | Cat. 1.2 | Cat. 1.3 | Cat. 1.21 | Cat. 1.7 | Cat. 1.9 | Cat. 1.11 | Cat. 1.14 | Cat. 1.20 |
|---|---|---|---|---|---|---|---|---|---|---|---|---|
| 04-009-7918 | $VO_2(H_2O)_{0.5}$ | Vanadium Oxide Hydrate | — | — | — | — | — | — | — | 2.0 | 2.4 | 4.2 |
|  |  | Amorphous Phase (wt. %) |  | 35.3 | 58.3 | 64.0 | 42.6 | 62.6 | 62.7 | 61.1 | 64.0 | 50.0 |
|  |  | RWP |  | 5.39 | 2.59 | 2.05 | — | 2.22 | 1.92 | 2.50 | 2.30 | — |
|  |  | R |  | 3.62 | 1.90 | 1.59 | 1.50 | 1.74 | 1.48 | 1.92 | 1.70 | 1.39 |
|  |  | Goodness of Fit |  | 6.09 | 2.90 | 2.41 | 2.29 | 2.66 | 2.27 | 2.89 | 2.77 | 2.24 |

TABLE 6b

| Ref. Code | Chemical formula | Compound name | Mineral name | Catalyst (Cat.) 1.1 | Cat. 1.2 | Cat. 1.3 | Cat. 1.7 | Cat. 1.9 | Cat. 1.11 | Cat. 1.14 |
|---|---|---|---|---|---|---|---|---|---|---|
| 04-015-7475 | $NbV_{1.2}Mo_{7.8}Te_{0.937}O_{28.9}$ | M1 phase* | — | — | 53.5 | — | 6.3 | 4.0 | 8.3 | 7.3 | 4.9 |
| 04-010-3742 | $V_6Mo_{12}(VO_4)O_{42}(OH)_9(H_2O)_{11}$ | Vanadium Molybdenum Vanadium Oxide Hydroxide Hydrate | — | — | — | — | — | 4.6 | 3.3 | 1.0 | 2.8 |
| 04-015-1304 | $V_{2.2}Mo_{6.6}O_{24.2}$ | Vanadium Molybdenum Oxide | — | — | — | — | 22.3 | — | — | 3.1 | — |
| 04-016-4411 | $V_2MoO_8$ | Vanadium Molybdenum Oxide | — | — | — | — | — | — | — | 2.7 | — |
| 04-011-9636 | $V_{1.48}Mo_{1.52}O_8$ | Vanadium Molybdenum Oxide | — | — | — | — | — | — | 12.2 | 13.9 | 11.0 |
| 04-005-4368 | $V_{1.19}Mo_{15.81}O_{47}$ | Vanadium Molybdenum Oxide | — | — | — | 6.8 | — | — | 0.3 | — | — |
| 04-013-6424 | $V_{1.1}Mo_{0.9}O_5$ | Vanadium Molybdenum Oxide | — | — | — | 24.0 | 25.1 | 15.5 | — | — | — |
| 04-016-9683 | $V_{0.65}Mo_{0.35}O_2$ | Vanadium Molybdenum Oxide | — | — | — | 0.8 | — | — | — | — | — |
| 04-016-9685 | $V_{0.5}Mo_{0.5}O_2$ | Vanadium Molybdenum Oxide | — | — | — | 4.6 | — | — | — | — | — |
| 04-013-3645 00-033-0929 | $MoO_2$ | Molybdenum Oxide | Tugarinovite | 0.3 | 0.5 | — | — | — | — | — |
| 00-035-0609 01-074-7909 01-074-7911 | $MoO_3$ | Molybdenum Oxide | Molybdite | — | — | — | 9.1 | 11.9 | 15.5 | 13.1 |
| 04-005-4566 | $Mo_8O_{23}$ | Molybdenum Oxide | — | — | — | — | — | — | — | 2.2 |
| 04-007-0457 00-012-0753 | $Mo_9O_{26}$ | Molybdenum Oxide | — | — | 0.6 | — | — | — | 5.4 | 5.7 |
| 04-003-5848 | $VO_2$ | Vanadium Oxide | — | — | — | — | 5.2 | — | — | — |
| 04-015-2250 | $V_2O_5$ | Vanadium Oxide | — | — | — | — | — | — | 0.4 | — |
| 01-074-1508 | $(VO)MoO_4$ | Vanadyl Molybdenum Oxide | — | — | 2.5 | — | 3.2 | 1.0 | — | — | — |
| 04-009-7918 | $VO_2(H_2O)_{0.5}$ | Vanadium Oxide Hydrate | — | — | — | — | — | — | — | 3.3 | — |
|  |  | Amorphous Phase (wt. %) |  | 43.1 | 57.3 | 37.9 | 65.8 | 62.0 | 45.2 | 57.7 |

TABLE 7a

| Ref Code | Chemical formula | Compound name | Mineral name | Catalyst (Cat.) 1.5 | Cat. 1.6 | Cat. 1.8 | Cat. 1.10 | Cat. 1.12 | Cat. 1.13 | Cat. 1.15 | Cat. 1.18 | Cat. 1.19 |
|---|---|---|---|---|---|---|---|---|---|---|---|---|
| 04-022-1665 | $V_{5.5}Mo_{14.5}O_{54.65}$ | Vanadium Molybdenum Oxide | — | 8.9 | 14.3 | 7.5 | 13.7 | 7.5 | 9.1 | 11.6 | 9.2 | 8.1 |
| 04-022-1664 | $V_{5.5}Mo_{14.5}O_{52.6}$ | Vanadium Molybdenum Oxide | — | 1.0 | — | 1.8 | 7.1 | 0.9 | 1.3 | 0.5 | 0.4 | 0.8 |
| 04-010-3742 | $V_6Mo_{12}(VO_4)O_{42}(OH)_9(H_2O)_{11}$ | Vanadium Molybdenum Vanadium Oxide Hydroxide Hydrate | — | 2.1 | 1.7 | 1.1 | 1.3 | 4.9 | 4.6 | 3.33 | — | 1.3 |
| 04-015-1304 | $V_{2.2}Mo_{6.6}O_{24.2}$ | Vanadium Molybdenum Oxide | — | — | — | — | — | — | — | — | 3.0 | 1.2 |
| 04-011-2904 | $V_{1.8}Mo_{1.2}O_8$ | Vanadium Molybdenum Oxide | — | — | — | — | — | — | — | — | — | — |
| 04-015-6540 | $V_{0.95}Mo_{0.97}O_5$ | Vanadium Molybdenum Oxide | — | — | — | — | — | — | — | — | — | 24.7 |
| 04-013-6424 | $V_{1.1}Mo_{0.9}O_5$ | Vanadium Molybdenum Oxide | — | — | — | — | 10.2 | 1.4 | — | — | — | 5.7 |
| 04-008-4548 | $Mo_9O_{26}$ | Molybdenum Oxide | — | — | 1.3 | — | — | — | — | — | — | — |
| 04-005-4566 | $Mo_8O_{23}$ | Molybdenum Oxide | — | — | — | — | — | — | — | — | 1.2 | — |
| 04-008-4547 04-012-8070 01-074-7909 04-008-3215 | $MoO_3$ | Molybdenum Oxide | Molybdite | — | — | 8.5 | 3.8 | 8.6 | 11.7 | 6.2 | 13.8 | 5.3 |
| 00-047-1081 01-080-3491 00-037-1445 | $MoO_3$ | Molybdenum-Oxide | — | 5.6 | 8.8 | — | — | — | — | — | — | — |
| 04-013-3645 04-008-2624 | $MoO_2$ | Molybdenum Oxide | Tugarinovite | 7.0 | — | — | — | — | — | — | — | 3.9 |
| 01-074-1508 | $(VO)MoO_4$ | Vanadyl Molybdenum Oxide | — | — | — | — | — | 7.6 | 7.3 | 5.6 | — | — |
| 04-007-9096 | $VO_2$ | Vanadium Oxide | — | — | 1.9 | — | — | — | — | — | — | — |
| 04-009-7918 | $VO_2(H_2O)_{0.5}$ | Vanadium Oxide Hydrate | — | — | — | 0.3 | — | — | — | — | 3.0 | — |
| 04-014-4663 00-066-0206 | $V_2O_5$ | Vanadium Oxide | — | 4.4 | 0.1 | — | — | — | — | — | — | — |
| 04-001-9096 | $V_3O_7$ | Vanadium Oxide | — | — | — | — | — | — | — | — | 2.0 | — |
| | | Amorphous Phase (wt. %) | | 71.0 | 71.8 | 69.6 | 72.6 | 70.5 | 66.0 | 72.9 | 67.2 | 48.9 |
| | | RWP | | 2.10 | 1.67 | 1.87 | 2.42 | 2.91 | 2.96 | 3.10 | — | — |
| | | R | | 1.61 | 1.33 | 1.42 | 1.70 | 2.23 | 2.23 | 2.47 | 1.72 | 1.27 |
| | | Goodness of Fit | | 2.50 | 1.91 | 2.24 | 2.81 | 3.40 | 3.48 | 3.61 | 2.68 | 1.97 |

TABLE 7b

| Ref. Code | Chemical formula | Compound name | Mineral name | Catalyst (Cat.) 1.5 | Cat. 1.6 | Cat. 1.8 | Cat. 1.10 | Cat. 1.12 | Cat. 1.13 | Cat. 1.15 |
|---|---|---|---|---|---|---|---|---|---|---|
| 04-015-7475 | $NbV_{1.2}Mo_{7.8}Te_{0.937}O_{28.9}$ | M1 phase* | — | 13.1 | 22.4 | 7.7 | 9.8 | 16.2 | 22.6 | 13.9 |
| 04-010-3742 | $V_6Mo_{12}(VO_4)O_{42}(OH)_9(H_2O)_{11}$ | Vanadium Molybdenum Vanadium Oxide Hydroxide Hydrate | — | 5.1 | — | 6.0 | 5.9 | 5.7 | 7.8 | 6.1 |
| 04-008-3219 | $MoO_2$ | Molybdenum Oxide | Tugarinovite | — | — | — | — | 0.1 | — | — |
| 04-005-7148 00-035-0609 01-074-7909 04-012-8070 | $MoO_3$ | Molybdenum Oxide | Molybdite | — | 4.4 | 1.8 | 7.4 | 14.1 | 18.7 | 13.4 |

TABLE 7b-continued

| Ref. Code | Chemical formula | Compound name | Mineral name | Catalyst (Cat.) 1.5 | Cat. 1.6 | Cat. 1.8 | Cat. 1.10 | Cat. 1.12 | Cat. 1.13 | Cat. 1.15 |
|---|---|---|---|---|---|---|---|---|---|---|
| 01-088-1799 | $MoO_3(H_2O)_2$ | Molybdenum Oxide Hydrate | Sidwillite | 8.4 | — | — | — | — | — | — |
| 04-016-3583 | $Mo_3O_9(H_2O)$ | Molybdenum Oxide Hydrate | — | — | — | — | — | 0.5 | — | — |
| 00-012-0753 04-007-0457 04-008-4548 | $Mo_9O_{26}$ | Molybdenum Oxide | — | — | — | 1.3 | — | 1.4 | — | 9.1 |
| 04-009-5028 | $V_{0.13}Mo_{0.87}O_{2.935}$ | Vanadium Molybdenum Oxide | — | — | — | — | — | 0.3 | — | — |
| 04-015-6540 | $V_{0.95}Mo_{0.97}O_5$ | Vanadium Molybdenum Oxide | — | — | — | — | 0.2 | — | — | — |
| 04-013-6424 | $V_{1.1}Mo_{0.9}O_5$ | Vanadium Molybdenum Oxide | — | — | — | 3.0 | — | — | — | — |
| 04-005-4368 | $V_{1.19}Mo_{15.81}O_{47}$ | Vanadium Molybdenum Oxide | — | — | — | — | — | 2.2 | — | — |
| 01-074-1508 | $(VO)MoO_4$ | Vanadyl Molybdenum Oxide | — | 3.4 | — | 2.1 | 0.5 | 3.9 | — | — |
| 04-014-4662 | $V_2O_5$ | Vanadium Oxide | — | 1.5 | — | — | — | — | — | — |
| | | Amorphous phase (wt. %) | | 68.6 | 69.5 | 79.3 | 74.1 | 57.9 | 50.9 | 57.5 |

PXRD Stacked Plots

The ranges of PXRD peaks identified in the peak prominence plot and their corresponding intensities for Catalysts 1.2, 1.3. 1.5-1.15, and 1.18-1.12 are shown in Table 8.

TABLE 8

| Peak number | Min angle | Max angle | Min intensity | Max intensity |
|---|---|---|---|---|
| Non-Oxalic Acid Washed Catalysts ||||
| 1 | 6.626 | 6.802 | 23.2% | 46.8% |
| 2 | 7.902 | 8.144 | 28.6% | 45.8% |
| 3 | 8.958 | 9.046 | 27.2% | 45.9% |
| 4 | 10.740 | 10.872 | 22.1% | 42.9% |
| 5 | 12.632 | 13.094 | 21.8% | 48.7% |
| 6 | 13.908 | 14.150 | 21.1% | 45.1% |
| 7 | 19.936 | 20.112 | 18.8% | 39.4% |
| 8 | 22.158 | 22.202 | 100.0% | 100.0% |
| 9 | 23.192 | 23.346 | 19.7% | 47.6% |
| 10 | 24.776 | 24.996 | 19.3% | 85.8% |
| 11 | 25.392 | 25.678 | 22.2% | 54.1% |
| 12 | 27.152 | 27.328 | 27.2% | 90.0% |
| 13 | 30.628 | 30.738 | 21.2% | 39.5% |
| 14 | 31.464 | 31.618 | 21.2% | 39.4% |
| 15 | 33.488 | 33.708 | 15.7% | 44.4% |
| 16 | 34.192 | 34.280 | 17.4% | 37.7% |
| 17 | 35.402 | 35.468 | 19.9% | 37.0% |
| 18 | 38.812 | 39.054 | 17.9% | 39.1% |
| 19 | 45.236 | 45.390 | 22.7% | 41.3% |
| 20 | 46.138 | 46.314 | 14.4% | 34.8% |
| 21 | 48.624 | 48.866 | 19.4% | 45.7% |
| 22 | 49.262 | 49.438 | 18.1% | 36.7% |
| 23 | 49.922 | 50.076 | 16.9% | 38.0% |
| 24 | 51.792 | 52.034 | 16.4% | 41.1% |
| 25 | 55.158 | 55.312 | 14.5% | 34.9% |
| Oxalic Acid Washed Catalysts ||||
| 1 | 6.538 | 6.670 | 19.3% | 33.5% |
| 2 | 7.880 | 8.254 | 22.7% | 35.4% |
| 3 | 8.276 | 8.496 | 23.5% | 34.9% |
| 4 | 8.936 | 9.046 | 22.9% | 36.3% |
| 5 | 12.720 | 12.764 | 17.1% | 39.1% |
| 6 | 22.158 | 22.224 | 100.0% | 100.0% |
| 7 | 23.346 | 23.654 | 17.7% | 31.4% |
| 8 | 25.458 | 25.766 | 18.2% | 42.5% |

TABLE 8-continued

| Peak number | Min angle | Max angle | Min intensity | Max intensity |
|---|---|---|---|---|
| 9 | 26.844 | 27.108 | 25.2% | 48.8% |
| 10 | 27.262 | 27.504 | 24.7% | 62.0% |
| 11 | 33.686 | 33.994 | 15.2% | 27.1% |
| 12 | 35.292 | 35.468 | 16.0% | 26.9% |
| 13 | 36.920 | 37.052 | 14.0% | 33.1% |
| 14 | 38.130 | 38.284 | 14.0% | 25.1% |
| 15 | 38.922 | 39.054 | 13.8% | 26.0% |
| 16 | 45.236 | 45.346 | 20.5% | 30.7% |
| 17 | 46.160 | 46.314 | 13.7% | 24.3% |
| 18 | 48.646 | 48.822 | 16.4% | 32.3% |
| 19 | 51.440 | 51.770 | 15.6% | 29.7% |
| 20 | 52.034 | 52.188 | 15.6% | 27.1% |
| 21 | 55.136 | 55.334 | 14.1% | 24.9% |

ICP-MS Elemental Analysis

ICP-MS elemental analysis for Catalysts 1.1, 1.2, and 1.3 are presented in Table 9. ICP-MS elemental analysis for Catalysts 1.7, 1.11, and 1.14 are presented in Table 10, ICP-MS elemental analysis for Catalysts 1.5, 1.6, 1.8, 1.12, 1.13, and 1.15, are presented in Table 11.

TABLE 9

| | Catalyst 1.1 | Catalyst 1.2 | Catalyst 1.3 |
|---|---|---|---|
| dilution | 444939.00 | 221099.00 | 245343.00 |
| Mo Concentration (ppm) | 532800.00 | 526700.00 | 529700.00 |
| Mo Concentration RSD | 0.60 | 0.64 | 1.80 |
| V Concentration (ppm) | 123500.00 | 138200.00 | 136100.00 |
| V Concentration RSD | 0.40 | 0.79 | 1.30 |
| Mole ratio relative to Mo | $Mo_1V_{0.44}$ | $Mo_1V_{0.49}$ | $Mo_1V_{0.48}$ |

TABLE 10

| | Catalyst 1.7 | Catalyst 1.11 | Catalyst 1.14 |
|---|---|---|---|
| dilution | 23439.00 | 196884.00 | 209110.00 |
| Mo Concentration (ppm) | 594500.00 | 549800.00 | 538800.00 |
| Mo Concentration RSD | 1.00 | 0.55 | 1.20 |

TABLE 10-continued

|  | Catalyst 1.7 | Catalyst 1.11 | Catalyst 1.14 |
|---|---|---|---|
| V Concentration (ppm) | 119700.00 | 115600.00 | 117700.00 |
| V Concentration RSD | 1.00 | 0.39 | 1.10 |
| Mole ratio relative to Mo | $Mo_1V_{0.38}$ | $Mo_1V_{0.40}$ | $Mo_1V_{0.41}$ |

TABLE 11

|  | Catalyst 1.8 | Catalyst 1.12 | Catalyst 1.13 | Catalyst 1.15 | Catalyst 1.6 | Catalyst 1.5 |
|---|---|---|---|---|---|---|
| dilution | 19881.00 | 213774.00 | 224805.00 | 189281.00 | 6301023.00 | 230823.00 |
| Mo Concentration (ppm) | 618700.00 | 569800.00 | 593300.00 | 562000.00 | 3208000.00 | 556300.00 |
| Mo Concentration RSD | 0.80 | 1.00 | 0.55 | 0.67 | 0.80 | 0.80 |
| V Concentration (ppm) | 99270.00 | 85210.00 | 84690.00 | 93890.00 | 616400.00 | 105200.00 |
| V Concentration RSD | 1.10 | 1.60 | 0.65 | 0.54 | 1.00 | 1.00 |
| Mole ratio relative to Mo | $Mo_1V_{0.30}$ | $Mo_1V_{0.28}$ | $Mo_1V_{0.27}$ | $Mo_1V_{0.31}$ | $Mo_1V_{0.36}$ | $Mo_1V_{0.36}$ |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for the oxidative dehydrogenation of ethane to ethylene comprising contacting, in an oxidative dehydrogenation reactor, ethane and oxygen with an oxidative dehydrogenation catalyst comprising molybdenum, vanadium, and oxygen, wherein:
the molar ratio of molybdenum to vanadium in the catalyst is from 1:0.15 to 1:0.75, as determined by inductively coupled plasma mass spectrometry (ICP-MS),
oxygen is present in the catalyst at least in an amount to satisfy the valency of any present metal oxides, and
the amorphous phase of the catalyst is greater than 55 wt. % from 55 wt. % to 80 wt. %, as determined by X-ray diffraction (XRD).

2. The method of claim 1 wherein the ethane and oxygen are combined with inert diluent.

3. The method of claim 1, wherein the amorphous phase is from 55 wt. % to 75 wt. %, as determined by XRD.

4. The method of claim 1, wherein the catalyst has a 35% conversion temperature from about 300° C. to about 400° C.

5. The method of claim 1, wherein the catalyst has a selectivity to ethylene from 65% to 99%.

6. The method of claim 1, wherein the catalyst is prepared by a method comprising:
providing an aqueous mixture comprising molybdenum and vanadium,
hydrothermally reacting the mixture to form a precalcined catalyst, and
calcining the precalcined catalyst to form the catalyst.

7. The method of claim 6, wherein providing the aqueous mixture comprising molybdenum and vanadium comprises combining an aqueous mixture comprising molybdenum and an aqueous mixture comprising vanadium.

8. The method of claim 7, wherein the aqueous mixture comprising molybdenum is prepared from a first composition comprising $(NH_4)_6Mo_7O_{24}.4H_2O$ and a first water.

9. The method of claim 7, wherein the aqueous mixture comprising vanadium is prepared from a second composition comprising $VOSO_4.XH_2O$ and a second water.

10. A method for the oxidative dehydrogenation of ethane to ethylene comprising contacting, in an oxidative dehydrogenation reactor, ethane and oxygen with an oxidative dehydrogenation catalyst comprising molybdenum, vanadium, and oxygen, wherein:
the molar ratio of molybdenum to vanadium in the catalyst is from 1:0.20 to 1:0.60, as determined by ICP-MS,
oxygen is present in the catalyst at least in amount to satisfy the valency of any present metal oxides, and
the amorphous phase of the catalyst is greater than 55 wt. %, as determined by XRD.

11. The method of claim 10, wherein the molar ratio of molybdenum to vanadium in the catalyst is from 1:0.24 to 1:0.58, as determined by ICP-MS.

12. The method of claim 10, wherein the amorphous phase of the catalyst is from 55 wt. % to 75 wt. %, as determined by XRD.

13. The method of claim 10, wherein the catalyst characterized by having XRD diffraction peaks (2θ degrees) at least at 23.5±0.5, 25.6±0.5, and 27.1±0.7, wherein the XRD is obtained using CuKα radiation.

14. The method of claim 10, wherein the catalyst has a 35% conversion temperature from about 300° C. to about 425° C.

15. The method of claim 10, wherein the catalyst has a selectivity to ethylene from 65% to 95%.

16. The method of claim 10, wherein the catalyst is prepared by a method comprising:
providing an aqueous mixture comprising molybdenum and vanadium,
hydrothermally reacting the mixture to form a precalcined catalyst, and
calcining the precalcined catalyst in the presence of air to form the catalyst.

17. A method for the oxidative dehydrogenation of ethane to ethylene comprising contacting, in an oxidative dehydrogenation reactor, ethane and oxygen with an oxidative dehydrogenation catalyst comprising molybdenum, vanadium, and oxygen, wherein:

the molar ratio of molybdenum to vanadium in the catalyst is from 1:0.20 to 1:0.50, as determined by ICP-MS, oxygen is present in the catalyst at least in amount to satisfy the valency of any present metal oxides, and the amorphous phase of the catalyst is greater than 55 wt. %, as determined by XRD.

18. The method of claim 17, wherein the molar ratio of molybdenum to vanadium in the catalyst is from 1:0.25 to 1:0.45, as determined by ICP-MS.

19. The method of claim 17, wherein the amorphous phase of the catalyst is from 55 wt. % to 85 wt. %, as determined by XRD.

20. The method of claim 17, wherein the catalyst is characterized by having XRD diffraction peaks (2θ degrees) at least at 23.5±0.5, 25.6±0.5, and 27.1±0.7, wherein the XRD is obtained using CuKα radiation.

21. The method of claim 17, wherein the catalyst has a 35% conversion temperature from about 320° C. to about 400° C.

22. The method of claim 17, wherein the catalyst has a selectivity to ethylene from 70% to 95%.

23. The method of claim 17, wherein the catalyst is prepared by a method comprising:

providing an aqueous mixture comprising molybdenum and vanadium, hydrothermally reacting the mixture to form a precalcined catalyst, air calcining the precalcined catalyst to form the catalyst, and washing the catalyst with an acid solution.

24. The method of claim 23, wherein the acid solution comprises oxalic acid.

25. The method of claim 24, wherein the concentration of oxalic acid is from about 0.05 M to about 0.5 M.

* * * * *